(12) United States Patent
Kumar et al.

(10) Patent No.: US 11,453,654 B2
(45) Date of Patent: Sep. 27, 2022

(54) PHOTOCHROMIC INDENO FUSED PHENANTHRENOPYRAN COMPOUNDS

(71) Applicant: Transitions Optical, Ltd., Tuam (IE)

(72) Inventors: Anil Kumar, Murrysville, PA (US); Darrin R. Dabideen, Pittsburgh, PA (US); Shengwen Yuan, Northbrook, IL (US); Massimiliano Tomasulo, Miami, FL (US)

(73) Assignee: Transitions Optical, Ltd., Tuam (IE)

( * ) Notice: Subject to any disclaimer, the term of this patent is extended or adjusted under 35 U.S.C. 154(b) by 528 days.

(21) Appl. No.: 16/500,930

(22) PCT Filed: May 10, 2017

(86) PCT No.: PCT/EP2017/061138
§ 371 (c)(1),
(2) Date: Oct. 4, 2019

(87) PCT Pub. No.: WO2018/206096
PCT Pub. Date: Nov. 15, 2018

(65) Prior Publication Data
US 2020/0048216 A1    Feb. 13, 2020

(51) Int. Cl.
*G02B 5/23* (2006.01)
*C07D 311/94* (2006.01)
*C07D 413/10* (2006.01)

(52) U.S. Cl.
CPC .......... *C07D 311/94* (2013.01); *C07D 413/10* (2013.01); *G02B 5/23* (2013.01)

(58) Field of Classification Search
CPC ....... C07D 311/94; C07D 413/10; G02B 5/23
See application file for complete search history.

(56) References Cited

U.S. PATENT DOCUMENTS

| | | |
|---|---|---|
| 4,931,220 A | 6/1990 | Haynes et al. |
| 5,625,427 A | 4/1997 | Araujo et al. |

(Continued)

FOREIGN PATENT DOCUMENTS

| | | |
|---|---|---|
| EP | 1184379 A1 | 3/2002 |
| EP | 1529780 A1 | 5/2005 |

(Continued)

OTHER PUBLICATIONS

Brown, G. "Photochromism", Techniques in Chemistry, 1971, Chapter 3, vol. III, John Wiley and Sons, Inc., New York.

*Primary Examiner* — Bijan Ahvazi
(74) *Attorney, Agent, or Firm* — The Webb Law Firm

(57) ABSTRACT

The present invention relates to photochromic indeno fused phenanthrenopyran compounds represented by the following Formula (I). With some embodiments, the photochromic compounds represented by Formula (I) include at least one lengthening group (e.g., $R^6$ and/or $R^7$ each independently being a lengthening group) and the compounds of the present invention are photochromicdichroic compounds. The present invention also relates to photochromic compositions and photochromic articles, such as photochromic ophthalmic articles that include one or more photochromic compounds represented by Formula (I).

(Continued)

Scheme 1
(Part 3)

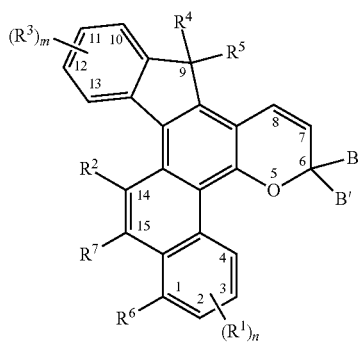

(I)

12 Claims, 3 Drawing Sheets

(56) References Cited

U.S. PATENT DOCUMENTS

| | | | |
|---|---|---|---|
| 5,645,767 A | 7/1997 | Van Gemert | |
| 5,658,501 A | 8/1997 | Kumar et al. | |
| 5,698,141 A | 12/1997 | Kumar | |
| 5,723,072 A * | 3/1998 | Kumar | C07D 493/04 |
| | | | 546/281.1 |
| 6,022,497 A | 2/2000 | Kumar | |
| 6,113,814 A | 9/2000 | Gemert et al. | |
| 6,153,126 A | 11/2000 | Kumar | |
| 6,187,444 B1 | 2/2001 | Bowles, III et al. | |
| 6,398,987 B1 | 6/2002 | Breyne et al. | |
| 6,555,028 B2 | 4/2003 | Walters et al. | |
| 6,690,495 B1 | 2/2004 | Kosa et al. | |
| 6,723,859 B2 | 4/2004 | Kawabata et al. | |
| 6,881,850 B2 | 4/2005 | Mann et al. | |
| 7,250,120 B2 | 7/2007 | Chan et al. | |
| 7,342,112 B2 | 3/2008 | Kumar et al. | |
| 7,410,691 B2 | 8/2008 | Blackburn et al. | |
| 7,910,019 B2 | 3/2011 | He et al. | |
| 8,211,338 B2 | 7/2012 | He et al. | |
| 8,518,546 B2 | 8/2013 | He et al. | |
| 8,545,984 B2 | 10/2013 | He et al. | |
| 8,698,117 B2 | 4/2014 | He et al. | |
| 9,028,728 B2 | 5/2015 | Bancroft et al. | |
| 9,034,219 B2 | 5/2015 | He et al. | |
| 9,051,332 B1 | 6/2015 | He et al. | |
| 9,475,901 B2 | 10/2016 | Saha et al. | |
| 2004/0014995 A1* | 1/2004 | Kawabata | G03C 1/685 |
| | | | 568/325 |
| 2005/0092972 A1 | 5/2005 | Chan et al. | |
| 2011/0129678 A1* | 6/2011 | He | C07D 311/92 |
| | | | 544/111 |
| 2011/0140056 A1 | 6/2011 | He et al. | |
| 2011/0143141 A1* | 6/2011 | He | G03C 1/73 |
| | | | 544/150 |
| 2015/0141661 A1* | 5/2015 | He | G02B 5/23 |
| | | | 548/417 |

FOREIGN PATENT DOCUMENTS

| | | |
|---|---|---|
| EP | 2360224 A1 | 8/2011 |
| WO | 9748993 A1 | 12/1997 |
| WO | 0229489 A2 | 4/2002 |
| WO | 2009158483 A1 | 12/2009 |
| WO | 2010065393 A1 | 6/2010 |
| WO | 2012082299 A1 | 6/2012 |
| WO | 2012082381 A1 | 6/2012 |
| WO | 2012082383 A1 | 6/2012 |
| WO | 2012082506 A1 | 6/2012 |
| WO | 2013032608 A1 | 3/2013 |
| WO | 2015077264 A1 | 5/2015 |

* cited by examiner

Scheme 1
(Part 1)

Scheme 1
(Part 2)

Scheme 1
(Part 3)

PHOTOCHROMIC INDENO FUSED PHENANTHRENOPYRAN COMPOUNDS

CROSS-REFERENCE TO RELATED APPLICATION

This application is the United States national phase of International Application No. PCT/EP2017/061138 filed May 10, 2017, the disclosure of which is hereby incorporated by reference in its entirety.

FIELD

The present invention relates to photochromic indeno fused phenanthrenopyran compounds, photochromic compositions that include such compounds, and photochromic articles, such as ophthalmic articles, that include such compounds.

BACKGROUND

Photochromic compounds and materials, in response to certain wavelengths of electromagnetic radiation (or "actinic radiation"), typically undergo a transformation from one form or state to another form, with each form having a characteristic or distinguishable absorption spectrum associated therewith. Typically, upon exposure to actinic radiation, many photochromic materials are transformed from a closed-form, which corresponds to an unactivated (or bleached, or substantially colorless) state of the photochromic material, to an open-form, which corresponds to an activated (or colored) state of the photochromic material. In the absence of exposure to actinic radiation, such photochromic materials are reversibly transformed from the activated (or colored) state, back to the unactivated (or bleached) state. Compositions and articles, such as eyewear lenses, that contain photochromic materials or have photochromic materials applied thereto (such as in form of a photochromic coating composition) typically display colorless (or clear) and colored states that correspond to the colorless and colored states of the photochromic materials contained therein and/or applied thereto. Photochromic compounds can provide a combination of both photochromic and dichroic properties when exposed to actinic radiation and properly aligned together, such as when including one or more lengthening groups covalently bonded thereto. Dichroic properties relate to the ability of the photochromic-dichroic compounds to linearly polarize incident unpolarized light. Photochromic compounds and materials are typically characterized with regard to various properties, such as photochromic properties, which include, but are not limited to: fade rate; change in optical density (sometimes designated as $\Delta OD$); and dichroic properties (such as in the case of photochromic-dichroic compounds), which can be quantified with regard to absorption ratio (AR) values.

It would be desirable to develop new photochromic compounds. It would be further desirable that such newly developed photochromic compounds possess properties, such as photochromic properties and optionally dichroic properties, that are at least the same as or better than those of existing photochromic compounds.

SUMMARY

In accordance with the present invention, there is provided a photochromic compound represented by the following Formula (I),

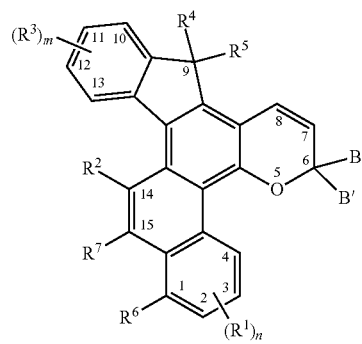

With reference to Formula (I), $R^2$ is selected from the group consisting of, hydrogen; halogen; linear or branched $C_1$-$C_{20}$ alkyl; linear or branched $C_1$-$C_{20}$ perhaloalkyl; —$OR^a$; —$SR^a$, where each $R^a$ is independently selected from the group consisting of hydrogen, linear or branched $C_1$-$C_{20}$ alkyl, and linear or branched $C_1$-$C_{20}$ perhaloalkyl; —$C(O)OR^b$, where $R^b$ is hydrogen or linear or branched $C_1$-$C_{10}$ alkyl; substituted or unsubstituted aryl, each aryl substituent being independently selected from the group consisting of hydroxyl, halogen, carbonyl, linear or branched $C_1$-$C_{20}$ alkoxycarbonyl, cyano, linear or branched $C_1$-$C_{20}$ haloalkyl, linear or branched $C_1$-$C_{20}$ alkyl, linear or branched $C_1$-$C_{20}$ alkoxy, and linear or branched $C_1$-$C_{20}$ perhaloalkyl; and a group $Y^1$ (as described further herein).

With additional reference to Formula (I), $R^6$ and $R^7$ are each independently selected from the group consisting of, hydrogen; halogen; a lengthening group $L^1$ (as described in further detail herein); —$OR^c$, and —$SR^c$, where each $R^c$ is independently selected from the group consisting of hydrogen, a lengthening group $L^2$ (as described in further detail herein), linear or branched $C_1$-$C_{20}$ alkyl, —$C(O)$—$R^d$, and —$S(O)(O)$—$R^e$, where $R^d$ and $R^e$ are each independently selected from the group consisting of linear or branched $C_1$-$C_{10}$ alkyl, linear or branched $C_1$-$C_{10}$ perhaloalkyl, phenyl, linear or branched $C_1$-$C_{10}$ alkyl substituted phenyl, and linear or branched $C_1$-$C_{10}$ perhaloalkyl substituted phenyl. With regard to $R^6$ and $R^7$ of Formula (I), there is the proviso that at least one of $R^6$ and $R^7$ is other than hydrogen.

With reference to Formula (I), n is 1 to 3, and m is 1 to 4. With further reference to Formula (I), $R^1$ independently for each n, and $R^3$ independently for each m are each independently selected from the group consisting of: (1) hydrogen; (2) cyano; (3) a reactive substituent; (4) a lengthening group $L^3$ (as described in further detail herein); (5) halogen selected from the group consisting of fluoro, chloro, and bromo; (6) linear or branched $C_1$-$C_{20}$ alkyl; (7) linear or branched $C_1$-$C_{20}$ perhaloalkyl; (8) $C_3$-$C_{10}$ cycloalkyl; (9) a group $Y^2$ (as described in further detail herein); (10) substituted or unsubstituted phenyl, the phenyl substituents being selected from the group consisting of at least one of hydroxyl, halogen, carbonyl, linear or branched $C_1$-$C_{20}$ alkoxycarbonyl, cyano, linear or branched $C_1$-$C_{20}$ haloalkyl, linear or branched $C_1$-$C_{20}$ alkyl, linear or branched $C_1$-$C_{20}$ alkoxy, linear or branched $C_1$-$C_{20}$ perhaloalkyl, and combinations thereof; (11) —O—$R_{10}'$, —S—$R_{10}'$, —C(O)—$R_{10}'$, —C(O)—$OR_{10}'$, —OC(O)—$R_{10}'$, —OC(O)O—$R_{10}'$, —C(O)N($R_{10}'$)$R_{10}'$, —N($R_{10}'$)C(O)N($R_{10}'$)($R_{10}'$), or —Si$(OR_{10}')_w(R_{10}')_t$, wherein each $R_{10}'$ independently is hydrogen, linear or branched $C_1$-$C_{20}$ alkyl, phenyl($C_1$-$C_{20}$)alkyl, mono($C_1$-$C_{20}$)alkyl substituted phenyl($C_1$-$C_{20}$)alkyl, mono($C_1$-$C_{20}$)alkoxy substituted phenyl($C_1$-$C_{20}$)alkyl, ($C_1$-$C_{20}$)

alkoxy($C_2$-$C_{20}$)alkyl, $C_3$-$C_{10}$ cycloalkyl, or mono($C_1$-$C_{20}$) alkyl substituted $C_3$-$C_{10}$ cycloalkyl, and w and t are each independently 0 to 3, provided that w+t is 3; and (12) —N($R_{11}'$)$R_{12}'$, wherein $R_{11}'$ and $R_{12}'$ are each independently hydrogen, linear or branched $C_1$-$C_{20}$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, linear or branched $C_1$-$C_{20}$ alkylaryl, $C_3$-$C_{10}$ cycloalkyl, $C_4$-$C_{20}$ bicycloalkyl, $C_5$-$C_{20}$ tricycloalkyl or linear or branched $C_1$-$C_{20}$ alkoxyalkyl, wherein the aryl group is phenyl or naphthyl, or $R_{11}'$ and $R_{12}'$ come together with the nitrogen atom to form a ring, such as a $C_3$-$C_{20}$ hetero-bicycloalkyl ring or a $C_4$-$C_{20}$ hetero-tricycloalkyl ring.

With reference to Formula (I), $R^4$ and $R^5$ are each independently selected from the group consisting of: (i) hydrogen, hydroxyl, linear or branched $C_1$-$C_{20}$ alkyl, linear or branched $C_1$-$C_{20}$ haloalkyl, $C_3$-$C_{10}$ cycloalkyl, allyl, benzyl, or substituted benzyl, the benzyl substituents being chosen from halogen, linear or branched $C_1$-$C_{20}$ alkyl or linear or branched $C_1$-$C_{20}$ alkoxy; (ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl, the group substituents in each case being independently chosen from halogen, linear or branched $C_1$-$C_{20}$ alkyl or linear or branched $C_1$-$C_{20}$ alkoxy; and (iii) a group $Y^3$; or (iv) $R^4$ and $R^5$ together form a spiro substituent selected from the group consisting of a substituted or unsubstituted spiro-carbocyclic ring containing 3 to 10 carbon atoms, a substituted or unsubstituted spiro-heterocyclic ring containing 1 or 2 oxygen atoms and 3 to 10 carbon atoms including the spirocarbon atom, the spiro-carbocyclic ring and spiro-heterocyclic ring being annellated with 0, 1 or 2 benzene rings, the substituents being hydrogen or linear or branched $C_1$-$C_{20}$ alkyl.

With additional reference to Formula (I), B and B' are each independently selected from the group consisting of unsubstituted aryl, substituted aryl, unsubstituted heteroaryl, substituted heteroaryl, alkenyl, and alkynyl, or B and B' taken together form a ring structure.

With reference to Formula (I) and the various groups thereof, each lengthening group $L^1$, $L^2$, and $L^3$ is independently represented by the following Formula (II):

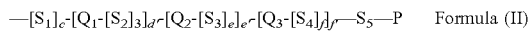

—[$S_1$]$_c$-[$Q_1$-[$S_2$]$_3$]$_d$-[$Q_2$-[$S_3$]$_e$]$_e$-[$Q_3$-[$S_4$]$_f$]$_f$—$S_5$—P  Formula (II)

With reference to Formula (II), (a) $Q_1$, $Q_2$, and $Q_3$ for each occurrence, are independently a divalent group selected from the group consisting of unsubstituted aryl, substituted aryl, unsubstituted heteroaryl, substituted heteroaryl, unsubstituted cycloalkyl, substituted cycloalkyl, unsubstituted heterocycloalky, and substituted heterocycloalkyl. The aryl substituents, heteroaryl substituents, cycloalkyl substituents, and heterocycloalkyl substituents, of $Q_1$, $Q_2$, and $Q_3$, are each independently selected from the group consisting of P (as described in further detail herein), liquid crystal mesogens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$)alkoxy, perfluoro($C_1$-$C_{18}$) alkoxycarbonyl, perfluoro($C_1$-$C_{18}$)alkylcarbonyl, perfluoro ($C_1$-$C_{18}$)alkylamino, di-(perfluoro($C_1$-$C_{18}$)alkyl)amino, perfluoro($C_1$-$C_{18}$)alkylthio, $C_1$-$C_{18}$ alkylthio, $C_1$-$C_{18}$ acetyl, $C_3$-$C_{10}$ cycloalkyl, $C_3$-$C_{10}$ cycloalkoxy, straight-chain $C_1$-$C_{18}$ alkyl, and branched $C_1$-$C_{18}$ alkyl. The straight-chain $C_1$-$C_{18}$ alkyl and branched $C_1$-$C_{18}$ alkyl (of the aryl substituents, heteroaryl substituents, cycloalkyl substituents, and heterocycloalkyl substituents, of $Q_1$, $Q_2$, and $Q_3$,) are each independently mono-substituted with a group selected from the group consisting of cyano, halogen, and $C_1$-$C_{18}$ alkoxy. Alternatively, the straight-chain $C_1$-$C_{18}$ alkyl and branched $C_1$-$C_{18}$ alkyl (of the aryl substituents, heteroaryl substituents, cycloalkyl substituents, and heterocycloalkyl substituents, of $Q_1$, $Q_2$, and $Q_3$,) are each independently poly-substituted with at least two groups independently selected from the group consisting of halogen, -M(T)$_{(v-1)}$ and -M(OT)$_{(v-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and v is the valence of M.

With further reference to Formula (II), (b) subscripts c, d, e, and f are each independently chosen from an integer of 1 to 20; and each $S_1$, $S_2$, $S_3$, $S_4$, and $S_5$ is independently chosen for each occurrence from a spacer unit selected from the group consisting of: (i) alkylene, substituted alkylene, haloalkylene, substituted haloalkylene, —Si(CH$_2$)$_g$—, and —(Si[(CH$_3$)$_2$]O)$_h$—, wherein g for each occurrence is independently chosen from an integer from 1 to 20; h for each occurrence is independently chosen from an integer from 1 to 16; and the substitutes for the alkylene and haloalkylene are independently selected from the group consisting of $C_1$-$C_{18}$ alkyl, $C_3$-$C_{10}$ cycloalkyl and aryl; (ii) —N(Z)—, —C(Z)=C(Z)—, —C(Z)=N—, —C(Z')$_2$—C(Z)$_2$—, —N(Z)—C(Z)$_2$—, and a single bond, wherein Z for each occurrence is independently selected from the group consisting of hydrogen, $C_1$-$C_{18}$ alkyl, $C_3$-$C_{10}$ cycloalkyl and aryl, and Z' for each occurrence is independently selected from the group consisting of $C_1$-$C_{18}$ alkyl, $C_3$-$C_{10}$ cycloalkyl and aryl; and (iii) —O—, —C(=O)—, —C≡C—, —N=N—, —S—, —S(=O)—, —(O=)S(=O)—, —(O=)S(=O)O—, —O(O=)S(=O)O— and straight-chain or branched $C_1$-$C_{24}$ alkylene residue, the $C_1$-$C_{24}$ alkylene residue being unsubstituted, mono-substituted by cyano or halogen, or poly-substituted by halogen. With regard to each of $S_1$, $S_2$, $S_3$, $S_4$, and $S_5$, there is the proviso that when two spacer units comprising heteroatoms are linked together the spacer units are linked so that heteroatoms are not directly linked to each other, and the bond between $S_5$ and P is free of two heteroatoms linked to each other.

With additional reference to Formula (II), (c) P for each occurrence is independently selected from the group consisting of hydroxy, amino, $C_2$-$C_{18}$ alkenyl, $C_2$-$C_{18}$ alkynyl, azido, silyl, siloxy, silylhydride, (tetrahydro-2H-pyran-2-yl) oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$)alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$)alkylamino, $C_1$-$C_{18}$ alkyl ($C_1$-$C_{18}$)alkoxy, $C_1$-$C_{18}$ alkoxy($C_1$-$C_{18}$)alkoxy, nitro, poly ($C_1$-$C_{18}$)alkyl ether, ($C_1$-$C_{18}$)alkyl($C_1$-$C_{18}$)alkoxy($C_1$-$C_{18}$) alkyl, polyethyleneoxy, polypropyleneoxy, ethylene, acryloyl, acryloyloxy($C_1$-$C_{18}$)alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, maleimide derivatives, fumaric acid derivatives, unsubstituted cinnamic acid derivatives, cinnamic acid derivatives that are substituted with at least one of methyl, methoxy, cyano and halogen, and substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro($C_1$-$C_{18}$)alkyl, cyano, cyano($C_1$-$C_{18}$)alkyl, cyano($C_1$-$C_{18}$)alkoxy or mixtures thereof, or P is a structure having from 2 to 4 reactive groups, or P is an unsubstituted or substituted ring opening metathesis polymerization precursor, or P is a substituted or unsubstituted photochromic compound.

With further additional reference to Formula (II), subscripts d', e' and f' are each independently chosen from 0, 1, 2, 3, and 4, provided that the sum of d'+e'+f' is at least 1.

With reference to Formula (I) and the various groups thereof, each group $Y^1$, $Y^2$, and $Y^3$ independently comprises at least one residue of a ring-opened cyclic monomer, wherein each ring-opened cyclic monomer is independently selected from the group consisting of a ring-opened cyclic ester monomer and a ring-opened cyclic carbonate monomer.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWINGS

In FIGS. 1(a) through 1(c), like characters refer to the same compounds and/or reactants, as the case may be, unless otherwise stated.

DETAILED DESCRIPTION

Figure 1A:
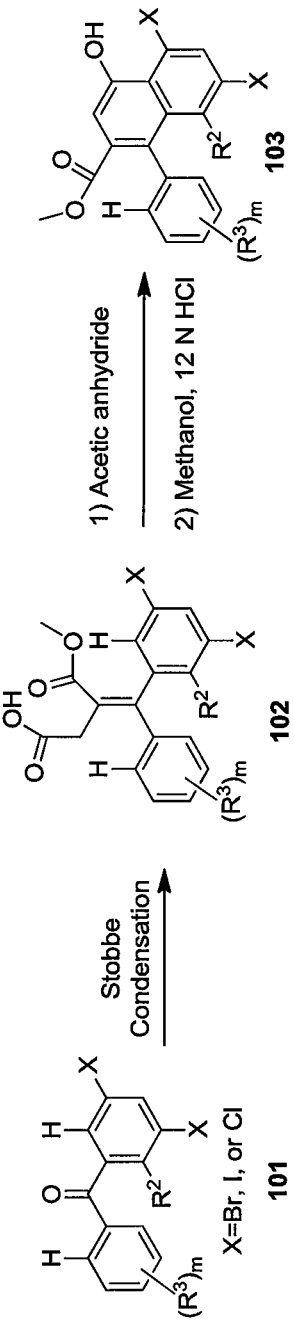
FIG. 1(a) is an illustrative representative first part (Part 1) of a general scheme, Scheme 1, of a method for preparing photochromic compounds according to some embodiments of the present invention, such as represented by Formula (I), as described further herein.

As used herein, the articles "a," "an," and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

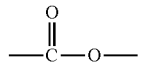

or equivalently —C(O)O—, is inclusive of the right-to-left representation thereof,

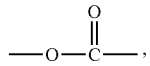

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about."

As used herein, molecular weight values of polymers, such as weight average molecular weights (Mw) and number average molecular weights (Mn), are determined by gel permeation chromatography using appropriate standards, such as polystyrene standards.

As used herein, polydispersity index (PDI) values represent a ratio of the weight average molecular weight (Mw) to the number average molecular weight (Mn) of the polymer (i.e., Mw/Mn).

As used herein, the term "polymer" means homopolymers (e.g., prepared from a single monomer species), copolymers (e.g., prepared from at least two monomer species), and graft polymers.

As used herein, the term "(meth)acrylate" and similar terms, such as "(meth)acrylic acid ester" means methacrylates and/or acrylates. As used herein, the term "(meth) acrylic acid" means methacrylic acid and/or acrylic acid.

The photochromic compounds of the present invention are, with some embodiments, also referred to herein as photochromic-dichroic compounds (e.g., when they include one or more lengthening groups, such as $L_1$, $L_2$, and/or $L_3$).

The photochromic compounds of the present invention, as described herein, including, but not limited to, photochromic compounds represented by Formula (I) and, in each case can optionally further include one or more coproducts, resulting from the synthesis of such compounds.

As used herein, the term "photochromic" and similar terms, such as "photochromic compound" means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "actinic radiation" means electromagnetic radiation that is capable of causing a response in a material, such as, but not limited to, transforming a photochromic material from one form or state to another as will be discussed in further detail herein.

As used herein, the term "photochromic material" includes thermally reversible photochromic materials and compounds and non-thermally reversible photochromic materials and compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein to modify the term "state," the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound of the present invention can be clear in the first state and colored in the second state. Alternatively, a photochromic compound of the present invention can have a first color in the first state and a second color in the second state.

As used herein the term "optical" means pertaining to or associated with light and/or vision. For example, according to various non-limiting embodiments disclosed herein, the optical article or element or device can be chosen from ophthalmic articles, elements and devices, display articles, elements and devices, windows, mirrors, and active and passive liquid crystal cell articles, elements and devices.

As used herein the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein the term "display" means the visible or machine-readable representation of information in words, numbers, symbols, designs or drawings. Non-limiting examples of display elements include screens, monitors, and security elements, such as security marks.

As used herein the term "window" means an aperture adapted to permit the transmission of radiation therethrough. Non-limiting examples of windows include automotive and aircraft transparencies, windshields, filters, shutters, and optical switches.

As used herein the term "mirror" means a surface that specularly reflects a large fraction of incident light.

As used herein the term "liquid crystal cell" refers to a structure containing a liquid crystal material that is capable of being ordered. A non-limiting example of a liquid crystal cell element is a liquid crystal display.

As used herein, spatial or directional terms, such as "left", "right", "inner", "outer", "above", "below", and the like, relate to the invention as it is depicted in the drawing figures. It is to be understood, however, that the invention can assume various alternative orientations and, accordingly, such terms are not to be considered as limiting.

As used herein, the terms "formed over," "deposited over," "provided over," "applied over," residing over," or "positioned over," mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

As used herein, recitations relating to ring positions, such as but not limited to, position-x (e.g., position-11 or position-12) means a particular position in the ring structure, such as the fused ring structure, of a chemical compound, such as the photochromic indeno fused phenanthrenopyran compounds of the present invention, and which are depicted herein in accordance with some embodiments by numbers within the ring structures of representative chemical formulas.

All documents, such as but not limited to issued patents and patent applications, referred to herein, and unless otherwise indicated, are to be considered to be "incorporated by reference" in their entirety.

As used herein, recitations of "linear or branched" groups, such as linear or branched alkyl, are herein understood to include: a methylene group or a methyl group; groups that are linear (or "straight"), such as linear $C_2$-$C_{20}$ alkyl groups; and groups that are appropriately branched, such as branched $C_3$-$C_{20}$ alkyl groups.

As used herein, recitations of alkyl groups, alkenyl groups, and alkynyl groups that include more than two carbon atoms, include linear or branched forms (or arrangements) thereof.

As used herein, recitations of "optionally substituted" group, means a group, including but not limited to, alkyl group, cycloalkyl group, heterocycloalkyl group, aryl group, and/or heteroaryl group, in which at least one hydrogen thereof has been optionally replaced or substituted with a group that is other than hydrogen, such as, but not limited to: halo groups (e.g., F, Cl, I, and Br); hydroxyl groups; ether groups; thiol groups; thio ether groups; carboxylic acid groups; carboxylic acid ester groups; phosphoric acid groups; phosphoric acid ester groups; sulfonic acid groups; sulfonic acid ester groups; nitro groups; cyano groups; alkyl groups; alkenyl groups; alkynyl groups; cycloalkyl groups (including poly-fused-ring cycloalkyl and polycyclocalkyl groups); heterocycloalkyl groups; aryl groups (including hydroxyl substituted aryl, such as phenol, and including poly-fused-ring aryl); heteroaryl groups (including poly-fused-ring heteroaryl groups); aralkyl groups; amine groups, such as —N($R_{11}$')($R_{12}$') where $R_{11}$' and $R_{12}$' are each independently selected, with some embodiments, from hydrogen, linear or branched $C_1$-$C_{20}$ alkyl, $C_3$-$C_{12}$ cycloalkyl, $C_3$-$C_{12}$ heterocycloalkyl, aryl, and heteroaryl; and reactive substituents, including those classes and examples as described further herein.

As used herein, recitations of "halo substituted" and related terms (such as, but not limited to, haloalkyl groups, haloalkenyl groups, haloalkynyl groups, haloaryl groups and halo-heteroaryl groups) means a group in which at least one, and up to and including all of the available hydrogen groups thereof is substituted with a halo group. The term "halo-substituted" is inclusive of "perhalo-substituted." As used herein, the term perhalo-substituted group and related terms (such as, but not limited to perhaloalkyl groups, perhaloalkenyl groups, perhaloalkynyl groups, perhaloaryl groups and perhalo-heteroaryl groups) means a group in which all of the available hydrogen groups thereof are substituted with a halo group. For example, perhalomethyl is —$CX_3$; perhalophenyl is —$C_6X_5$, where X represents one or more halo groups, such as, but not limited to F.

The term "alkyl" as used herein, in accordance with some embodiments, means linear or branched alkyl, such as but not limited to, linear or branched $C_1$-$C_{25}$ alkyl, or linear or branched $C_1$-$C_{10}$ alkyl, or linear or branched $C_2$-$C_{10}$ alkyl. Examples of alkyl groups from which the various alkyl groups of the present invention can be selected from, include, but are not limited to, those recited previously herein. Alkyl groups of the various compounds of the present invention can, with some embodiments, include one or more unsaturated linkages selected from —CH═CH— groups and/or one or more —C≡C— groups, provided the alkyl group is free of two or more conjugated unsaturated linkages. With some embodiments, the alkyl groups are free of unsaturated linkages, such as —CH═CH— groups and —C≡C— groups.

The term "cycloalkyl" as used herein, in accordance with some embodiments, means groups that are appropriately cyclic, such as but not limited to, $C_3$-$C_{12}$ cycloalkyl (including, but not limited to, cyclic $C_5$-$C_7$ alkyl) groups. Examples of cycloalkyl groups include, but are not limited to, those recited previously herein. The term "cycloalkyl" as used herein in accordance with some embodiments also includes: bridged ring polycycloalkyl groups (or bridged ring polycyclic alkyl groups), such as but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein, in accordance with some embodiments, means groups that are appropriately cyclic, such as but not limited to, $C_3$-$C_{12}$ heterocycloalkyl groups or $C_5$-$C_7$ heterocycloalkyl groups, and which have at least one hetero atom in the cyclic ring, such as, but not limited to, O, S, N, P, and combinations thereof. Examples of heterocycloalkyl groups include, but are not limited to, those recited previously herein. The term "heterocycloalkyl" as used herein, in accordance with some embodiments, also includes: bridged ring polycyclic heterocycloalkyl groups, such as but not limited to, 7-oxabicyclo[2.2.1]heptanyl; and fused ring polycyclic heterocycloalkyl groups, such as but not limited to, octahydrocyclopenta[b]pyranyl, and octahydro-1H-isochromenyl.

The term "heteroaryl," as used herein, in accordance with some embodiments, includes but is not limited to $C_5$-$C_{18}$ heteroaryl, such as but not limited to $C_5$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, those recited previously herein.

As used herein, the term "fused ring polycyclic-aryl-alkyl group" and similar terms such as, fused ring polycyclic-alkyl-aryl group, fused ring polycyclo-aryl-alkyl group, and fused ring polycyclo-alkyl-aryl group means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to indenyl, 9H-flourenyl, cyclopentanaphthenyl, and indacenyl.

The term "aralkyl," as used herein, and in accordance with some embodiments, includes but is not limited to $C_6$-$C_{24}$ aralkyl, such as but not limited to $C_6$-$C_{10}$ aralkyl, and means an aryl group substituted with an alkyl group. Examples of aralkyl groups include, but are not limited to, those recited previously herein.

The photochromic indeno fused phenanthrenopyran compounds according to the present invention, such as, but not limited to those represented by Formula (I), and the various groups thereof are described in further detail herein as follows.

With reference to Formula (I) and with some embodiments of the present invention, $R^2$ is selected from, hydrogen; fluoro; chloro; bromo; linear or branched $C_1$-$C_{10}$ alkyl; linear or branched $C_1$-$C_{10}$ perhaloalkyl; —$OR^a$; —$SR^a$, where each $R^a$ is independently selected from hydrogen, linear or branched $C_1$-$C_{10}$ alkyl, and linear or branched $C_1$-$C_{10}$ perhaloalkyl; —$C(O)OR^b$, where $R^b$ is hydrogen or linear or branched $C_1$-$C_6$ alkyl; substituted or unsubstituted phenyl, each phenyl substituent being independently selected from hydroxyl, halogen, carbonyl, linear or branched $C_1$-$C_{10}$ alkoxycarbonyl, cyano, linear or branched $C_1$-$C_{10}$ haloalkyl, linear or branched $C_1$-$C_{10}$ alkyl, linear or branched $C_1$-$C_{10}$ alkoxy, and linear or branched $C_1$-$C_{10}$ perhaloalkyl; and the group $Y^1$.

With some additional embodiments of the present invention, and with reference to Formula (I), $R^2$ is selected from, hydrogen; fluoro; chloro; bromo; linear or branched $C_1$-$C_6$ alkyl; linear or branched $C_1$-$C_6$ perhaloalkyl; —$OR^a$; —$SR^a$, where each $R^a$ is independently selected from hydrogen, linear or branched $C_1$-$C_6$ alkyl, and linear or branched $C_1$-$C_6$ perhaloalkyl; —$C(O)OR^b$, where $R^b$ is hydrogen or linear or branched $C_1$-$C_3$ alkyl; substituted or unsubstituted phenyl, each phenyl substituent being independently selected from hydroxyl, halogen, linear or branched $C_1$-$C_6$ alkoxycarbonyl, cyano, linear or branched $C_1$-$C_6$ haloalkyl, linear or branched $C_1$-$C_6$ alkyl, linear or branched $C_1$-$C_6$ alkoxy, and linear or branched $C_1$-$C_6$ perhaloalkyl; and the group $Y^1$.

With reference to Formula (I), and with some embodiments of the present invention, $R^6$ and $R^7$ are each independently selected from, hydrogen; fluoro; chloro; bromo; the lengthening group $L^1$; —$OR^c$ and —$SR^c$, where each $R^c$ is independently selected from hydrogen, the lengthening group $L^2$, linear or branched $C_1$-$C_{10}$ alkyl, —C(O)—$R^d$, and —S(O)(O)—$R^e$, where $R^d$ and $R^e$ are each independently selected from linear or branched $C_1$-$C_6$ alkyl, linear or branched $C_1$-$C_6$ perhaloalkyl, phenyl, linear or branched $C_1$-$C_6$ alkyl substituted phenyl, and linear or branched $C_1$-$C_6$ perhaloalkyl substituted phenyl.

With further reference to Formula (I), and with some further embodiments of the present invention, $R^6$ and $R^7$ are each independently selected from, hydrogen; fluoro; chloro; bromo; lengthening group $L^1$; —$OR^c$; and —$SR^c$, where each $R^c$ is independently selected from hydrogen, the lengthening group $L^2$, linear or branched $C_1$-$C_6$ alkyl, —C(O)—$R^d$, and —S(O)(O)—$R^e$, where $R^d$ and $R^e$ are each independently selected from linear or branched $C_1$-$C_3$ alkyl, linear or branched $C_1$-$C_3$ perhaloalkyl, phenyl, linear or branched $C_1$-$C_3$ alkyl substituted phenyl, and linear or branched $C_1$-$C_3$ perhaloalkyl substituted phenyl.

In accordance with some embodiments of the present invention and with reference to Figure (I), $R^1$ independently for each n, and $R^3$ independently for each m, are each independently selected from, (1) hydrogen; (2) cyano; (3)

lengthening group $L^3$; (4) halogen selected from fluoro, chloro, and bromo; (5) linear or branched $C_1$-$C_{10}$ alkyl; (6) linear or branched $C_1$-$C_{10}$ perhaloalkyl; (7) $C_3$-$C_7$ cycloalkyl; (8) —O—$R_{10}$'; (9) —S—$R_{10}$'; (10) the group $Y^2$; and (11) substituted or unsubstituted phenyl, in which the phenyl substituents are selected from at least one of hydroxyl, halogen, carbonyl, linear or branched $C_1$-$C_{10}$ alkoxycarbonyl, cyano, linear or branched $C_1$-$C_{10}$ haloalkyl, linear or branched $C_1$-$C_{10}$ alkyl, linear or branched $C_1$-$C_{10}$ alkoxy, linear or branched $C_1$-$C_{10}$ perhaloalkyl, and combinations thereof. Each $R_{10}$', of —O—$R_{10}$' and —S—$R_{10}$' (of $R^1$ and/or $R^3$), independently is, with some embodiments, hydrogen, linear or branched $C_1$-$C_{10}$ alkyl, phenyl($C_1$-$C_{10}$)alkyl, mono($C_1$-$C_{10}$)alkyl substituted phenyl($C_1$-$C_{10}$)alkyl, mono($C_1$-$C_{10}$)alkoxy substituted phenyl($C_1$-$C_{10}$)alkyl, ($C_1$-$C_{10}$)alkoxy($C_2$-$C_{10}$)alkyl, $C_3$-$C_7$ cycloalkyl, or mono($C_1$-$C_{10}$)alkyl substituted $C_3$-$C_7$ cycloalkyl.

In accordance with some further embodiments of the present invention and with further reference to Figure (I), $R^1$ independently for each n, and $R^3$ independently for each m, are each independently selected from: (1) hydrogen; (2) cyano; (3) the lengthening group $L^3$; (4) linear or branched $C_1$-$C_6$ alkyl; (5) $C_3$-$C_6$ cycloalkyl; (6) linear or branched $C_1$-$C_8$ perhaloalkyl; (7) fluoro, chloro, and bromo; (8) —O—$R_{10}$'; (9) —S—$R_{10}$'; (10) the group $Y^2$; and (11) substituted or unsubstituted phenyl, the phenyl substituents being selected from at least one of hydroxyl, halogen, linear or branched $C_1$-$C_6$ alkoxycarbonyl, cyano, linear or branched $C_1$-$C_6$ haloalkyl, linear or branched $C_1$-$C_6$ alkyl, linear or branched $C_1$-$C_6$ alkoxy, and linear or branched $C_1$-$C_6$ perhaloalkyl. Each $R_{10}$', of —O—$R_{10}$' and —S—$R_{10}$' (of $R^1$ and/or $R^3$), independently is, with some embodiments, hydrogen, linear or branched $C_1$-$C_6$ alkyl, phenyl($C_1$-$C_6$)alkyl, mono($C_1$-$C_6$)alkyl substituted phenyl($C_1$-$C_6$)alkyl, mono($C_1$-$C_6$)alkoxy substituted phenyl($C_1$-$C_6$)alkyl, ($C_1$-$C_6$)alkoxy($C_2$-$C_6$)alkyl, $C_3$-$C_6$ cycloalkyl, or mono($C_1$-$C_6$)alkyl substituted $C_3$-$C_6$ cycloalkyl.

With some embodiments, $R^1$ independently for each n, and $R^3$ independently for each m, are in each case independently selected from, a nitrogen containing ring represented by the following graphic formula XIIA,

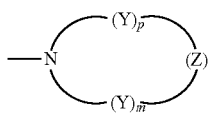

XIIA

With reference to Formula XIIA: each —Y— is independently chosen for each occurrence from —$CH_2$—, —CH($R_{13}$')—, —C($R_{13}$')$_2$—, —CH(aryl)-, —C(aryl)$_2$-, and —C($R_{13}$')(aryl)-; and Z is —Y—, —O—, —S—, —S(O)—, —$SO_2$—, —NH—, —N($R_{13}$')—, or —N(aryl)-, wherein each $R_{13}$' is independently $C_1$-$C_{20}$ alkyl, each aryl is independently phenyl or naphthyl, m is an integer 1, 2 or 3, and p is an integer 0, 1, 2, or 3, and provided that when p is 0, Z is —Y—.

With some embodiments, $R^1$ independently for each n, and $R^3$ independently for each m, are in each case independently selected from, a group represented by one of the following graphic formulas XIIB or XIIC,

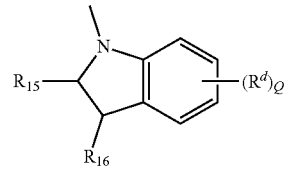

XIIB

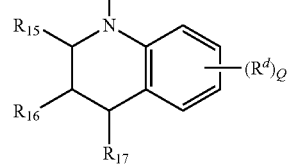

XIIC

Independently for each of Formulas XIIB and XIIC, $R_{15}$, $R_{16}$, and $R_{17}$ are each independently hydrogen, $C_1$-$C_6$ alkyl, phenyl, or naphthyl, or the groups $R_{15}$ and $R_{16}$ together form a ring of 5 to 8 carbon atoms and each $R^d$ is independently for each occurrence selected from $C_1$-$C_{20}$ alkyl, $C_1$-$C_{20}$ alkoxy, fluoro or chloro, and Q is an integer 0, 1, 2, or 3.

In accordance with some additional embodiments and with further reference to Formula (I), two adjacent $R^3$ groups together form a group represented by the following Formulas XIID or XIIE:

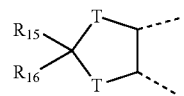

XIID

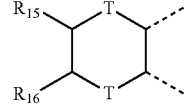

XIIE

With reference to Formulas XIID and XIIE, T and T' are each independently oxygen or the group —$NR_{11}$'—, where $R_{11}$', $R_{15}$, and $R_{16}$ are as set forth above.

With reference to Formula (I), and with some embodiments of the present invention, $R^4$ and $R^5$ are each independently selected from: hydrogen; linear or branched $C_1$-$C_{10}$ alkyl; linear or branched $C_1$-$C_{10}$ haloalkyl; $C_3$-$C_7$ cycloalkyl; and the group $Y^3$; or $R^4$ and $R^5$ together form a spiro substituent that is a substituted or unsubstituted spiro-carbocyclic ring containing 3 to 10 carbon atoms.

With further reference to Formula (I), and with some further embodiments of the present invention, $R^4$ and $R^5$ are each independently selected from: hydrogen; linear or branched $C_1$-$C_8$ alkyl; linear or branched $C_1$-$C_8$ haloalkyl; $C_3$-$C_6$ cycloalkyl; and the group $Y^3$; or $R^4$ and $R^5$ together form a spiro substituent that is a substituted or unsubstituted spiro-carbocyclic ring containing 3 to 10 carbon atoms.

With reference to Formula (I), and with some embodiments of the present invention, B and B' are in each case independently selected from: an aryl group that is monosubstituted with a reactive substituent; a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolindinyl, or heteroaromatic substituent is a reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl.

Each of the phenyl, aryl and heteroaromatic substituents (of B and B') are each independently, with some embodiments: (a) hydroxyl, a group —C(=O)$R_{21}$, wherein $R_{21}$ is —$OR_{22}$, —$N(R_{23})R_{24}$, piperidino, or morpholino, wherein $R_{22}$ is allyl, linear or branched $C_1$-$C_{20}$ alkyl, phenyl, mono ($C_1$-$C_{20}$)alkyl substituted phenyl, mono($C_1$-$C_{20}$)alkoxy substituted phenyl, phenyl($C_1$-$C_{20}$)alkyl, mono($C_1$-$C_{20}$)alkyl substituted phenyl($C_1$-$C_{20}$)alkyl, mono($C_1$-$C_{20}$)alkoxy substituted phenyl($C_1$-$C_{20}$)alkyl, $C_1$-$C_{20}$ alkoxy($C_2$-$C_{20}$)alkyl or $C_1$-$C_{20}$ haloalkyl, $R_{23}$ and $R_{24}$ are each independently $C_1$-$C_{20}$ alkyl, $C_5$-$C_{10}$ cycloalkyl, phenyl or substituted phenyl, the phenyl substituents being $C_1$-$C_{20}$ alkyl or $C_1$-$C_{20}$ alkoxy, and the halo substituent is chloro or fluoro, aryl, mono($C_1$-$C_{20}$)alkoxyaryl, di($C_1$-$C_{20}$)alkoxyaryl, mono($C_1$-$C_{20}$)alkylaryl, di($C_1$-$C_{20}$)alkylaryl, haloaryl, $C_3$-$C_{10}$ cycloalkylaryl, $C_3$-$C_{10}$ cycloalkyl, $C_3$-$C_{10}$ cycloalkyloxy, $C_3$-$C_{10}$ cycloalkyloxy($C_1$-$C_{20}$)alkyl, $C_3$-$C_{10}$ cycloalkyloxy($C_1$-$C_{20}$)alkoxy, aryl($C_1$-$C_{20}$)alkyl, aryl($C_1$-$C_{20}$)alkoxy, aryloxy, aryloxy($C_1$-$C_{20}$)alkyl, aryloxy($C_1$-$C_{20}$)alkoxy, mono- or di($C_1$-$C_{20}$)alkylaryl($C_1$-$C_{20}$)alkyl, mono- or di-($C_1$-$C_{20}$)alkoxyaryl($C_1$-$C_{20}$)alkyl, mono- or di-($C_1$-$C_{20}$)alkylaryl($C_1$-$C_{20}$)alkoxy, mono- or di-($C_1$-$C_{20}$)alkoxyaryl($C_1$-$C_{20}$)alkoxy, amino, mono- or di-($C_1$-$C_{20}$)alkylamino, diarylamino, piperazino, N—($C_1$-$C_{20}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{20}$ alkyl, $C_1$-$C_{20}$ haloalkyl, $C_1$-$C_{20}$ alkoxy, mono($C_1$-$C_{20}$)alkoxy($C_1$-$C_{20}$)alkyl, acryloxy, methacryloxy, or halogen.

Each of the phenyl, aryl and heteroaromatic substituents (of B and B') are each independently, with some further embodiments: (b) an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of the substituents being $C_1$-$C_{20}$ alkyl, $C_1$-$C_{20}$ alkoxy, phenyl, or halogen.

Each of the phenyl, aryl and heteroaromatic substituents (of B and B') are each independently, with some additional embodiments, (c) a group represented by one of the following Formulas (D) and (E):

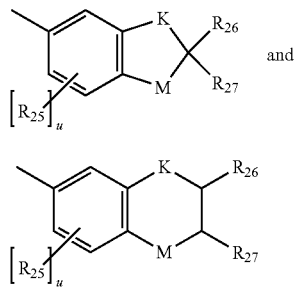

With reference to Formulas (D) and (E), each K is independently —$CH_2$— or —O—, and each M is independently —O— or substituted nitrogen, provided that when M is substituted nitrogen, K is —$CH_2$—, the substituted nitrogen substituents being hydrogen, $C_1$-$C_{20}$ alkyl, or $C_1$-$C_{20}$ acyl, each $R_{25}$ being independently chosen for each occurrence from $C_1$-$C_{20}$ alkyl, $C_1$-$C_{20}$ alkoxy, hydroxy, and halogen, $R_{26}$ and $R_{27}$ each being independently hydrogen or $C_1$-$C_{20}$ alkyl, and u is an integer ranging from 0 to 2.

Each of the phenyl, aryl and heteroaromatic substituents (of B and B') are each independently, with some additional further embodiments, (d) a group represented by the following Formula (F):

With reference to Formula (F), $R_{28}$ is hydrogen or $C_1$-$C_{20}$ alkyl, and $R_{29}$ is an unsubstituted, mono-, or di-substituted group chosen from naphthyl, phenyl, furanyl, and thienyl, wherein the substituents are $C_1$-$C_{20}$ alkyl, $C_1$-$C_{20}$ alkoxy, or halogen.

With some alternative embodiments, B and B', of Formula (I), taken together form one of a fluoren-9-ylidene, mono-, or di-substituted fluoren-9-ylidene, each of the fluoren-9-ylidene substituents being independently chosen from $C_1$-$C_{20}$ alkyl, $C_1$-$C_{20}$ alkoxy, and halogen.

In accordance with some embodiments of the present invention, B and B', of Formula (I), are in each case independently selected from: unsubstituted aryl; aryl substituted with linear or branched $C_1$-$C_6$ alkoxy; aryl substituted with linear or branched $C_1$-$C_6$ perhaloalkyl; aryl substituted with morpholino; and aryl substituted with piperidino.

With some additional embodiments of the present invention, B and B', of Formula (I), are in each case independently selected from: unsubstituted phenyl; phenyl substituted with linear or branched $C_1$-$C_6$ alkoxy; phenyl substituted with linear or branched $C_1$-$C_6$ perhaloalkyl; phenyl substituted with morpholino; and phenyl substituted with piperidino.

With the photochromic compounds of the present invention, such as represented by Formula (I), and in accordance with some embodiments, independently for each group $Y^1$, $Y^2$, and $Y^3$, each cyclic ester monomer, of each ring-opened cyclic ester monomer, is independently represented by the following Formula (A):

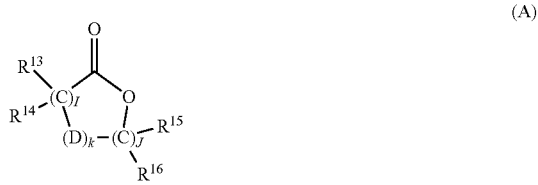

With reference to Formula (A), I and J are each independently integers ranging from 1 to 8; $R^{13}$, $R^{14}$, $R^{15}$, and $R^{16}$ are independently chosen for each carbon unit $(C)_I$ and $(C)_J$ from —H and C1-C16 alkyl; k is 0 or 1; and D is —O— when k is 1.

With the photochromic compounds of the present invention, such as represented by Formula (I), and in accordance with some embodiments, independently for each group $Y^1$, $Y^2$, and $Y^3$, each cyclic ester monomer, of each ring-opened cyclic ester monomer, is independently selected from, ε(epsilon)-caprolactone; ζ(zeta)-enantholactone; δ(delta)-valerolactone; a monoalkyl δ(delta)-valerolactone; a monoalkyl-, dialkyl-, or trialkyl-ε(epsilon)-caprolactone; β(beta)-lactones; γ(gamma)-lactones; dilactones; and ketodioxanones. Examples of monoalkyl-, dialkyl-, or trialkyl-ε(epsilon)-caprolactones include, but are not limited to: monomethyl-, monoethyl-, monohexyl-, dimethyl-, di-n-propyl-, mono-/di-/tri-t(tertiary)-butyl-, di-n-hexyl-, trimethyl-, and triethyl-, ε(epsilon)-caprolactones; 5-nonyl-oxepan-2-one; 4,4,6- or 4,6,6-trimethyl-oxepan-2-one; and 5-hydroxymethyl-oxepan-2-one. Examples of β(beta)-lactones include, but are not limited to: β(beta)-propiolactone; and β(beta)-butyrolactone. Examples of γ(gamma)-lactones include, but are not limited to: γ(gamma)-butyrolactone; and pivalolactone.

With the photochromic compounds of the present invention, such as represented by Formula (I), and in accordance with some embodiments, independently for each group $Y^1$, $Y^2$, and $Y^3$, each cyclic carbonate monomer, of each ring-opened cyclic carbonate monomer, is independently represented by the following Formula (B),

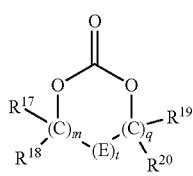

(B)

With reference to Formula (B), m and q are each independently integers ranging from 1 to 3; $R^{17}$, $R^{18}$, $R^{19}$, and $R^{20}$ are each independently chosen for each carbon unit $(C)_m$ and $(C)_q$ from —H and C1-C16 alkyl; t is 0 or 1; and E is —O— when t is 1.

With the photochromic compounds of the present invention, such as represented by Formula (I), and in accordance with some embodiments, independently for each group $Y^1$, $Y^2$, and $Y^3$, each cyclic carbonate monomer, of each ring-opened cyclic carbonate monomer, is independently selected from, ethylene carbonate; 3-ethyl-3-hydroxylmethyl trimethylene carbonate; propylene caronate, trimethylene carbonate; trimethylolpropane monocarbonate; 4,6-dimethyl-1,3-propylene carbonate; 2,2-dimethyl trimethylene carbonate; and 1,2-dioxepan-2-one.

Each group $Y^1$, $Y^2$, and $Y^3$, with some embodiments, independently and optionally include at least one reactive substituent, which can be selected from those classes and examples of reactive substituents as described further herein, such as, but not limited to: active hydrogen groups (such as hydroxyl groups); and ethylenically unsaturated and radically polymerizable groups (such as vinyl groups and (meth)acryloyl groups). Each reactive substituent can independently be a pendent reactive substituent or a terminal reactive substituent.

With some further embodiments of the present invention, for each lengthening group $L^1$, $L^2$, and $L^3$ represented by Formula (II), (a) $Q_1$, $Q_2$, and $Q_3$ for each occurrence, are independently selected from unsubstituted aryl, substituted aryl, unsubstituted cycloalkyl, and substituted cycloalkyl.

In accordance with some further embodiments, and independently for each group $L^1$, $L^2$, and $L^3$ represented by Formula (II), (b) each $S_1$, $S_2$, $S_3$, $S_4$, and $S_5$ is independently chosen for each occurrence from a spacer unit selected from (ii) or (iii) as described as follows. Each $S_1$, $S_2$, $S_3$, $S_4$, and $S_5$ of Formula (II), with some embodiments, is independently chosen for each occurrence from a spacer unit selected from, (ii) —N(Z)—, —C(Z)=C(Z)—, —C(Z)=N—, —C(Z')$_2$—C(Z)$_2$—, —N(Z)—C(Z')$_2$—, and a single bond, wherein Z for each occurrence is independently selected from hydrogen, $C_1$-$C_8$ alkyl, $C_3$-$C_6$ cycloalkyl and aryl, and Z' for each occurrence is independently selected from $C_1$-$C_8$ alkyl, $C_3$-$C_6$ cycloalkyl and aryl. Each $S_1$, $S_2$, $S_3$, $S_4$, and $S_5$ of Formula (II), with some further embodiments, is independently chosen for each occurrence from a spacer unit selected from, (iii) —O—, —C(=O)—, —C≡C—, —N=N—, —S—, —S(=O)—, and straight-chain or branched $C_1$-$C_{12}$ alkylene residue, the $C_1$-$C_{12}$ alkylene residue being unsubstituted, mono-substituted by cyano or halogen, or poly-substituted by halogen.

In accordance with some additional embodiments, independently for each group $L^1$, $L^2$, and $L^3$ represented by Formula (II), (c) P for each occurrence is independently selected from hydrogen, hydroxy, amino, $C_2$-$C_8$ alkenyl, $C_2$-$C_8$ alkynyl, acryloyloxy, methacryloyloxy, 2-(acryloyloxy)ethylcarbamyl, 2-(methacryloyloxy)ethylcarbamyl, epoxy, carboxylic acid, carboxylic ester, acryloylamino, methacryloylamino, aminocarbonyl, $C_1$-$C_8$ alkyl aminocarbonyl, aminocarbonyl($C_1$-$C_8$)alkyl, $C_1$-$C_8$ alkyloxycarbonyloxy, halocarbonyl, aryl, hydroxy($C_1$-$C_8$)alkyl, $C_1$-$C_8$ alkyl, $C_1$-$C_8$ alkoxy, amino($C_1$-$C_8$)alkyl, $C_1$-$C_8$ alkylamino, di-($C_1$-$C_8$)alkylamino, $C_1$-$C_8$ alkyl($C_1$-$C_8$)alkoxy, $C_1$-$C_8$ alkoxy($C_1$-$C_8$)alkoxy, nitro, poly($C_1$-$C_8$)alkyl ether, ($C_1$-$C_8$) alkyl($C_1$-$C_8$)alkoxy($C_1$-$C_8$)alkyl, polyethyleneoxy, polypropyleneoxy, ethylene, acryloyl, acryloyloxy($C_1$-$C_{18}$)alkyl, methacryloyl, methacryloyloxy($C_1$-$C_8$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, and vinyl ester.

In accordance with some further additional embodiments, independently for each group $L^1$, $L^2$, and $L^3$ represented by Formula (II), (b) each $S_1$, $S_2$, $S_3$, $S_4$, and $S_5$ is independently chosen for each occurrence from a spacer unit selected from: (ii) —N(Z)—, —C(Z)=C(Z)—, and a single bond, wherein Z for each occurrence is independently selected from hydrogen, $C_1$-$C_8$ alkyl, $C_3$-$C_6$ cycloalkyl and aryl, and Z' for each occurrence is independently selected from $C_1$-$C_8$ alkyl, $C_3$-$C_6$ cycloalkyl and aryl; and (iii) —O—, —C(=O)—, —C≡C—, and straight-chain or branched $C_1$-$C_6$ alkylene residue, the $C_1$-$C_6$ alkylene residue being unsubstituted, mono-substituted by cyano or halogen, or poly-substituted by halogen.

In accordance with some additional further embodiments, independently for each group $L^1$, $L^2$, and $L^3$ represented by Formula (II), (c) P for each occurrence is independently selected from hydrogen, hydroxy, amino, $C_2$-$C_8$ alkenyl, $C_2$-$C_8$ alkynyl, and aryl.

With the photochromic compounds in accordance with some embodiments of the present invention, and with reference to Formula (I), at least one of $R^6$ and $R^7$ is selected from lengthening group $L^1$, or —OR$^c$, where R$^c$ is lengthening group $L^2$.

With reference to Formula (I), with the photochromic compounds according to some embodiments of the present invention, $R^6$ and $R^7$ are each independently selected from lengthening group $L^1$ and —OR$^c$, where R$^c$ is lengthening group $L^2$.

With further reference to Formula (I), with the photochromic compounds according to some embodiments of the present invention: $R^6$ is selected from lengthening group $L^1$ and —OR$^c$, where R$^c$ is lengthening group $L^2$; and $R^7$ is halogen (such as fluoro, chloro, or bromo).

With the photochromic compounds according to some embodiments of the present invention, and with reference to Formula (I), $R^3$ at position-11 is selected from, halogen (such as fluoro, chloro, or bromo), —CN, linear or branched $C_1$-$C_8$ perhaloalkyl, unsubstituted phenyl, and phenyl substituted with halogen and/or linear or branched $C_1$-$C_8$ perhaloalkyl.

With the photochromic compounds according to some embodiments of the present invention, and with reference to Formula (I), $R^3$ at position-12 is lengthening group $L^3$.

With the photochromic compounds according to some further embodiments of the present invention, and with reference to Formula (I), $R^3$ at position-11 is halogen (such as fluoro, chloro, or bromo).

Each lengthening group $L^1$, $L^2$, and $L^3$ of the photochromic compounds of the present invention, such as represented by Formula (I), is in each case independently selected from, with some embodiments:

L(1) 4-[4-(4-butyl-cyclohexyl)-phenyl]-cyclohexyloxy

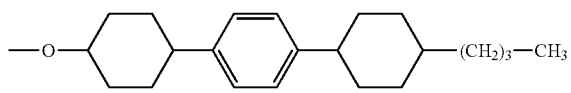

L(2) 4"-butyl-[1,1';4',1"]tercyclohexan-4-yloxy

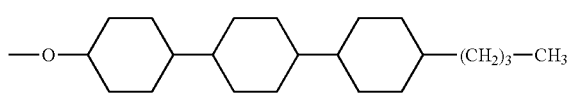

L(3) 4-[4-(4-butyl-phenyl)-cyclohexyloxycarbonyl]-phenoxy

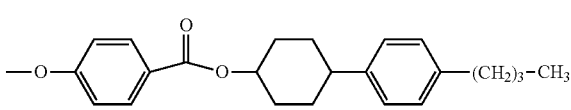

L(4) 4'-(4-butyl-benzoyloxy)-biphenyl-4-carbonyloxy

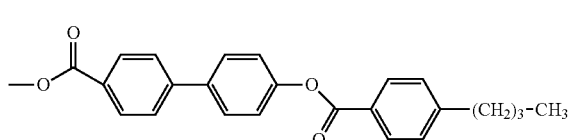

L(5) 4-(4-pentyl-phenylazo)-phenylcarbamoyl

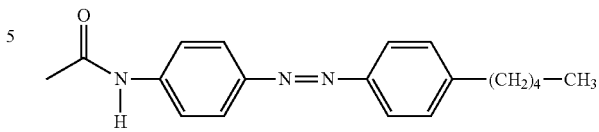

L(6) 4-(4-dimethylamino-phenylazo)-phenylcarbamoyl

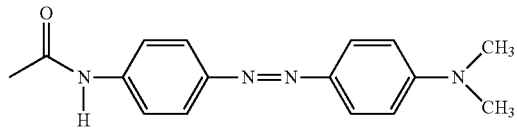 [SMILES: CC(=O)Nc1ccc(N=Nc2ccc(N(C)C)cc2)cc1]

L(7) {4-[5-(4-propyl-benzoyloxy)-pyrimidin-2-yl]-phenyl} ester

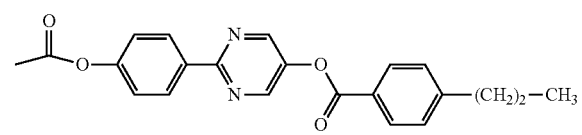

L(8) {4-[2-(4'-methyl-biphenyl-4-carbonyloxy)-1,2-diphenyl-ethoxycarbonyl]-phenyl} ester

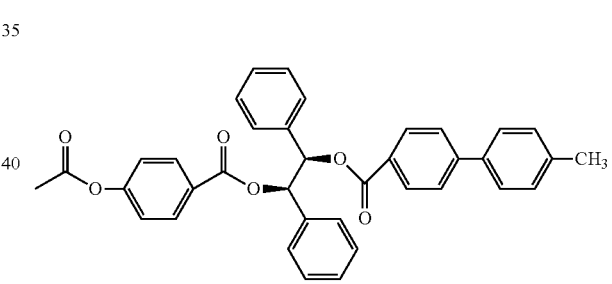

L(9) [4-(1,2-diphenyl-2-{3-[4-(4-propyl-benzoyloxy)-phenyl]-acryloyloxy}-ethoxycarbonyl)-phenyl] ester

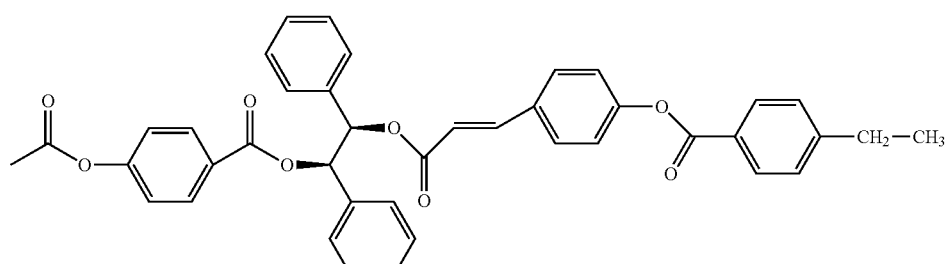

L(10) 4-[4-(4-{4-[3-(6-{4-[4-(4-nonyl-benzoyloxy)-phenoxycarbonyl]-phenoxy}-hexyloxycarbonyl)-propionyloxy]-benzoyloxy}-benzoyloxy)-phenyl]-piperazin-1-yl

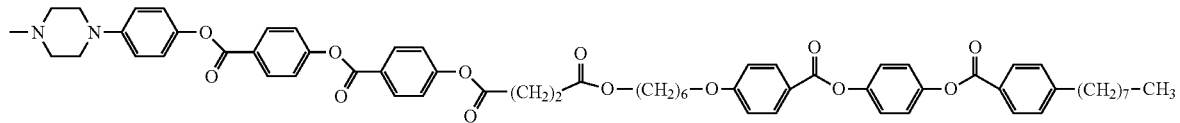

L(11) {4-[4-(4-{4-[4-(4-nonyl-benzoyloxy)-benzoyloxy]-benzoyloxy}-benzoyloxy)-phenyl]-piperazin-1-yl}

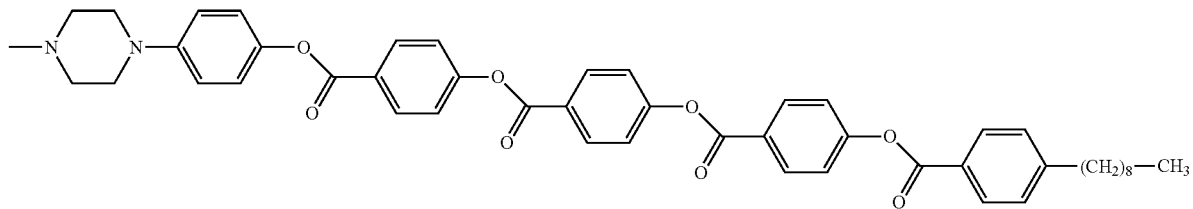

L(12) 4-(4'-propyl-biphenyl-4-ylethynyl)-phenyl

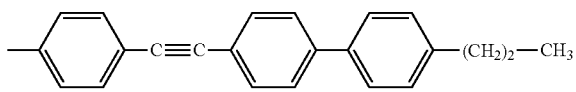

L(13) 4-(4-fluoro-phenoxycarbonyloxy)-piperidin-1-yl

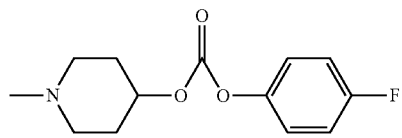 [SMILES: CN1CCC(OC(=O)Oc2ccc(F)cc2)CC1]

L(14) 2-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxy]-indan-5-yl

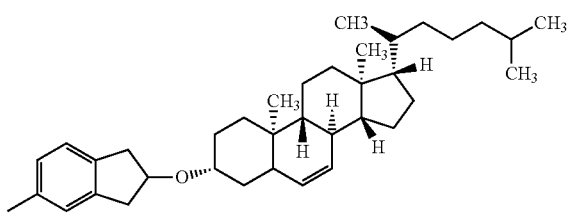

L(15) 4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl

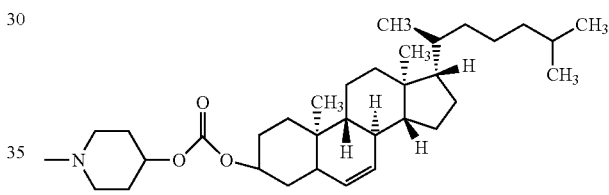

L(16) 4-(biphenyl-4-carbonyloxy)-piperidin-1-yl

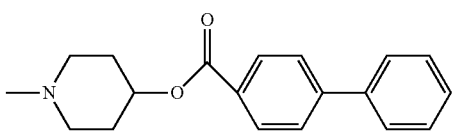

L(17) 4-(naphthalene-2-carbonyloxy)-piperidin-1-yl

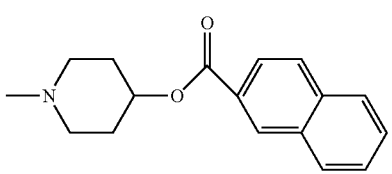 [SMILES: CN1CCC(OC(=O)c2ccc3ccccc3c2)CC1]

L(18) 4-(4-phenylcarbamoyl-phenylcarbamoyl)-piperidin-1-yl

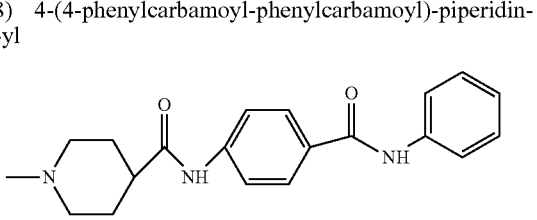

L(19) 4-(4-(4-phenylpiperidin-1-yl)-benzoyloxy)-piperidin-1-yl

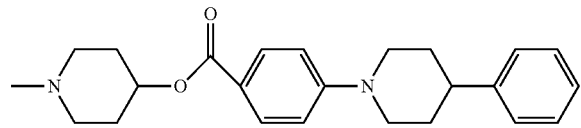 [SMILES: CN1CCC(OC(=O)c2ccc(N3CCC(c4ccccc4)CC3)cc2)CC1]

L(20) 4-butyl-[1,1';4',1"]terphenyl-4-yl

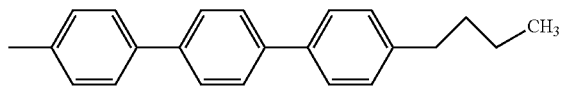

L(21) 4-(4-pentadecafluoroheptyloxy-phenylcarbamoyl)-benzyloxy

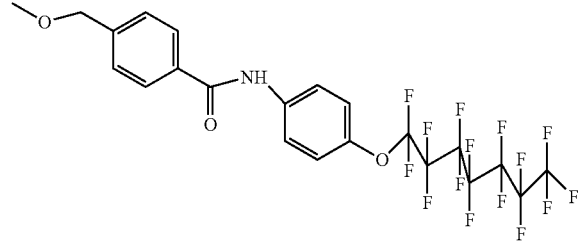 [SMILES: COCc1ccc(C(=O)Nc2ccc(OC(F)(F)C(F)(F)C(F)(F)C(F)(F)C(F)(F)C(F)(F)C(F)(F)F)cc2)cc1]

L(22) 4-(4-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-benzoyloxy}-phenoxycarbonyl)-phenoxymethyl

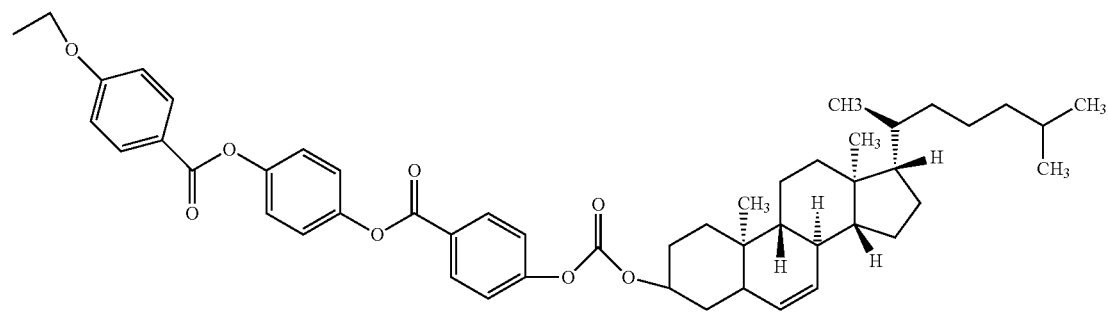

L(23) 4-[4-(4-cyclohexyl-phenylcarbamoyl)-benzyloxy]-piperidin-1-yl

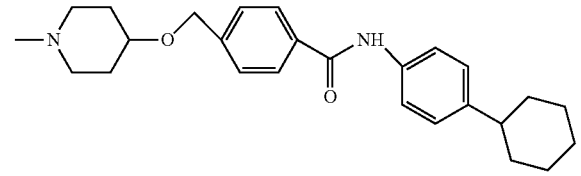 [SMILES: CN1CCC(OCc2ccc(C(=O)Nc3ccc(C4CCCCC4)cc3)cc2)CC1]

L(24) 4-[4-(4-cyclohexyl-phenylcarbamoyl)-benzyloxy]-piperidin-1-yl

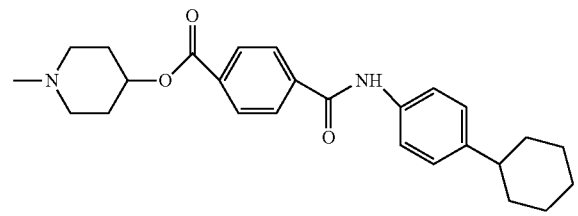 [SMILES: CN1CCC(OC(=O)c2ccc(C(=O)Nc3ccc(C4CCCCC4)cc3)cc2)CC1]

L(25) N-{4-[(4-pentyl-benzylidene)-amino]-phenyl}-acetamidyl

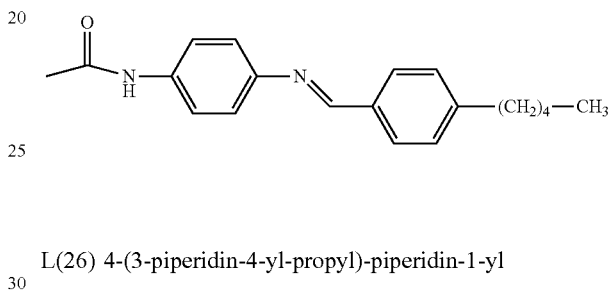

L(26) 4-(3-piperidin-4-yl-propyl)-piperidin-1-yl

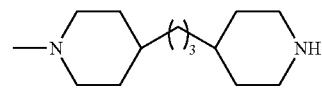

L(27) 4-(4-hexyloxy-benzoyloxy)-piperidin-1-yl]

L(28) 4-(4'-hexyloxy-biphenyl-4-carbonyloxy)-piperidin-1-yl

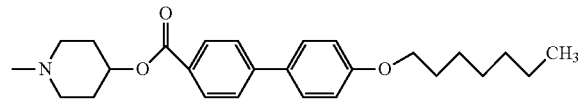 [SMILES: CCCCCCCOc1ccc(-c2ccc(C(=O)OC3CCN(C)CC3)cc2)cc1]

L(29) 4-(4-butyl-phenylcarbamoyl)-piperidin-1-yl

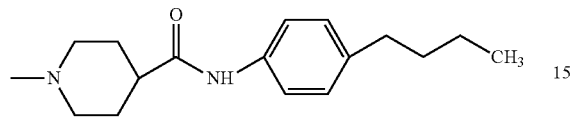

L(30a) 1-methyl-4-((4'-(((1-methylpiperidin-4-yl)oxy)carbonyl)-[1,1'-biphenyl]-4-carbonyl)oxy)piperidin-1-yl

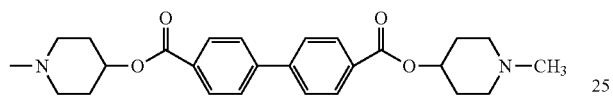

L(30b) bis(1-yl-piperidin-4-yl)[1,1'-biphenyl]-4,4'-dicarboxylate

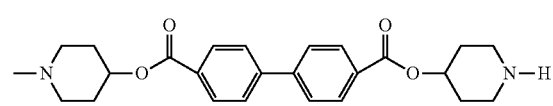 [SMILES: CN1CCC(OC(=O)c2ccc(-c3ccc(C(=O)OC4CCNCC4)cc3)cc2)CC1]

L(31) 4-(4-(9-(4-butylphenyl)-2,4,8,10-tetraoxaspiro[5.5]undec-3-yl)phenyl)piperazin-1-yl

L(32) 4-(6-(4-butylphenyl)carbonyloxy-(4,8-dioxabicyclo[3.3.0]oct-2-yl))oxycarbonyl)phenyl

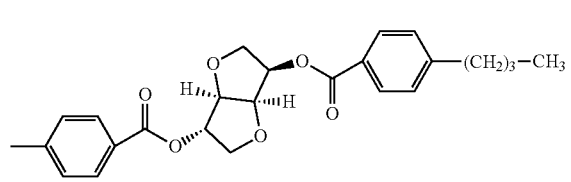

L(33) 1-{4-[5-(4-butyl-phenyl)-[1,3]dioxan-2-yl]-phenyl}-4-methyl-piperazin-1-yl

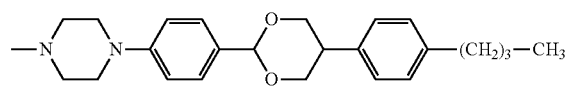

L(34) 4-(7-(4-propylphenylcarbonyloxy)bicyclo[3.3.0]oct-2-yl)oxycarbonyl)phenyl

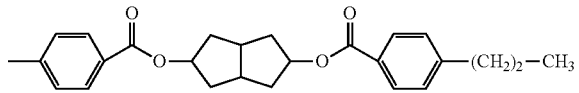

L(35) 4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy

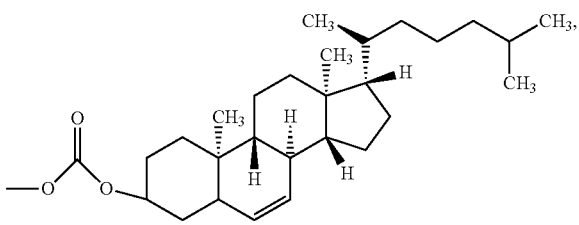

L(a)
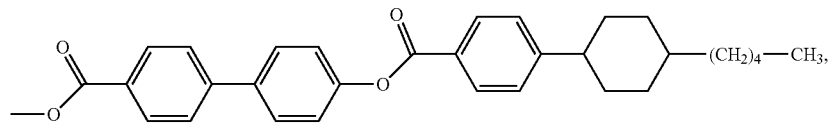
L(b)
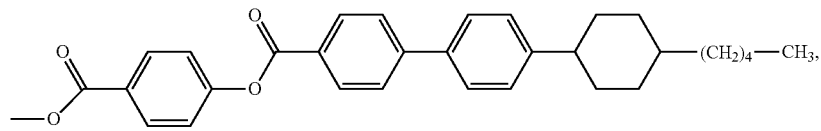
L(c)
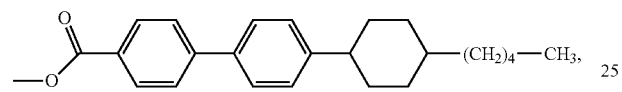
L(d)
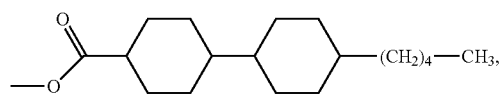
L(e)
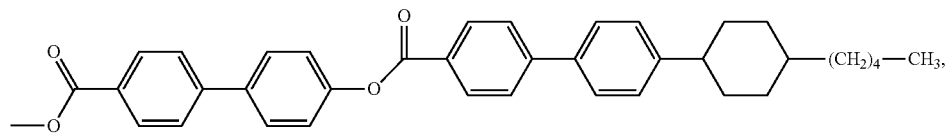
L(f)
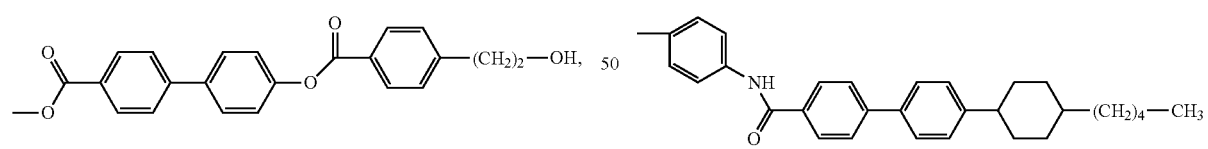
L(g)
L(h)
L(i)
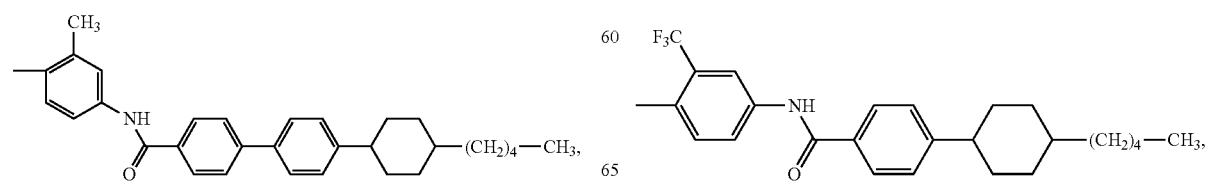

L(j)
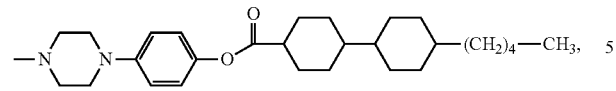
L(k)
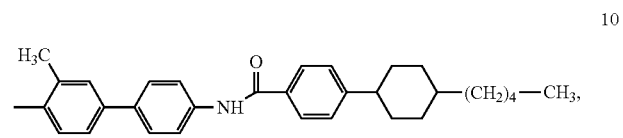
L(l)
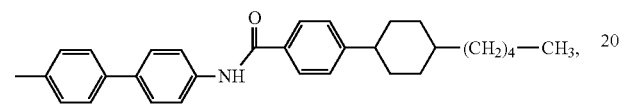
L(m)
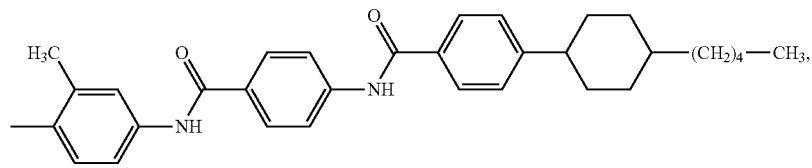
L(n)
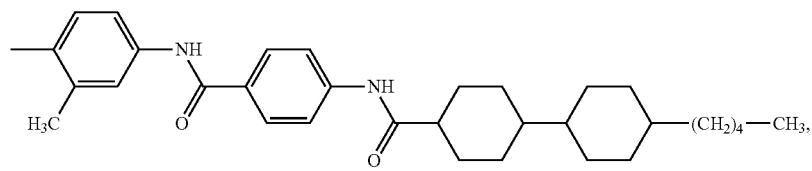
L(o)
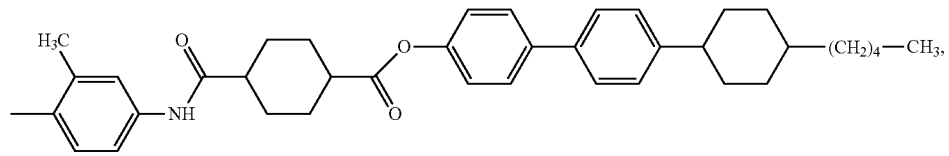
L(p)
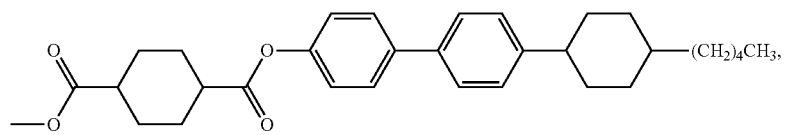

L(q)
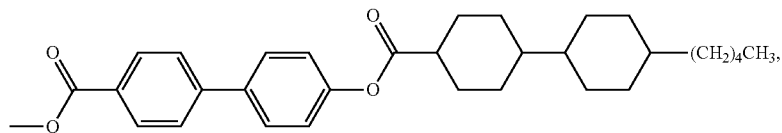
L(r)
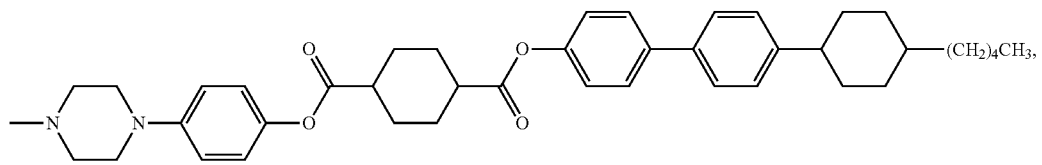
L(s)
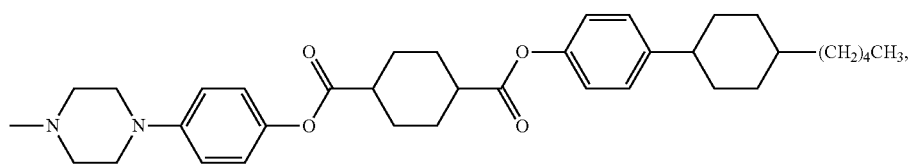
L(t)
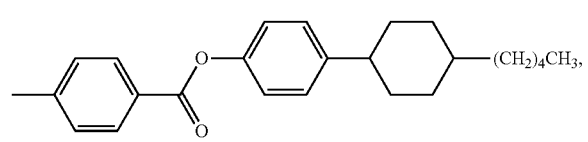
L(x)
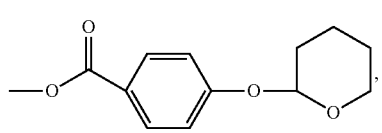
L(u)
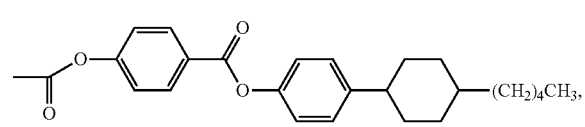
L(y)
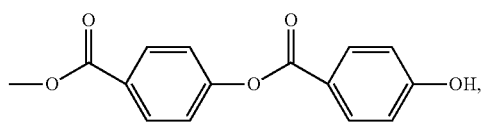 [SMILES: COC(=O)c1ccc(OC(=O)c2ccc(O)cc2)cc1]
L(v)
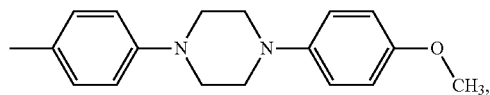
L(z)
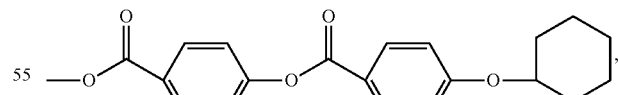
L(w)
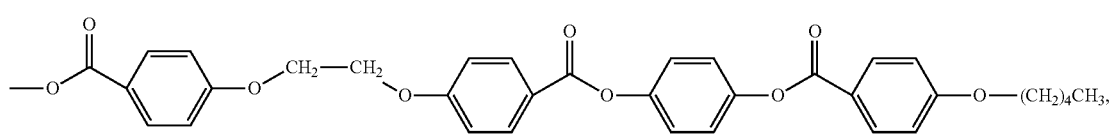

L(aa)

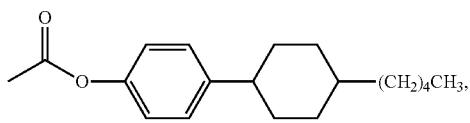

L(ab)

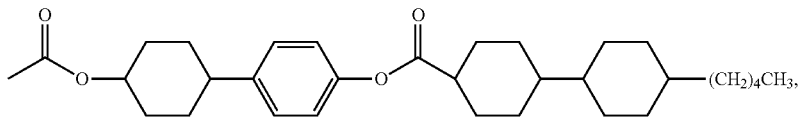

L(ac)

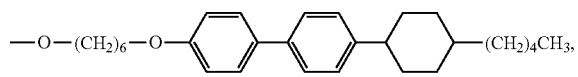

L(ad)

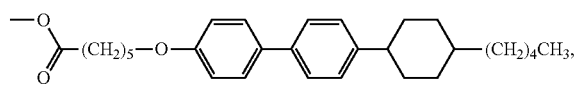

L-DC-(a) (4-trans-(4-pentylcyclohexyl)benzamido)phenyl,
L-DC-(b) (4-(4-trans-(4-pentylcyclohexyl)phenoxy)carbonyl) phenyl,
L-DC-(c) 4-(4-(4-trans-(4-pentylcyclohexyl)phenyl)benzamido) phenyl,
L-DC-(d) 4-((trans-(4'-pentyl-[1,1'-bi(cyclohexan)]-4-yl)oxy)carbonyl)phenyl,
L-DC-(e) 4-(4'-(4-pentylcyclohexyl)-[1,1'-biphenyl]-4-yl-carboxamido)phenyl,
L-DC-(f) 4-((4'-(4-pentylcyclohexyl)-[1,1'-biphenyl]-4-carbonyl)oxy)benzamido,
L-DC-(g) 4-(4'-(4-pentylcyclohexyl)-[1,1'-biphenyl]-4-carbonyl)piperazin-1-yl,
L-DC-(h) 4-(4-(4-trans-(4-pentylcyclohexyl) phenyl)benzamido)-2-(trifluoromethyl)phenyl,
L-DC-(i) 2-methyl-4-trans-(4-((4'-trans-(4-pentylcyclohexyl)biphenyl-4-yloxy)carbonyl)cyclohexanecarboxamido)phenyl,
L-DC-(j) 4'-(4'-pentylbi(cyclohexane-4-)carbonyloxy)biphenylcarbonyloxy,
L-DC-(k) 4-(((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)carbonyl)piperazin-1-yl, and
L-DC-(l) 4-((S)-2-methylbutoxy)phenyl)-10-(4-(((3R,3aS,6S,6aS)-6-(4'-trans-(4-pentylcyclohexyl)biphenylcarbonyloxy)hexahydrofuro[3,2-b]furan-3-yloxy)carbonyl) phenyl.

In accordance with some embodiments of the present invention, with —$OR^c$ where $R^c$ is lengthening group $L^2$, the bond between —O and lengthening group $L^2$ is free of two heteroatoms linked to each other.

In accordance with some embodiments, the photochromic compounds of the present invention, such as represented by Formula (I), after formation thereof, can be subjected to one or more additional chemical reactions for purposes of modifying at least one of $R^1$, $R^3$, $R^6$, and $R^7$, so as to be converted to or to be substituted with a lengthening group $L^1$, $L^2$, or $L^3$, as the case may be, and in each case as described previously herein with reference to Formula (II). Examples of additional chemical reactions that the photochromic compound(s) represented by Formula (I) can be subjected to include, but are not limited to, palladium-catalyzed cross couplings, etherifications, esterifications, amidations, and condensations.

The present invention also provides, with some embodiments, a photochromic compound represented by the following Formula (III), $$L^y\text{-}(PC)_{n'} \qquad \text{Formula (III)}$$

With reference to Formula (III), n' is at least 2, such as from 2 to 100, or from 2 to 50, or from 2 to 25, or from 2 to 20, or from 2 to 15, or from 2 to 10, or from 2 to 8, or from 2 to 5, or from 2 to 4, or 2 or 3, in each case inclusive of the recited values.

With further reference to Formula (III), the PC group or moiety, independently for each n', is a residue of a photochromic compound according to the present invention, such as represented by Formula (I), and as described previously herein.

With additional reference to Formula (III), $L^y$ is a multivalent linking group selected from: (i) a first multivalent compound that is a multivalent polymer; and (ii) a second multivalent compound that is different than the first multivalent compound, the second multivalent compound being non-polymeric and comprising a residue selected from, a residue of a polyisocyanate, a residue of a polyol, a residue of a polycarboxylic acid, a residue of a polycarbonate functional material, and combinations thereof. As used herein, the term "non-polymeric" with regard to the second multivalent compound, from which $L^y$ of Formula (III) can be selected, means it is free of repeating monomer units (or repeating monomer residues).

In accordance with some embodiments, and with further reference to Formula (III), the multivalent polymer of the first multivalent compound, from which $L^y$ can be selected, is selected from multivalent polyurethane, multivalent polyester, multivalent polyether, multivalent poly(meth)acrylate, multivalent polyvinylalcohol, multivalent polycarbonate, multivalent polysiloxane, and multivalent cyclic polysiloxane. The multivalent polymers from which $L^y$ can be selected can be prepared in accordance with art-recognized methods from art-recognized materials including, but not limited to, art-recognized monomers. With some embodiments, (a) at least some of the monomers from which the polymer is prepared (and of which $L^y$ is a residue) have covalently bonded thereto one or more photochromic compounds according to the present invention; and/or (b) the resulting polymer (of which $L^y$ is a residue) is subsequently modified to include photochromic compounds according to the present invention bonded thereto. The multivalent polymers from which L$^y$ can be selected can, with some embodiments, have any suitable backbone architecture, such as but not limited to, alternating backbone architecture, block backbone architecture, random backbone architecture, and combinations thereof. The multivalent polymers from which L$^y$ can be selected can, with some further embodiments, have any suitable macro polymer architecture, such as but not limited to, linear polymer architecture, branched polymer architecture, comb polymer architecture, star polymer architecture, dendritic polymer architecture, and combinations thereof.

Classes of polyisocyanates that can be a residue of the second multivalent compound, from which L$^y$ of Formula (III) can be selected, include, but are not limited to, aliphatic polyisocyanates, aromatic polyisocyanates, cycloaliphatic polyisocyanates, and heterocyclic polyisocyanates, in each case having at least 2 isocyanate groups, dimers of such polyisocyanates, trimers of such polyisocyanates, and mixtures of such polyisocyanates. Examples of polyisocyanates that can be a residue of the second multivalent compound, from which L$^y$ of Formula (III) can be selected, include, but are not limited to, toluene-2,4-diisocyanate; toluene-2,6-diisocyanate; diphenyl methane-4,4'-diisocyanate; diphenyl methane-2,4'-diisocyanate; para-phenylene diisocyanate; biphenyl diisocyanate; 3,3'-dimethyl-4,4'-diphenylene diisocyanate; tetramethylene-1,4-diisocyanate; hexamethylene-1,6-diisocyanate; 2,2,4-trimethyl hexane-1,6-diisocyanate; lysine methyl ester diisocyanate; bis(isocyanato ethyl)fumarate; isophorone diisocyanate; ethylene diisocyanate; dodecane-1,12-diisocyanate; cyclobutane-1,3-diisocyanate; cyclohexane-1,3-diisocyanate; cyclohexane-1,4-diisocyanate; methyl cyclohexyl diisocyanate; hexahydrotoluene-2,4-diisocyanate; hexahydrotoluene-2,6-diisocyanate; hexahydrophenylene-1,3-diisocyanate; hexahydrophenylene-1,4-diisocyanate; perhydrodiphenylmethane-2,4'-diisocyanate; perhydrodiphenylmethane-4,4'-diisocyanate, dimers thereof, trimers thereof, and mixtures thereof.

Classes of polyols that can be a residue of the second multivalent compound, from which L$^y$ of Formula (III) can be selected, include, but are not limited to, aliphatic polyols, aromatic polyols, cycloaliphatic polyols, and heterocyclic polyols, in each case having at least 2 hydroxyl groups. Examples of polyols that can be a residue of the second multivalent compound, from which L$^y$ of Formula (III) can be selected, include, but are not limited to, trimethylolpropane, di(trimethylolpropane), trimethylolethane, di(trimethylolethane), trishydroxyethylisocyanurate, pentaerythritol, di(pentaerythritol) ethylene glycol, propylene glycol, trimethylene glycol, butanediol, heptanediol, hexanediol, octanediol, 4,4'-(propane-2,2-diyl)dicyclohexanol, 4,4'-methylenedicyclohexanol, neopentyl glycol, 2,2,3-trimethylpentane-1,3-diol, 1,4-dimethylolcyclohexane, 2,2,4-trimethylpentane diol, 4,4'-(propane-2,2-diyl)diphenol, and 4,4'-methylenediphenol.

Classes of polycarboxylic acids that can be a residue of the second multivalent compound, from which L$^y$ of Formula (III) can be selected, include, but are not limited to, aliphatic polycarboxylic acids, aromatic polycarboxylic acids, cycloaliphatic polycarboxylic acids, and heterocyclic polycarboxylic acids, in each case having at least 2 carboxylic acid groups and/or carboxylic acid ester groups. Examples of polycarboxylic acids that can be a residue of the second multivalent compound, from which L$^y$ of Formula (III) can be selected, include, but are not limited to, benzene-1,2,4-tricarboxylic acid, phthalic acid, tetrahydrophthalic acid, hexahydrophthalic acid, endobicyclo-2,2,1,5-heptyne-2,3-dicarboxylic acid, tetrachlorophthalic acid, cyclohexanedioic acid, succinic acid, isophthalic acid, terephthalic acid, azelaic acid, maleic acid, trimesic acid, 3,6-dichlorophthalic acid, adipic acid, sebacic acid, and like multifunctional carboxylic acids.

Classes of polycarbonate functional materials/compounds that can be a residue of the second multivalent compound, from which L$^y$ of Formula (III) can be selected, include, but are not limited to, aliphatic polycarbonate functional compounds, aromatic polycarbonate functional compounds, cycloaliphatic polycarbonate functional compounds, and heterocyclic polycarbonate functional compounds, in each case having at least 2 cyclic carbonate groups. The polycarbonate functional compounds can be prepared in accordance with art-recognized methods. In accordance with some embodiments, the polycarbonate functional compounds are prepared by heating oxirane functional precursor materials in the presence of carbon dioxide and an appropriate catalyst, such as a tetraalkyl ammonium iodide and/or tetraalkyl ammonium bromide, for example, tetrabutylammonium iodide and/or tetrabutylammonium bromide. In accordance with some further embodiments, the oxirane functional precursor material is prepared by reacting one more of a polyol with at least two moles of epichlorohydrin, so as to convert at least two of the hydroxyl groups of the polyol to oxirane functional groups. The polyol can, with some embodiments, be selected from those classes and examples of polyols as recited previously herein with regard to L.

In accordance with some embodiments, and as discussed previously herein: R$^1$ independently for each n, and R$^3$, are in each case independently selected from a reactive substituent, or are each independently substituted with at least one reactive substituent; and B and B' are each independently an aryl group that is mono-substituted with a reactive substituent. If the photochromic compounds of the present invention include multiple reactive substituents, each reactive substituent can be independently chosen. Each reactive substituent, with some embodiments, independently is a terminal reactive substituent or a pendent reactive substituent.

Classes of reactive substituents from which each reactive substituent can be independently selected, include, but are not limited to: active hydrogen groups; groups that are reactive with active hydrogen groups; and ethylenically unsaturated and radically polymerizable groups. Examples of active hydrogen groups, from which each reactive substituent can be independently selected, include, but are not limited to: hydroxyl groups; thiol groups; carboxylic acid groups; sulfonic acid groups; primary amine groups; and secondary amine groups, including cyclic amine groups. Examples of groups that are reactive with active hydrogen groups, from which each reactive substituent can be independently selected, include, but are not limited to: isocyanate groups; isothiocyanate groups; oxirane (or epoxide) groups; thiirane (or thioepoxide) groups; aziridine groups; carboxylic acid ester groups; cyclic carboxylic acid ester groups; cyclic carboxylic acid anhydride groups; sulfonic acid ester groups; and cyclic carbonate groups. Examples of ethylenically unsaturated and radically polymerizable groups, from which each reactive substituent can be independently selected, include, but are not limited to: vinyl groups, including vinyl ether groups; halovinyl groups, such as 1-chlorovinyl; allyl groups, including allyl ether groups; acryl groups; and methacryl groups. Acryl groups and methacryl groups can be referred to collectively herein as (meth) acryl groups.

In accordance with some embodiments of the present invention, and for purposes of non-limiting illustration, further examples of ethylenically unsaturated and radically polymerizable groups, from which each reactive substituent can be independently selected, include, but are not limited to: acryl; methacryl; crotyl; 2-(methacryloxy)ethylcarbamyl; 2-(methacryloxy)ethoxycarbonyl; vinylphenyl, such as 4-vinylphenyl; vinyl; and 1-halovinyl, such as 1-chlorovinyl. As used herein, the terms acryloyl, methacryloyl, crotyl, 2-(methacryloxy)ethylcarbamyl, 2-(methacryloxy)ethoxycarbonyl, vinylphenyl, vinyl, and 1-halovinyl, refer to the following representative structures:

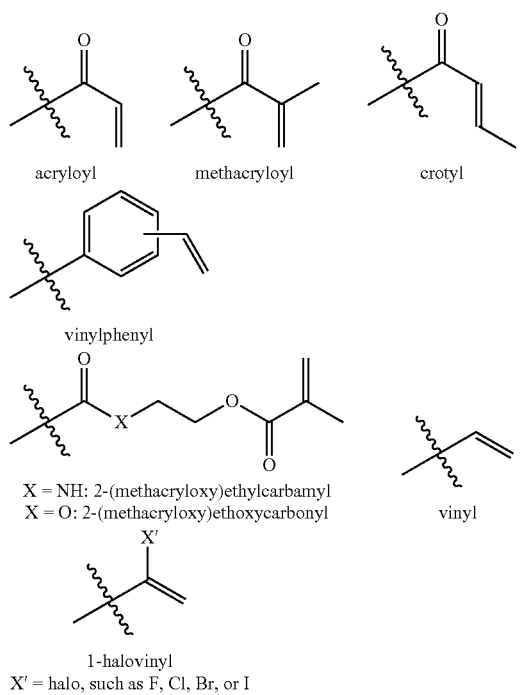

A further description of reactive substituents that can be used in connection with the photochromic compounds of the present invention is provided at column 28, line 34 through column 33, line 49 of U.S. Pat. No. 9,028,728 B2, which disclosure is hereby specifically incorporated by reference herein.

With some embodiments, the photochromic compounds of the present invention, such as described with reference to Formula (I), can each be used alone, or in combination with one or more other photochromic compounds. For example, the photochromic compounds of the present invention can be used in conjunction with one or more other photochromic compounds having activated absorption maxima within the range of 300 to 1000 nanometers. Further, the photochromic compounds according to the present invention can be used in conjunction with one or more complementary conventional polymerizable or compatiblized photochromic compounds, such as for example, those disclosed in U.S. Pat. No. 6,113,814 (at col. 2, line 39 to col. 8, line 41), and U.S. Pat. No. 6,555,028 (at col. 2, line 65 to col. 12, line 56), which disclosures are hereby specifically incorporated by reference herein.

The photochromic compounds of the present invention can be used in combination with a mixture of other photochromic compounds. For example, although not limiting herein, mixtures of photochromic compounds can be used to attain certain activated colors, such as a near neutral gray or near neutral brown. See, for example, U.S. Pat. No. 5,645,767, col. 12, line 66 to col. 13, line 19, which describes the parameters that define neutral gray and brown colors and which disclosure is specifically incorporated by reference herein.

Examples of classes of other photochromic compounds that can be used in combination with the photochromic compounds of the present invention, include, but are not limited to, indeno-fused naphthopyrans, naphtho[1,2-b]pyrans, naphtho[2,1-b]pyrans, spirofluoroeno[1,2-b]pyrans, phenanthrenopyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, thermally reversible photochromic compounds, and non-thermally reversible photochromic compounds, and mixtures thereof.

Non-limiting examples of photochromic pyrans that can be used in combination with the photochromic compounds of the present invention, include, but are not limited to, benzopyrans, naphthopyrans, e.g., naphtho[1,2-b]pyrans, naphtho[2,1-b]pyrans, indeno-fused naphthopyrans, such as those disclosed in U.S. Pat. No. 5,645,767, and heterocyclic-fused naphthopyrans, such as those disclosed in U.S. Pat. Nos. 5,723,072, 5,698,141, 6,153,126, and 6,022,497, which are hereby incorporated by reference; spiro-9-fluoreno[1,2-b]pyrans; phenanthrenopyrans; quinopyrans; fluoroanthenopyrans; spiropyrans, e.g., spiro(benzindoline)naphthopyrans, spiro(indoline)benzopyrans, spiro(indoline)naphthopyrans, spiro(indoline)quinopyrans and spiro(indoline)pyrans. Further examples of naphthopyrans and complementary organic photochromic compounds are described in U.S. Pat. No. 5,658,501, which are hereby specifically incorporated by reference herein. Spiro(indoline)pyrans are also described in the text, *Techniques in Chemistry*, Volume III, "Photochromism", Chapter 3, Glenn H. Brown, Editor, John Wiley and Sons, Inc., New York, 1971, which is hereby incorporated by reference.

Non-limiting examples of photochromic oxazines that can be used in combination with the photochromic compounds of the present invention, include, but are not limited to, benzoxazines, naphthoxazines, and spiro-oxazines, e.g., spiro(indoline)naphthoxazines, spiro(indoline)pyridobenzoxazines, spiro(benzindoline)pyridobenzoxazines, spiro(benzindoline)naphthoxazines, spiro(indoline)benzoxazines, spiro(indoline)fluoranthenoxazine, and spiro(indoline)quinoxazine. Non-limiting examples of photochromic fulgides that can be used in combination with the photochromic compounds of the present invention, include, but are not limited to: fulgimides, and the 3-furyl and 3-thienyl fulgides and fulgimides, which are disclosed in U.S. Pat. No. 4,931,220 (which are hereby specifically incorporated by reference) and mixtures of any of the aforementioned photochromic materials/compounds.

Figure 1B:
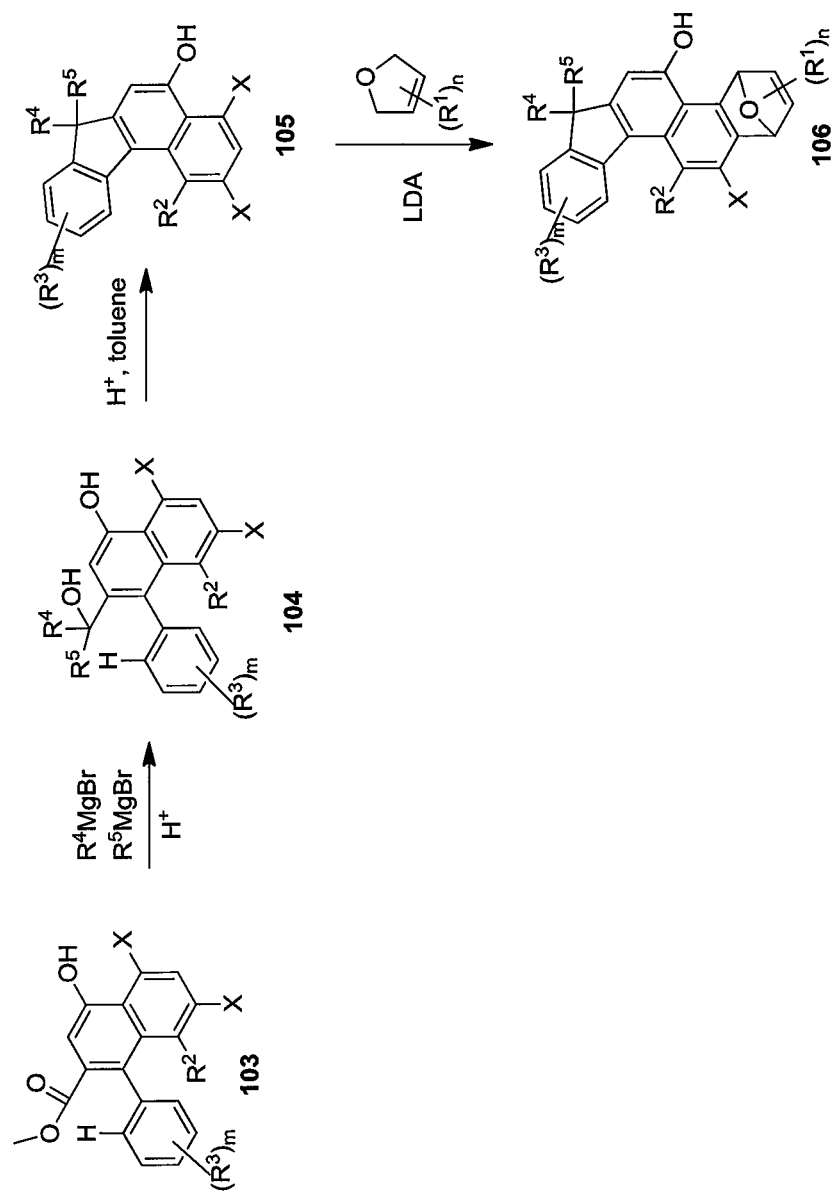
FIG. 1(b) is an illustrative representative second part (Part 2) of the general scheme, Scheme 1, of FIG. 1(a)
Figure 1C:
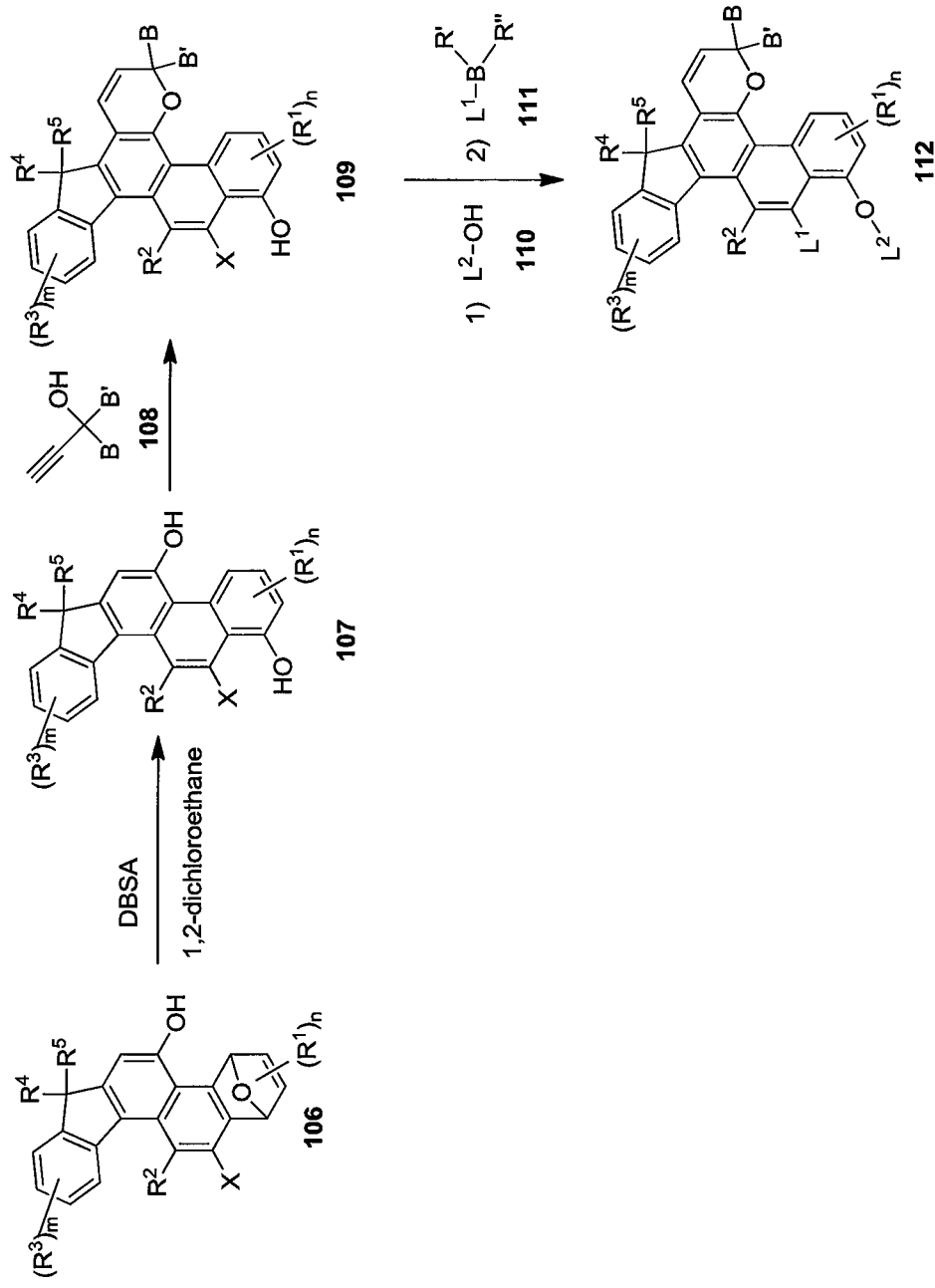
FIG. 1(c) is an illustrative representative third part (Part 3) of the general scheme, Scheme 1, of FIGS. 1(a) and 1(b).

Photochromic compounds according to the present invention can be prepared in accordance with art-recognized methods. For purposes of non-limiting illustration and with reference to FIGS. 1(a) through 1(c) of the drawings, a general synthetic scheme, Scheme 1, for the preparation of photochromic compounds according to the present invention is described as follows. Further detailed descriptions of the preparation of photochromic compounds of the present invention are provided further herein in the Examples. In FIGS. 1(a) through 1(c), the various groups, such as $R^1$, $R^2$, $R^3$, $R^4$, $R^5$, B, B', $L^1$, and $L^2$, and related subscripts, such as n and m, of the various intermediates, reactants, and/or compounds depicted, are each as described previously herein, and/or represent precursors of such groups.

With reference to FIG. 1(a), in a first step, an aryl ketone (101) is subjected to an art-recognized Stobbe Condensation, that involves reaction of aryl ketone (101) with dimethyl succinate (not shown) in the presence of potassium t-butoxide, which results in the formation of intermediate (102). Intermediate (102) can next undergo ring closure in acetic anhydride, followed by methanolysis (such as by reaction with methanol in 12N HCl), which results in the formation of intermediate (103).

With reference to FIG. 1(b), intermediate (103) can be reacted with Grignard reagents (such as $R^4$MgBr and $R^5$MgBr) under art-recognized Grignard reaction conditions, which results in the formation of intermediate (104). Intermediate (104) can then be subjected to ring closure under art-recognized conditions (such as under acidic conditions in the presence of a suitable solvent, such as toluene), which results in the formation of intermediate (105). Intermediate (105) can next be reacted with an $R^1$ substituted 2,5-dihydrofuran in the presence of lithium diisopropylamide (LDA) under appropriate art-recognized conditions, such as in an ice-water bath, which results in the formation of intermediate (106).

With reference to FIG. 1(c), intermediate (106) can next be subjected to reflux conditions in 1,2-dichloroethane, in the presence of dodecylbenzenesulfonic acid (DBSA), which results in the formation of intermediate (107). Intermediate (107) can next be reacted with propargyl alcohol (108), under art-recognized conditions, which results in the formation of intermediate (109), having a B/B' substituted 2H-pyran fused ring. With some embodiments, intermediate (109) is representative of a photochromic compound according to the present invention.

In accordance with some embodiments, intermediate (109) can be further modified so as to include lengthening groups at positions 1 and/or 15 thereof. With further reference to FIG. 1(c), intermediate (109) can be reacted with a hydroxy functional lengthening group (110), under art-recognized condensation reaction conditions, which results in the introduction of an ether linked lengthening group (—O-$L^2$) as position 1 thereof. In addition or alternatively to the introduction of an ether linked lengthening group (—O-$L^2$), intermediate (109) can be reacted with a boron group modified lengthening group (111) under art-recognized conditions (such as by way of a Suzuki reaction), which results in the introduction of a lengthening group (-$L^1$) bonded to position 15 thereof. The R' and R" groups of the boron group (—B(R')(R")) of the boron group modified lengthening group (111) can each independently be selected from hydroxyl and alkyl ether (such as, linear or branched C1-C10 alkyl ether), with some embodiments. Photochromic compound (112) of FIG. 1(c) has both an ether linked lengthening group (—O-$L^2$) at position 1 thereof, and a lengthening group (-$L^1$) bonded to position 15 thereof. The "B" of the boron group (—B(R')(R")) of the boron group modified lengthening group (111) of FIG. 1(c) represents a boron atom, and does not correspond to or otherwise represent the B and B' groups of the photochromic compounds of the present invention, such as represented by Formula (I) and photochromic compound (112), or the materials used in the preparation thereof, such as propargyl alcohol (108) and intermediate (109) of FIG. 1(c).

In accordance with the present invention there is also provided a photochromic composition, which includes at least one photochromic compound according to the present invention, such as represented by Formula (I), as described previously herein.

In accordance with some embodiments of the present invention, the photochromic composition includes: (i) an organic material, in which the organic material is at least one of a polymeric material, an oligomeric material, and/or a monomeric material; and (ii) a photochromic compound according to the present invention, which is incorporated into at least a portion of the organic material. The photochromic compound can be incorporated into a portion of the organic material by methods including, but not limited to, at least one of blending and/or bonding the photochromic compound with the organic material or a precursor of the organic material. As used herein with reference to the incorporation of photochromic compounds into an organic material, the terms "blending" and "blended" mean that the photochromic compound/material is intermixed or intermingled with the at least a portion of the organic material, but not bonded to the organic material. Further, as used herein with reference to the incorporation of photochromic compounds into an organic material, the terms "bonding" or "bonded" mean that the photochromic compound/material is linked, such as by one or more covalent bonds, to a portion of the organic material or a precursor thereof. For example, although not limiting herein, the photochromic material can be linked to the organic material through a reactive substituent.

In accordance with some embodiments of the present invention, when the organic material is a polymeric material, the photochromic compound can be incorporated into at least a portion of the polymeric material or at least a portion of the monomeric material or oligomeric material from which the polymeric material is formed. For example, photochromic compound(s) according to the present invention that have a reactive substituent can be bonded to an organic material such as a monomer, oligomer, or polymer having a group with which a reactive moiety may be reacted, or the reactive moiety can be reacted as a co-monomer in the polymerization reaction from which the organic material is formed, for example, in a co-polymerization process.

As discussed above, the photochromic compositions according to present invention can include an organic material chosen from a polymeric material, an oligomeric material and/or a monomeric material, with some embodiments. Examples of polymeric materials that can be used with the photochromic compositions of the present invention include, but are not limited to: polymers of bis(allyl carbonate) monomers; diethylene glycol dimethacrylate monomers; diisopropenyl benzene monomers; ethoxylated bisphenol A dimethacrylate monomers; ethylene glycol bismethacrylate monomers; poly(ethylene glycol) bismethacrylate monomers; ethoxylated phenol bismethacrylate monomers; alkoxylated polyhydric alcohol acrylate monomers, such as ethoxylated trimethylol propane triacrylate monomers; urethane acrylate monomers; vinylbenzene monomers; and styrene. Further examples of suitable polymeric materials include, but are not limited to, polymers of polyfunctional, e.g., mono-, di- or multi-functional, acrylate and/or methacrylate monomers; poly($C_1$-$C_{12}$ alkyl methacrylates), such as poly(methyl methacrylate); poly(oxyalkylene)dimethacrylate; poly(alkoxylated phenol methacrylates); cellulose acetate; cellulose triacetate; cellulose acetate propionate; cellulose acetate butyrate; poly(vinyl acetate); poly(vinyl alcohol); poly(vinyl chloride); poly(vinylidene chloride); polyurethanes; polythiourethanes; thermoplastic polycarbonates; polyesters; poly(ethylene terephthalate); polystyrene; poly(alpha-methylstyrene); copolymers of styrene and methyl methacrylate; copolymers of styrene and acrylonitrile; polyvinylbutyral; and polymers of diallylidene pentaerythritol, particularly copolymers with polyol (allyl carbonate) monomers, e.g., diethylene glycol bis(allyl carbonate), and acrylate monomers, such as ethyl acrylate, butyl acrylate. Also contemplated are copolymers of the aforementioned monomers, combinations, and blends of the aforementioned polymers and copolymers with other polymers (e.g., to form interpenetrating network products).

With some embodiments, transparency of the photochromic composition is desired, in which case the organic material can be a transparent polymeric material. The polymeric material can be, with some embodiments, an optically clear polymeric material prepared from a thermoplastic polycarbonate resin, such as the resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; and polymerizates of a polyol(allyl carbonate) monomer, especially diethylene glycol bis(allyl carbonate), which monomer is sold under the trademark CR-39®); and polyurea-polyurethane (polyurea urethane) polymers, which are prepared, for example, by the reaction of a polyurethane oligomer and a diamine curing agent, a composition for one such polymer being sold under the trademark TRIVEX® by PPG Industries, Inc. Other non-limiting examples of suitable polymeric materials include polymerizates of copolymers of a polyol (allyl carbonate), e.g., diethylene glycol bis(allyl carbonate), with other copolymerizable monomeric materials, such as, but not limited to: copolymers with vinyl acetate, copolymers with a polyurethane having terminal diacrylate functionality, and copolymers with aliphatic urethanes, the terminal portion of which contain allyl or acrylyl functional groups. Still other suitable polymeric materials include, without limitation, poly(vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and copolymers of styrene with methyl methacrylate, vinyl acetate and acrylonitrile. According to further embodiments, the polymeric material can be an optical resin commercially available from PPG Industries, Inc. under the CR-designation, such as CR-307, CR-407, and CR-607.

In accordance with some embodiments, the organic material can be a polymeric material which is chosen from poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl(meth)acrylamide functional polymers; poly(siloxane); poly(silane); and combinations and mixtures thereof.

With some further embodiments, the photochromic composition of the present invention further includes at least one of, a complementary photochromic material (including one or more of those other photochromic materials and compounds described previously herein), a photoinitiator, a thermal initiator, a polymerization inhibitor, a solvent, a light stabilizer, a heat stabilizer, a mold release agent, a rheology control agent, a leveling agent, a free radical scavenger, and/or an adhesion promoter.

In accordance with some embodiments, the photochromic composition according to the present invention is a photochromic coating composition. Photochromic coating compositions according to some embodiments of the present invention include: a photochromic material according to the present invention, such as described previously herein with regard to Formula (I); a resin composition that is optionally curable; and optionally a solvent. The photochromic coating composition can be in the form of art-recognized liquid coatings and powder coatings. The photochromic coating compositions of the present invention can be thermoplastic or thermosetting coating compositions. In an embodiment, the photochromic coating composition is a curable or thermosetting coating composition.

The curable resin composition of the curable photochromic coating compositions according to some embodiments of the present invention include: a first reactant (or component) having functional groups, e.g., an epoxide functional polymer reactant; and a second reactant (or component) that is a crosslinking agent having functional groups that are reactive towards and that can form covalent bonds with the functional groups of the first reactant. The first and second reactants of the curable resin composition of the curable photochromic coating composition can each independently include one or more functional species, and are each present in amounts sufficient to provide cured photochromic coatings having a desirable combination of physical properties, e.g., smoothness, optical clarity, solvent resistance, and hardness.

Examples of curable resin compositions that can be used with the curable photochromic coating compositions according to the present invention include, but are not limited to: curable resin compositions including epoxide functional polymer (e.g., (meth)acrylic polymers containing residues of glycidyl (meth)acrylate and epoxide reactive crosslinking agent (e.g., containing active hydrogens, such as hydroxyls, thiols and amines); and curable resin compositions including hydroxy functional polymer and capped (or blocked) isocyanate functional crosslinking agent.

With some embodiments, the curable resin composition of the photochromic coating composition of the present invention is a curable urethane (or polyurethane) resin composition. Curable urethane resin compositions useful in the photochromic coating compositions of the present invention typically include: an active hydrogen functional polymer, such as a hydroxy functional polymer; and a capped (or blocked) isocyanate functional crosslinking agent. Hydroxy functional polymers that can be used in such compositions include, but are not limited to, art-recognized hydroxy functional vinyl polymers, hydroxy functional polyesters, hydroxy functional polyurethanes and mixtures thereof.

Vinyl polymers having hydroxy functionality can be prepared by free radical polymerization methods that are known to those of ordinary skill in the art. In an embodiment of the present invention, the hydroxy functional vinyl polymer is prepared from a majority of (meth)acrylate monomers and is referred to herein as a "hydroxy functional (meth) acrylic polymer."

Hydroxy functional polyesters useful in curable photochromic coating compositions comprising capped isocyanate functional crosslinking agent can be prepared by art-recognized methods. Typically, diols and dicarboxylic acids or diesters of dicarboxylic acids are reacted in a proportion such that the molar equivalents of hydroxy groups is greater than that of carboxylic acid groups (or esters of carboxylic acid groups) with the concurrent removal of water or alcohols from the reaction medium.

Hydroxy functional urethanes can be prepared by art-recognized methods, for example, as previously described herein. Typically one or more difunctional isocyanates are reacted with one or more materials having two active hydrogen groups (e.g., diols or dithiols), such that the ratio of active hydrogen groups to isocyanate groups is greater than 1, as is known to the skilled artisan.

By "capped (or blocked) isocyanate crosslinking agent" is meant a crosslinking agent having two or more capped isocyanate groups that can decap (or deblock) under cure conditions, e.g., at elevated temperature, to form free isocyanate groups and free capping groups. The free isocyanate groups formed by decapping of the crosslinking agent are preferably capable of reacting and forming substantially permanent covalent bonds with the active hydrogen groups of the active hydrogen functional polymer (e.g., with the hydroxy groups of a hydroxy functional polymer).

It is desirable that the capping group of the capped isocyanate crosslinking agent not adversely affect the curable photochromic coating composition upon decapping from the isocyanate (i.e., when it becomes a free capping group). For example, it is desirable that the free capping group neither become trapped in the cured film as gas bubbles nor excessively plasticize the cured film. Capping groups useful in the present invention preferably have the characteristics of being nonfugitive or capable of escaping substantially from the forming coating prior to its vitrification. Typically, the free capping groups escape substantially from the forming (e.g., curing) coating prior to its vitrification.

Classes of capping groups of the capped isocyanate crosslinking agent can be selected from: hydroxy functional compounds, e.g., linear or branched $C_2$-$C_8$ alcohols, ethylene glycol butyl ether, phenol and p-hydroxy methylbenzoate; 1H-azoles, e.g., 1H-1,2,4-triazole and 1H-2,5-dimethyl pyrazole; lactams, e.g., e-caprolactam and 2-pyrolidinone; ketoximes, e.g., 2-propanone oxime and 2-butanone oxime. Other suitable capping groups include, morpholine, 3-aminopropyl morpholine and N-hydroxy phthalimide.

The isocyanate or mixture of isocyanates of the capped isocyanate crosslinking agent has two or more isocyanate groups (e.g., 3 or 4 isocyanate groups). Examples of suitable isocyanates that can be used to prepare the capped isocyanate crosslinking agent include, monomeric diisocyanates, e.g., $\alpha,\alpha'$-xylylene diisocyanate, $\alpha,\alpha,\alpha',\alpha'$-tetramethylxylylene diisocyanate and 1-isocyanato-3-isocyanatomethyl-3,5,5-trimethylcyclohexane (isophorone diisocyanate or IPDI), and dimers and trimers of monomeric diisocyanates containing isocyanurate, uretidino, biruet or allophanate linkages, e.g., the trimer of IPDI.

The capped isocyanate crosslinking agent can also be selected from oligomeric capped isocyanate functional adducts. As used herein, by "oligomeric capped polyisocyanate functional adduct" is meant a material that is substantially free of polymeric chain extension. Oligomeric capped polyisocyanate functional adducts can be prepared by art-recognized methods from, for example, a compound containing three or more active hydrogen groups, e.g., trimethylolpropane (TMP), and an isocyanate monomer, e.g., 1-isocyanato-3,3,5-trimethyl-5-isocyanatomethylcyclohexane (IPDI), in a molar ratio of 1:3, respectively. In the case of TMP and IPDI, by employing art-recognized starved feed and/or dilute solution synthesis techniques, an oligomeric adduct having an average isocyanate functionality of 3 can be prepared (e.g., "TMP-3IPDI"). The three free isocyanate groups per TMP-3IPDI adduct are then capped with a capping group, e.g., a linear or branched $C_2$-$C_8$ alcohol.

To catalyze the reaction between the isocyanate groups of the capped polyisocyanate crosslinking agent and the hydroxy groups of the hydroxy functional polymer, one or more catalysts are typically present in the curable photochromic coating composition in amounts of from, for example, 0.1 to 5 percent by weight, based on total resin solids of the composition. Classes of useful catalysts include but are not limited to, metal compounds, in particular, organic tin compounds, e.g., tin(II) octanoate and dibutyltin (IV) dilaurate, and tertiary amines, e.g., diazabicyclo[2.2.2] octane.

Curable photochromic coating compositions according to the present invention, which include hydroxy functional polymer and capped isocyanate functional crosslinking agent, typically have present therein hydroxy functional polymer in an amount of from 55 percent to 95 percent by weight, based on total resin solids weight of the composition, e.g., from 75 percent to 90 percent by weight, based on total resin solids weight of the composition. The capped isocyanate functional crosslinking agent is typically present in the curable resin composition in an amount corresponding to the balance of these recited ranges, i.e., 5 to 45, particularly 10 to 25, percent by weight.

With the curable urethane resin compositions of the curable photochromic coating compositions of the present invention, the equivalent ratio of isocyanate equivalents in the capped isocyanate crosslinking agent to hydroxy equivalents in the hydroxy functional polymer is typically within the range of 1:3 to 3:1, e.g., 1:2 to 2:1. While equivalent ratios outside of this range can be employed, they are generally less desirable due to performance deficiencies in cured photochromic films obtained therefrom. Curable photochromic coating compositions according to the present invention that include hydroxy functional polymer and capped isocyanate functional crosslinking agent are typically cured at a temperature of from 120° C. to 190° C. over a period of from 10 to 60 minutes.

Photochromic coating compositions according to the present invention can, with some embodiments, optionally further include a solvent. Examples of suitable solvents include, but art not limited to, acetates, alcohols, ketones, glycols, ethers, aliphatics, cycloaliphatics and aromatics. Examples of acetates include, but are not limited to, ethyl acetate, butyl acetate, and glycol acetate. Examples of ketones include, but are not limited to, methyl ethyl ketone and methyl-N-amyl ketone. Examples of aromatics include, but are not limited to, are toluene, naphthalene and xylene. In an embodiment, one or more solvents are added to each of the first reactant and the second reactant. Suitable solvent blends can include, for example, one or more acetates, propanol and its derivatives, one or more ketones, one or more alcohols and/or one or more aromatics. If present, the solvent is typically present in an amount of from 5 to 60 percent by weight, or 5 to 40 percent by weight, or 10 to 25 percent by weight, based on the total weight of the photochromic coating composition (inclusive of the solvent weight).

Curable photochromic coating compositions according to the present invention can, with some embodiments, optionally contain additives such as waxes for flow and wetting, flow control agents, e.g., poly(2-ethylhexyl)acrylate, adjuvant resin to modify and optimize coating properties, antioxidants and ultraviolet (UV) light absorbers. Examples of useful antioxidants and UV light absorbers include those available commercially from Ciba-Geigy under the trademarks IRGANOX and TINUVIN. These optional additives, when used, are typically present in amounts up to 20 percent by weight (e.g., from 0.5 to 10 percent by weight), based on total weight of resin solids of the curable resin composition.

Photochromic compositions, photochromic articles and photochromic coating compositions according to the present invention can, with some embodiments, further include art-recognized additives that aid or assist in the processing and/or performance of the compositions or articles. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

The photochromic compounds of the present invention can be used in amounts (or ratios) such that the compositions, organic material or substrate (e.g., photochromic articles and photochromic coatings) into which the photochromic compounds are incorporated or otherwise connected exhibits desired optical properties. With some embodiments, the amount and types of photochromic material can be selected such that the composition, organic material or substrate is clear or colorless when the photochromic compound is in the closed-form (e.g., in the bleached or unactivated state), and can exhibit a desired resultant color when the photochromic compound (such as a photochromic indeno-fused phenanthrenopyran of the present invention) is in the open-form (e.g., when activated by actinic radiation). The precise amount of the photochromic material that is utilized in the various photochromic compositions and articles described herein is not critical provided that a sufficient amount is used to produce the desired effect. The particular amount of the photochromic material used can depend on a variety of factors, such as but not limited to, the absorption characteristics of the photochromic compound, the color and intensity of the color desired upon activation, and the method used to incorporate or connect the photochromic material to the substrate. Photochromic compositions according to some embodiments of the present invention can include the photochromic material according to the present invention, including the compounds represented by Formula (I), in an amount of from 0.01 to 40 weight percent, or from 0.05 to 15, or from 0.1 to 5 weight percent, based on the weight of the photochromic composition. For purposes of further non-limiting illustration, the amount of the photochromic compound/material including the compounds represented by Formula (I) that is incorporated into an organic material can range from 0.01 to 40 weight percent, or from 0.05 to 15, or from 0.1 to 5 weight percent, based on the weight of the organic material.

The present invention also relates to photochromic articles that include one or more photochromic compounds according to the present invention, such as represented by Formula (I). The photochromic articles are, with some embodiments, prepared by art-recognized methods, such as by imbibition methods, cast-in-place methods, coating methods, in-mold coating methods, over-mold methods, and lamination methods.

With some embodiments, the photochromic articles are selected from ophthalmic articles, display articles, windows, mirrors, and active liquid crystal cell articles, and passive liquid crystal cell articles.

In accordance with some further embodiments, the photochromic articles of the present invention are ophthalmic articles, and the ophthalmic articles are selected from corrective lenses, non-corrective lenses, contact lenses, intraocular lenses, magnifying lenses, protective lenses, and visors.

With some additional embodiments, the photochromic articles of the present invention are display articles, and the display articles are selected from screens, monitors, and security elements.

The present invention is more particularly described in the following examples, which are intended as illustrative only, since numerous modifications and variations therein will be apparent to those skilled in the art.

EXAMPLES

The following examples are provided in Parts 1-4, which are briefly summarized as follows. In Part 1 there are provided descriptions of the synthesis of photochromic compounds according to the present invention and comparative photochromic compounds. In Part 2 there is provided an evaluation of the photochromic performance of the photochromic compounds of Examples 1-6, and 10, and Comparative Examples 16-20 (CE16-CE20). In Parts 3 and 4 there is provided an evaluation of the photochromic-dichroic performance of certain photochromic compounds according to the present invention and comparative photochromic compounds, that in each case include one or more lengthening groups. More particularly, in Part 3 there is provided an evaluation of liquid crystal cell performance, and in Part 4 there is provided an evaluation of the photochromic performance of aligned coating stacks.

Part 1: Synthesis of Photochromic Compounds According to the Present Invention and Comparative Photochromic Compounds.

Example 1

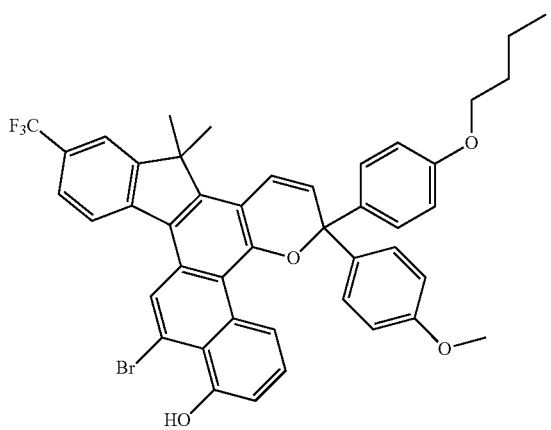 [SMILES: CCCCOc1ccc(C2(c3ccc(OC)cc3)C=Cc3c4c(c5cc(Br)c6c(O)cccc6c5c3O2)-c2ccc(C(F)(F)F)cc2C4(C)C)cc1]

Step 1

Tribromobenzene (500.0 g) and tetrahydrofuran (THF) (2.0 L) were mixed and cooled to −10° C. To the solution was added isopropylmagnesium chloride (800.0 mL of a 2M solution in THF) drop-wise, maintaining a temperature of less than 0° C. At that temperature, the solution was stirred for 40 minutes, bis[2-(N,N-dimethylamino)-ethyl]ether (364.0 mL) was added and stirred for 15 minutes, and then 4-Trifluoromethylbenzoyl chloride (261.0 mL) was added and stirred for 20 minutes. The reaction mixture was warmed to room temperature, stirred for 20 hours, poured into 10% aqueous hydrochloric acid (4.0 L), and then stirred for 15 minutes. The aqueous solution was extracted three times with 1 L ethyl acetate. The combined extracts were washed with 1.0 L each of brine, a 10% w/w aqueous sodium hydroxide solution, and then brine. The extract was dried with anhydrous sodium sulfate, filtered, and concentrated under vacuum to provide an oil residue. The residue was recrystallized in methanol (1.0 L) to provide colorless crystals (347.0 g). NMR analysis indicated a structure consistent with (3,5-dibromophenyl)(4-(trifluoromethyl)phenyl) methanone.

Step 2

The product from Step 1 (264.4 g), dimethyl succinate (102.0 mL), and toluene (2 L) were stirred under nitrogen until the solids dissolved. Potassium tert-butoxide (110.0 g) and toluene (2.0 L) were added, and the mixture was stirred at room temperature for 2 hours. Water (2.0 L) was slowly added to the mixture, followed by concentrated hydrochloric acid (120.0 mL), and stirred for 10 minutes. The aqueous solution was extracted three times with 1 L ethyl acetate, and the combined extracts were dried with anhydrous sodium sulfate, filtered, and concentrated to provide an oily residue. The mixture was then recrystallized in hexanes to produce a cream colored precipitate (237.9 g). NMR analysis indicated a structure consistent with (E)-4-(3,5-dibromophenyl)-3-(methoxycarbonyl)-4-(4-(trifluoromethyl)phenyl)but-3-enoic acid.

Step 3

The product from Step 2 (7.8 g) was dissolved in toluene (200 mL), to which acetic anhydride (2.1 mL) was added. The mixture was heated at reflux for 3 hours, and the solvent was removed under vacuum to provide an oily residue, which was dissolved in methanol (200 mL). Concentrated hydrochloric acid (1 mL) was added. The solution was heated at reflux for 6 hours, and the solvent was removed under vacuum to provide a dark colored oil. The oil was passed through a plug of silica gel (Grade 60, 230-400 mesh) and eluted with a 4:1 (v:v) hexane to ethyl acetate mixture. Fractions containing the desired material were grouped and concentrated to provide a yellow colored oil.

Step 4

The oil (5.3 g) from Step 3 was dissolved in anhydrous tetrahydrofuran (50 mL) and cooled to 0° C. Methylmagnesium chloride (14.1 mL of a 3M solution in THF) was added drop-wise, and the solution was warmed to room temperature, stirred for 2 hours, poured into 10% by weight aqueous hydrochloric acid (100.0 mL), and stirred for an additional 30 minutes. The aqueous solution was removed and extracted three times with 50 mL ethyl acetate. The combined extracts were dried with anhydrous sodium sulfate, filtered, and concentrated to provide an oily residue, which was passed through a plug of silica gel (Grade 60, 230-400 mesh), eluting with a 9:1 (v:v) hexanes to ethyl acetate mixture. Fractions containing the desired material were grouped and concentrated under vacuum to provide an oily residue (0.7 g).

Step 5

The oil (0.7 g) from Step 4 was dissolved in toluene (20.0 mL), and bismuth triflate (10.0 mg) was added. The mixture was heated at reflux for 2 hours, and the solvent was removed under vacuum. The recovered residue was passed through a plug of silica gel (Grade 60, 230-400 mesh), eluting with a 4:1 (v:v) hexanes to ethyl acetate mixture. Fractions containing the desired material were concentrated and precipitated in hexanes to produce a cream colored solid (0.5 g). NMR analysis indicated a structure consistent with 2,4-dibromo-7,7-dimethyl-9-(trifluoromethyl)-7H-benzo[c] fluoren-5-ol.

Step 6

A chloroform solution (600 mL) of the product from Step 5 (0.5 g) and p-toluene sulfonic acid (20.0 mg) were added to 1-(4-butoxyphenyl)-1-(4-methoxyphenyl)-prop-2-yn-1-ol (0.5 g). The solution was heated at reflux for 4 hours and then passed through a plug of silica gel (Grade 60, 230-400 mesh), eluting with a 9:1 (v:v) hexane to ethyl acetate mixture. Fractions containing the desired material were grouped and concentrated to provide a purple colored solid (0.4 g). NMR analysis indicated a structure consistent with 3-(4-butoxyphenyl)-3-(4-methoxyphenyl)-5,7-dibromo-11-trifluoromethyl-13,13-dimethyl-3,13-dihydro-indeno[2',3': 3,4]naphtho[1,2-b]pyran.

Step 7

The solid from Step 6 (15.6 g; synthesized in a repeated, scaled-up reaction) was dissolved in a mixture of furan (50 mL) and THF (80 mL), cooled with an ice-water bath, and then lithium diisopropyl amine solution in THF (3 eq) was added slowly. After 10 minutes, the reaction was quenched with ammonium chloride solution, and the organic product was extracted with ethyl acetate, dried over anhydrous sodium sulfate, and concentrated. The residue was purified by CombiFlash chromatography, eluting with an 85:15 (v:v) hexane to ethyl acetate mixture to provide 9.4 g solid product. NMR analysis indicated a structure consistent with 15-bromo-6-(4-butoxyphenyl)-6-(4-methoxyphenyl)-9,9-dimethyl-11-(trifluoromethyl)-1,4,6,9-tetrahydro-1,4-epoxyindeno[2,1-f]naphtho[2,1-h]chromene.

Step 8

The solid from step 7 (5.92 g) was dissolved in 600 mL 1,2-dichloroethane, and p-toluene sulfonic acid (1.47 g) was added. The mixture was refluxed for 2 hours, cooled to room temperature, and neutralized by stirring with sodium bicarbonate solution (300 mL). The organic phase was separated, washed with brine, dried over anhydrous sodium sulfate, and concentrated by vacuum. The residue was purified by CombiFlash chromatography to yield about 2 g solid product. NMR analysis indicated a structure consistent with 6-(4-methoxyphenyl)-6-(4-butoxyphenyl)-9,9-dimethyl-1-hydroxy-15-bromo-11-trifluoromethyl-6H,9H-indeno[2',3':2, 1]phenanthro[4,3-b]pyran.

Example 2

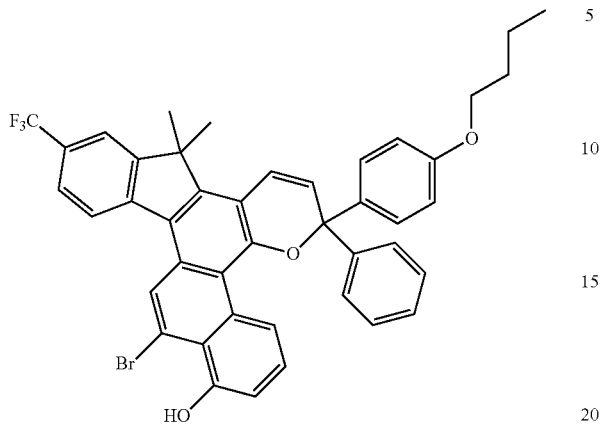

The procedures of Example 1 were followed except that in Step 6, an equimolar amount of 1-(4-butoxyphenyl)-1-phenyl-prop-2-yn-1-ol was used in place of 1-(4-butoxyphenyl)-1-(4-methoxyphenyl)-prop-2-yn-1-ol. NMR analysis indicated a structure consistent with 6-phenyl-6-(4-butoxyphenyl)-9,9-dimethyl-1-hydroxy-15-bromo-11-trifluoromethyl-6H,9H-indeno[2',3':2,1]phenanthro[4,3-b]pyran.

Example 3

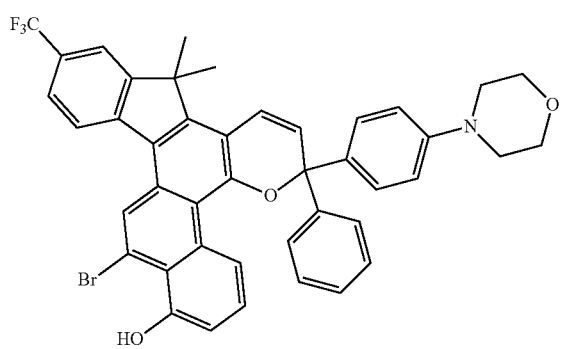 [SMILES: CC1(C)c2cc(C(F)(F)F)ccc2-c2c1c1c(c3c2cc(Br)c2c(O)cccc23)OC(c2ccccc2)(c2ccc(N3CCOCC3)cc2)C=C1]

The procedures of Example 1 were followed except that in Step 6, an equimolar amount of 1-(4-morpholinophenyl)-1-phenyl-prop-2-yn-1-ol was used in place of 1-(4-butoxyphenyl)-1-(4-methoxyphenyl)-prop-2-yn-1-ol. NMR analysis indicated a structure consistent with 6-phenyl-6-(4-morpholinophenyl)-9,9-dimethyl-1-hydroxy-15-bromo-11-trifluoromethyl-6H,9H-indeno[2',3':2,1]phenanthro[4,3-b]pyran.

Example 4

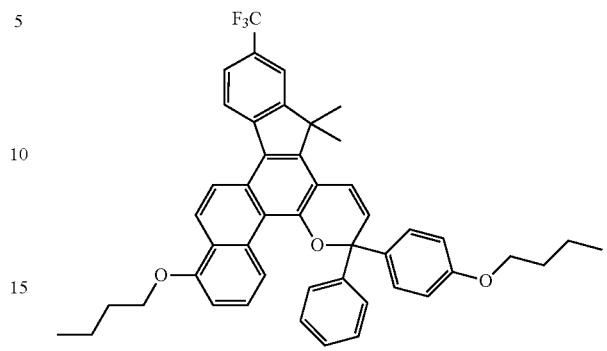

Step 1

The product from Example 2, (0.74 g), 1-iodobutane (0.37 mL), and potassium carbonate (0.27 g) were added to THF (70 mL), and the mixture was refluxed for 12 hours. The mixture was poured into water (100 mL) and extracted with ethyl acetate (60 mL). The organic phase was washed with brine, dried over anhydrous sodium sulfate, and concentrated. The residue was purified by CombiFlash, eluting with a 9:1 (v:v) hexane to ethyl acetate mixture, to yield 0.7 g solid product.

Step 2

The solid from Step 1 (0.7 g) was dissolved in THF (25 mL) and cooled with a dry ice acetone bath for 10 minutes. Butyl lithium solution in hexane (1.5 equivalent) was added dropwise to the solution while stirring. After 5 minutes, brine was added to the reaction mixture, the dry ice acetone bath was removed, and then the mixture was extracted with ethyl acetate. The organic phase was separated, dried with anhydrous sodium sulfate, concentrated, and purified by CombiFlash chromatography, using a 9:1 (v:v) hexane to ethyl acetate mixture as the eluent, to yield 0.4 g solid product. NMR analysis indicated a structure consistent with 6-phenyl-6-(4-butoxyphenyl)-9,9-dimethyl-1-butoxy-11-trifluoromethyl-6H,9H-indeno[2',3':2,1]phenanthro[4,3-b]pyran.

Example 5

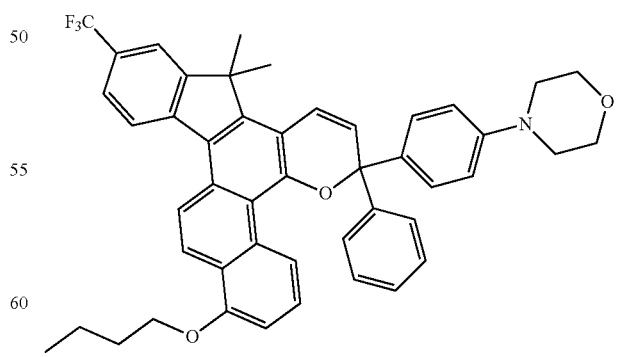

The procedures from Example 4 were followed except that in Step 1, an equimolar amount of the product from Example 3 was used in place of the product from Example 2. NMR analysis indicated a structure consistent with 6-phenyl-6-(4-morpholinophenyl)-9,9-dimethyl-1-butoxy-11-trifluoromethyl-6H,9H-indeno[2',3':2,1]phenanthro[4,3-b]pyran.

Example 6

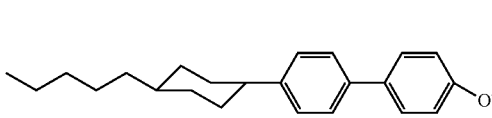

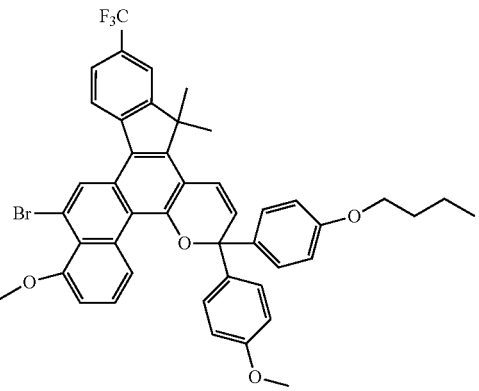

The product from Example 1 (2.6 g), 6-((4'-(trans-4-pentylcyclohexyl)-[1,1'-biphenyl]-4-yl)oxy)hexan-1-ol (1.72 g), and triphenylphosphine (1.07 g) were dissolved in THF (10 mL). Diisopropyl azodicarboxylate (0.83 g) was added, and the mixture was stirred for 12 hours, poured into water (20 mL), and extracted with ethyl acetate (30 mL). The organic phase was washed with brine, dried over anhydrous sodium sulfate, and concentrated. The residue was purified by CombiFlash, eluting with an 85:15 (v:v) hexane to ethyl acetate mixture, to yield 2.9 g solid product. NMR analysis indicated a structure consistent with 6-(4-methoxyphenyl)-6-(4-butoxyphenyl)-9,9-dimethyl-1-((6-((4'-(trans-4-pentylcyclohexyl)-[1,1'-biphenyl]-4-yl)oxy)hexyl)oxy)-15-bromo-11-trifluoromethyl-6H,9H-indeno[2',3':2,1]phenanthro[4,3-b]pyran.

Example 7 mL) was added, a precipitate formed, and the suspension mixture was heated with a 100° C. oil bath for 4 hours. The mixture was cooled to room temperature, and a 3N HCl solution (50 mL) was added. The precipitate was collected and stirred in a mixture of THF (200 mL) and 1N dilute acid (120 mL) until the solid dissolved. The organic phase was separated, dried over anhydrous sodium sulfate, and recrystallized in hexanes to give a pale white solid (13.88 g). NMR analysis indicated a structure consistent with 6-((4'-(trans-4-pentylcyclohexyl)-[1,1'-biphenyl]-4-yl)oxy)hexanoic acid.

Step 2

The product from Example 1 (3.1 g) was added to a mixture of 4-dimethylaminopyridine (0.31 g), dodecylbenzenesulfonic acid (0.62 g), and dichloromethane (60 mL), stirred, then the product from Step 1 (1.96 g) was added. N,N'-Dicyclohexylcarbodiimide (0.93 g) was added and stirred for 12 hours. A white precipitate was filtered off, and the filtrate was concentrated, to which methanol (80 mL) was added. The clear portion was decanted from the milky oil, and the oil was then purified by CombiFlash, eluting

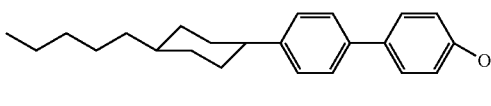

Step 1

4'-(trans-4-pentylcyclohexyl)-[1,1'-biphenyl]-4-ol (12.89 g), ethyl 6-bromohexanoate (10.71 g), and potassium hydroxide (8.98 g) were added to dimethyl sulfoxide (130 mL). The mixture was heated with an 80° C. oil bath for 1 hour and then cooled to room temperature. After water (150 with an 85:15 (v:v) hexane to ethyl acetate mixture, to yield 3.3 g solid product. NMR analysis indicated a structure consistent with 6-(4-methoxyphenyl)-6-(4-butoxyphenyl)-9,9-dimethyl-1-(5-((4'-(trans-4-pentylcyclohexyl)-[1,1'-biphenyl]-4-yl)oxy)pentylcarbonyloxy)-15-bromo-11-trifluoromethyl-6H,9H-indeno[2',3':2,1]phenanthro[4,3-b]pyran.

Example 8

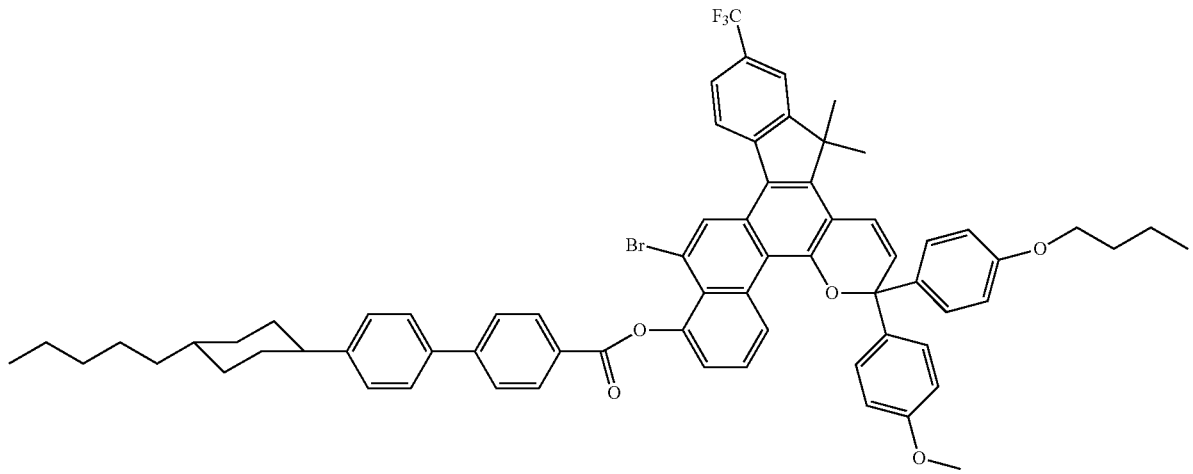 [SMILES: CCCCCC1CCC(c2ccc(-c3ccc(C(=O)Oc4cccc5c4c(Br)cc4c6c(c7c(c45)OC(c4ccc(OC)cc4)(c4ccc(OCCCC)cc4)C=C7)C(C)(C)c4cc(C(F)(F)F)ccc4-6)cc3)cc2)CC1]

The product from Example 1 (0.6 g) and trimethylamine (0.24 g) were dissolved in dichloromethane (25 mL), to which a solution of 4'-(trans-4-pentylcyclohexyl)-[1,1'-biphenyl]-4-carbonyl chloride (0.29 g) in dichloromethane (25 mL) was added. After stirring for 12 hours, the mixture was washed with water (30 mL), and the organic phase was separated, dried with anhydrous sodium sulfate, and concentrated. The residue was purified by CombiFlash chromatography, eluting with a 9:1 (v:v) hexane to ethyl acetate mixture, to yield 0.6 g solid product. NMR analysis indicated a structure consistent with 6-(4-methoxyphenyl)-6-(4-butoxyphenyl)-9,9-dimethyl-1-((4'-(trans-4-pentylcyclohexyl)-[1,1'-biphenyl]-4-yl)carbonyloxy)-15-bromo-11-trifluoromethyl-6H,9H-indeno[2',3':2,1]phenanthro[4,3-b]pyran.

Example 9

Step 1

The product from Example 1 (0.58 g) was dissolved in anhydrous THF (15 mL) and cooled with a dry ice-acetone bath for 15 minutes with stirring. Butyl lithium solution in hexane (3 eq) was added dropwise, stirred for 10 minutes, then brine (15 mL) was added. The mixture was warmed to room temperature and extracted with ethyl acetate (30 mL). The organic phase was separated, dried with anhydrous sodium sulfate, and concentrated. The residue was purified by CombiFlash chromatography, eluting with a 4:1 (v:v) hexane to ethyl acetate mixture, to yield 0.47 g solid product. NMR analysis indicated a structure consistent with 6-(4-methoxyphenyl)-6-(4-butoxyphenyl)-9,9-dimethyl-1-hydroxy-11-trifluoromethyl-6H,9H-indeno[2',3':2,1]phenanthro[4,3-b]pyran.

Step 2

The procedure from Example 8 was followed except that and equimolar amount of the product from Step 1 was used

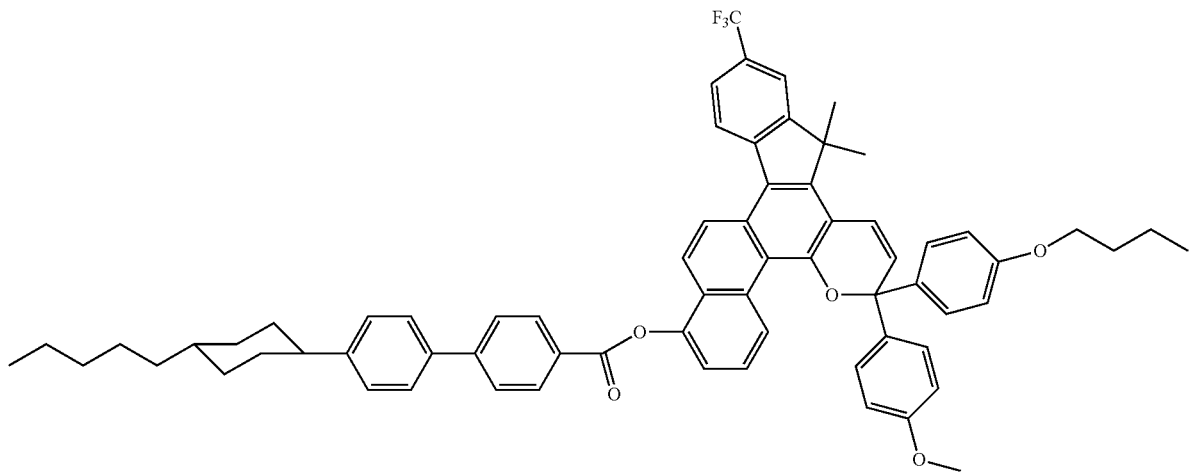 [SMILES: CCCCCC1CCC(c2ccc(-c3ccc(C(=O)Oc4cccc5c4ccc4c6c(c7c(c45)OC(c4ccc(OC)cc4)(c4ccc(OCCCC)cc4)C=C7)C(C)(C)c4cc(C(F)(F)F)ccc4-6)cc3)cc2)CC1]

in place of the product from Example 1. NMR analysis indicated a structure consistent with 6-(4-methoxyphenyl)-6-(4-butoxyphenyl)-9,9-dimethyl-1-((4'-(trans-4-pentylcyclohexyl)-[1,1'-biphenyl]-4-yl)carbonyloxy)-11-trifluoromethyl-6H,9H-indeno[2',3':2,1]phenanthro[4,3-b]pyran.

Example 10

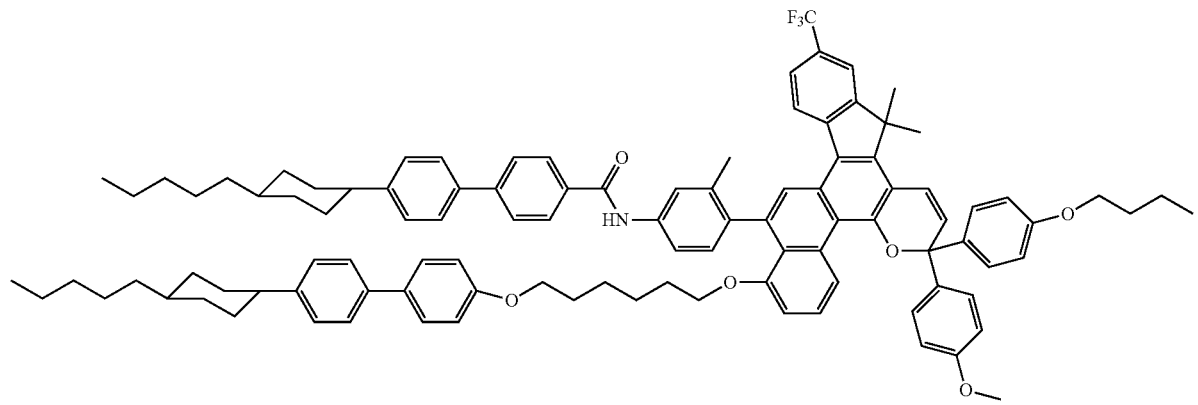 [SMILES: CCCCCC1CCC(c2ccc(-c3ccc(OCCCCCCOc4cccc5c4c(-c4ccc(NC(=O)c6ccc(-c7ccc(C8CCC(CCCCC)CC8)cc7)cc6)cc4C)cc4c6c(c7c(c45)OC(c4ccc(OC)cc4)(c4ccc(OCCCC)cc4)C=C7)C(C)(C)c4cc(C(F)(F)F)ccc4-6)cc3)cc2)CC1]

The product from Example 6 (0.6 g) and N-(3-methyl-4-(4,4,5,5-tetramethyl-1,3,2-dioxaborolan-2-yl)phenyl)-4'-(4-pentylcyclohexyl)[1,1'-biphenyl]-4-carboxamide (0.435 g) were dissolved in tetrahydrofuran (40.0 mL), to which a solution of potassium fluoride (0.2 g) in water (27.0 mL) was added. The solution was degassed by bubbling nitrogen for 10 minutes, dichlorobis(triphenylphosphine)palladium(II) (0.04 g) was added, and the mixture was heated at reflux for 18 hours. The mixture was then cooled to room temperature, poured into water (50 mL) and extracted with ethyl acetate (100.0 mL). The organic solution was separated, washed with brine, dried over anhydrous sodium sulfate, filtered, concentrated under vacuum, and was purified by silica gel chromatography, eluting with a 9:1 (v:v) hexanes to ethyl acetate mixture. Fractions containing the desired material were grouped, and the concentrated residue was dissolved in ethyl acetate (5 mL) and precipitated into methanol (40 mL) to yield 0.35 g solid product. NMR analysis indicated a structure consistent with 6-(4-methoxyphenyl)-6-(4-butoxyphenyl)-9,9-dimethyl-1-((6-((4'-(trans-4-pentylcyclohexyl)-[1,1'-biphenyl]-4-yl)oxy)hexyl)oxy)-15-(2-methyl-(4-(4'-(trans-4-pentylcyclohexyl)-[1,1'-biphenyl]-4-yl)carboxamido)phenyl)-11-trifluoromethyl-6H,9H-indeno[2',3':2,1]phenanthro[4,3-b]pyran.

Example 11

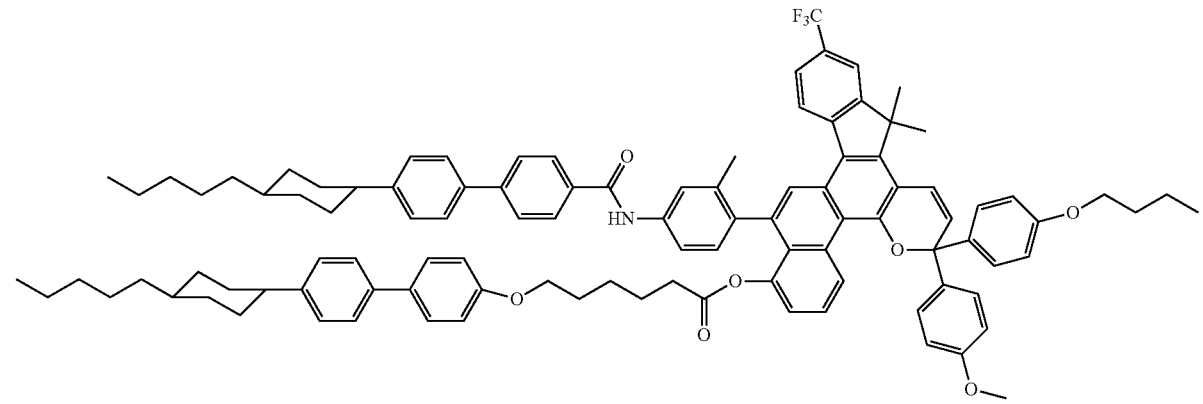 [SMILES: CCCCCC1CCC(c2ccc(-c3ccc(OCCCCCC(=O)Oc4cccc5c4c(-c4ccc(NC(=O)c6ccc(-c7ccc(C8CCC(CCCCC)CC8)cc7)cc6)cc4C)cc4c6c(c7c(c45)OC(c4ccc(OC)cc4)(c4ccc(OCCCC)cc4)C=C7)C(C)(C)c4cc(C(F)(F)F)ccc4-6)cc3)cc2)CC1]

The procedure from Example 10 was followed except that an equimolar amount of the product from Example 7 was used in place of the product from 6. NMR analysis indicated a structure consistent with 6-(4-methoxyphenyl)-6-(4-butoxyphenyl)-9,9-dimethyl-1-(5-((4'-(trans-4-pentylcyclohexyl)-[1,1'-biphenyl]-4-yl)oxy)pentylcarbonyloxy)-15-(2-methyl-(4-(4'-(trans-4-pentylcyclohexyl)-[1,1'-biphenyl]-4-yl)carboxamido)phenyl)-11-trifluoromethyl-6H,9H-indeno[2',3':2,1]phenanthro[4,3-b]pyran.

Example 12

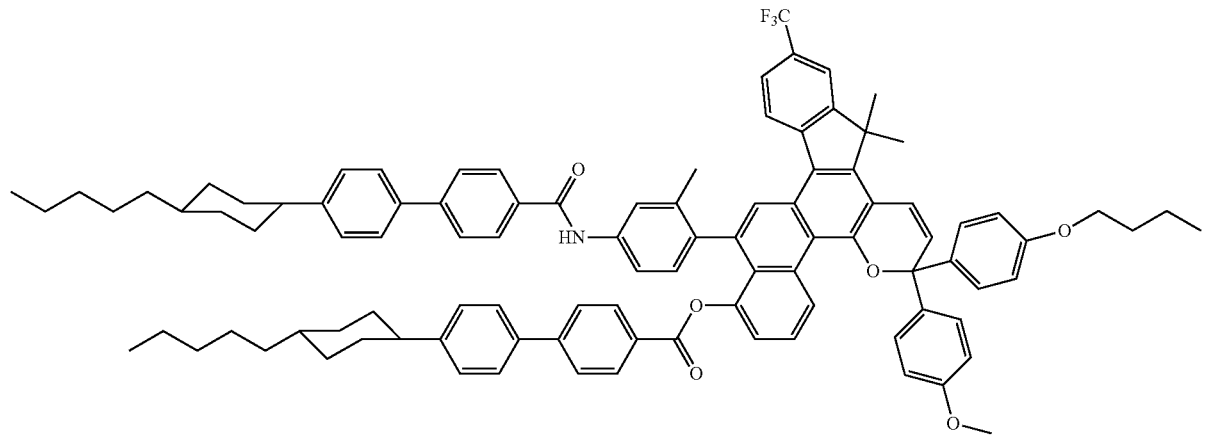 [SMILES: CCCCCC1CCC(c2ccc(-c3ccc(C(=O)Nc4ccc(-c5cc6c7c(c8c(c6c6cccc(OC(=O)c9ccc(-c%10ccc(C%11CCC(CCCCC)CC%11)cc%10)cc9)c56)OC(c5ccc(OC)cc5)(c5ccc(OCCCC)cc5)C=C8)C(C)(C)c5cc(C(F)(F)F)ccc5-7)c(C)c4)cc3)cc2)CC1]

The procedure from Example 10 was followed except that an equimolar amount of the product from Example 8 was used in place of the product from Example 6. NMR analysis indicated a structure consistent with 6-(4-methoxyphenyl)-6-(4-butoxyphenyl)-9,9-dimethyl-1-((4'-(trans-4-pentylcyclohexyl)-[1,1'-biphenyl]-4-yl)carbonyloxy)-15-(2-methyl-(4-(4'-(trans-4-pentylcyclohexyl)-[1,1'-biphenyl]-4-yl)carboxamido)phenyl)-11-trifluoromethyl-6H,9H-indeno[2',3':2,1]phenanthro[4,3-b]pyran.

Example 13

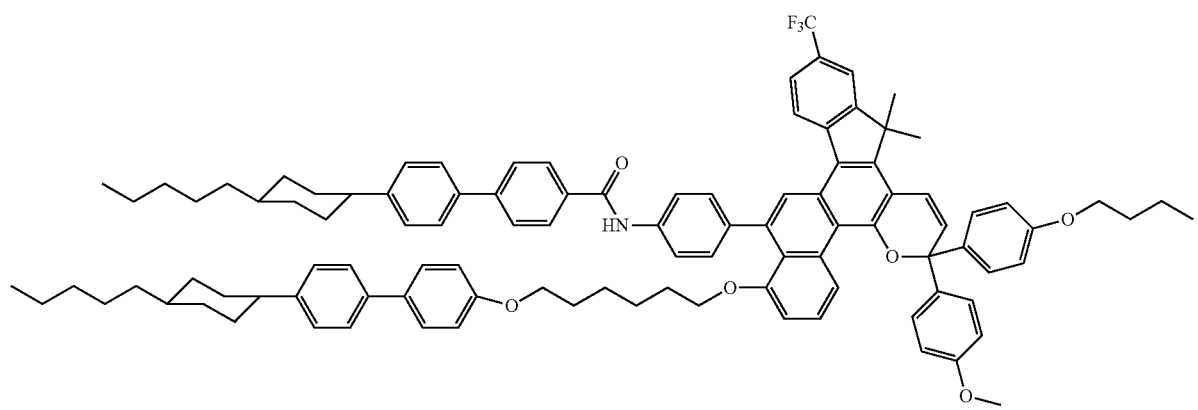 [SMILES: CCCCCC1CCC(c2ccc(-c3ccc(OCCCCCCOc4cccc5c4c(-c4ccc(NC(=O)c6ccc(-c7ccc(C8CCC(CCCCC)CC8)cc7)cc6)cc4)cc4c6c(c7c(c45)OC(c4ccc(OC)cc4)(c4ccc(OCCCC)cc4)C=C7)C(C)(C)c4cc(C(F)(F)F)ccc4-6)cc3)cc2)CC1]

The procedure from Example 10 was followed except that an equimolar amount of N-(4-(4,4,5,5-tetramethyl-1,3,2-dioxaborolan-2-yl)phenyl)-4'-(4-pentylcyclohexyl)[1,1'-biphenyl]-4-carboxamide was used in place of N-(3-methyl-4-(4,4,5,5-tetramethyl-1,3,2-dioxaborolan-2-yl)phenyl)-4'-(4-pentylcyclohexyl)[1,1'-biphenyl]-4-carboxamide. NMR analysis indicated a structure consistent with 6-(4-methoxyphenyl)-6-(4-butoxyphenyl)-9,9-dimethyl-1-((6-((4'-(trans-4-pentylcyclohexyl)-[1,1'-biphenyl]-4-yl)oxy)hexyl)oxy)-15-((4-(4'-(trans-4-pentylcyclohexyl)-[1,1'-biphenyl]-4-yl)carboxamido)phenyl)-11-trifluoromethyl-6H,9H-indeno[2',3':2,1]phenanthro[4,3-b]pyran.

Example 14

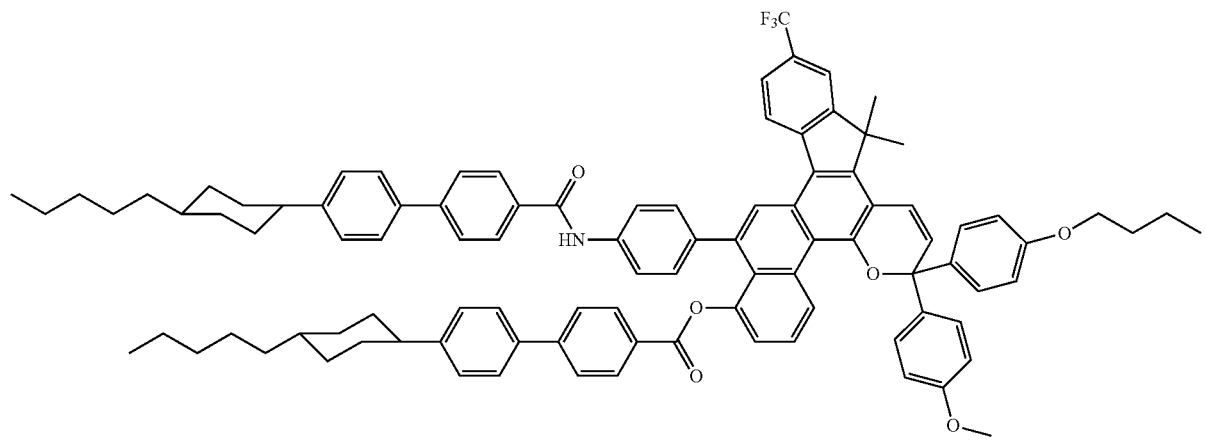 [SMILES: CCCCCC1CCC(c2ccc(-c3ccc(C(=O)Nc4ccc(-c5cc6c7c(c8c(c6c6cccc(OC(=O)c9ccc(-c%10ccc(C%11CCC(CCCCC)CC%11)cc%10)cc9)c56)OC(c5ccc(OC)cc5)(c5ccc(OCCCC)cc5)C=C8)C(C)(C)c5cc(C(F)(F)F)ccc5-7)cc4)cc3)cc2)CC1]

The procedure from Example 12 was followed except that an equimolar amount of N-(4-(4,4,5,5-tetramethyl-1,3,2-dioxaborolan-2-yl)phenyl)-4'-(4-pentylcyclohexyl)[1,1'-biphenyl]-4-carboxamide was used in place of N-(3-methyl-4-(4,4,5,5-tetramethyl-1,3,2-dioxaborolan-2-yl)phenyl)-4'-(4-pentylcyclohexyl)[1,1'-biphenyl]-4-carboxamide. NMR analysis indicated a structure consistent with 6-(4-methoxyphenyl)-6-(4-butoxyphenyl)-9,9-dimethyl-1-((4'-(trans-4-pentylcyclohexyl)-[1,1'-biphenyl]-4-yl)carbonyloxy)-15-((4-(4'-(trans-4-pentylcyclohexyl)-[1,1'-biphenyl]-4-yl)carboxamido)phenyl)-11-trifluoromethyl-6H,9H-indeno[2',3':2,1]phenanthro[4,3-b]pyran.

Example 15

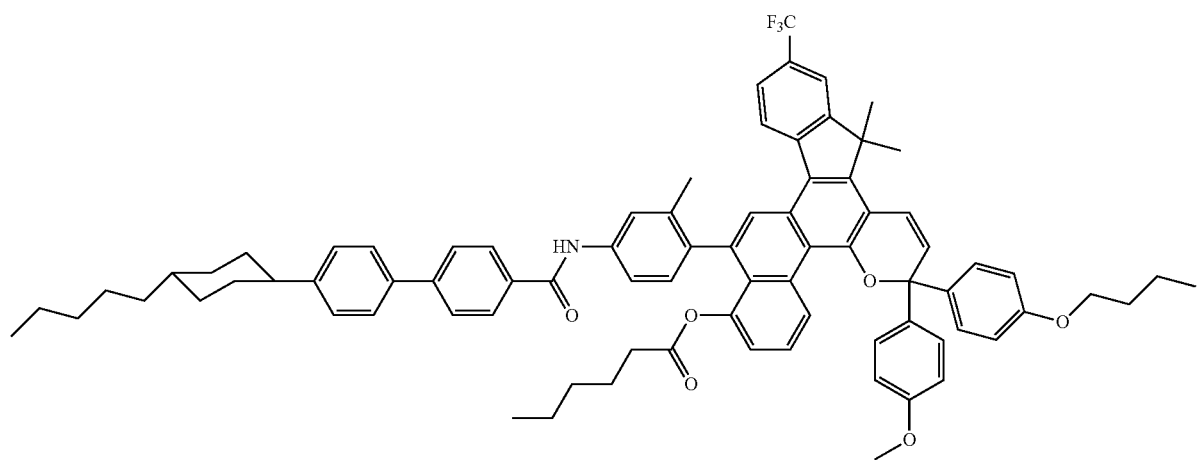 [SMILES: CCCCCC(=O)Oc1cccc2c1c(-c1ccc(NC(=O)c3ccc(-c4ccc(C5CCC(CCCCC)CC5)cc4)cc3)cc1C)cc1c3c(c4c(c12)OC(c1ccc(OC)cc1)(c1ccc(OCCCC)cc1)C=C4)C(C)(C)c1cc(C(F)(F)F)ccc1-3]

Step 1

The product from Example 1 (1.25 g) and trimethylamine (0.91 mL) were dissolved in dichloromethane (25 mL), and the solution was cooled with an ice water bath for 15 minutes. Hexanoyl chloride (0.69 mL was added, then the ice water bath was removed. After stirring at for 12 hours, water (25 mL) was added. The organic phase was separated, dried with anhydrous sodium sulfate, concentrated, and the residue was purified by CombiFlash chromatography, eluting with a 9:1 (v:v) hexane to ethyl acetate mixture, to yield 1 g solid product. NMR analysis indicated a structure consistent with 6-(4-methoxyphenyl)-6-(4-butoxyphenyl)-9,9-dimethyl-1-pentylcarbonyloxy-15-bromo-11-trifluoromethyl-6H,9H-indeno[2',3':2,1]phenanthro[4,3-b]pyran.

Step 2

The procedure from Example 10 was followed except that an equimolar amount of the product from Step 1 was used in place of the product from Example 6. NMR analysis indicated a structure consistent with 6-(4-methoxyphenyl)-6-(4-butoxyphenyl)-9,9-dimethyl-1-pentylcarbonyloxy-15-(2-methyl-(4-(4'-(trans-4-pentylcyclohexyl)-[1,1'-biphenyl]-4-yl)carboxamido)phenyl)-11-trifluoromethyl-6H,9H-indeno[2',3':2,1]phenanthro[4,3-b]pyran.

Comparative Example CE16

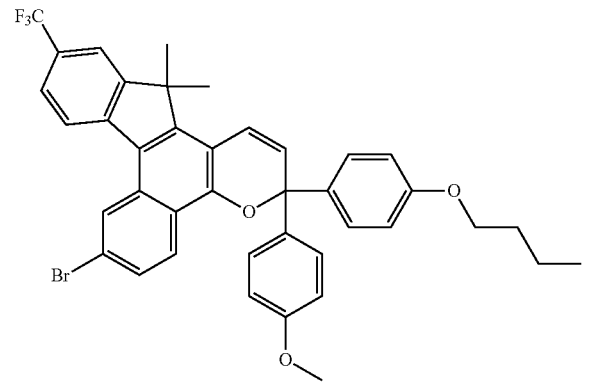 [SMILES: CCCCOc1ccc(C2(c3ccc(OC)cc3)C=Cc3c4c(c5cc(Br)ccc5c3O2)-c2ccc(C(F)(F)F)cc2C4(C)C)cc1]

The product from the Example 1, Step 6, (3.114 g) was dissolved in anhydrous THF (30 mL) then cooled in a dry ice-acetone bath for 10 minutes. n-BuLi solution in hexane (1.15 eq) was added dropwise. After stirring for 5 minutes, brine was added and the mixture was warmed to room temperature. The organic phase was separated, dried with anhydrous sodium sulfate, concentrated, and then purified by CombiFlash column chromatography, eluting with a 2:1 (v:v) hexane to dichloromethane mixture, to yield 1.9 g of solid product. NMR analysis indicated a structure consistent with 3-(4-methoxyphenyl)-3-(4-butoxyphenyl)-7-bromo-11-trifluoromethyl-13,13-dimethyl-3,13-dihydro-indeno[2',3':3,4]naphtho[1,2-b]pyran.

Comparative Example CE17

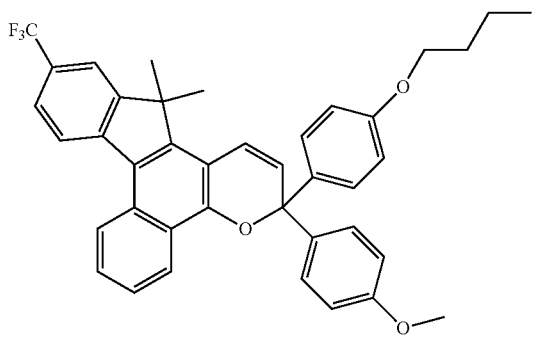 [SMILES: CCCCOc1ccc(C2(c3ccc(OC)cc3)C=Cc3c4c(c5ccccc5c3O2)-c2ccc(C(F)(F)F)cc2C4(C)C)cc1]

The procedure from Comparative Example 16 was followed except that 2.5 equivalent of n-BuLi was used. NMR analysis indicated a structure consistent with 3-(4-methoxyphenyl)-3-(4-butoxyphenyl)-11-trifluoromethyl-13,13-dimethyl-3,13-dihydro-indeno[2',3':3,4]naphtho[1,2-b]pyran.

Comparative Example CE18

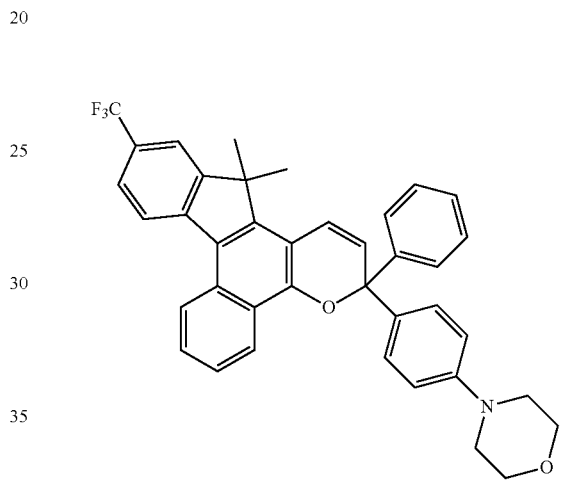

Step 1

The procedure from Example 1, Step 6 was followed except that an equimolar amount of 1-(4-morpholinophenyl)-1-phenyl-prop-2-yn-1-ol was used in place of 1-(4-butoxyphenyl)-1-(4-methoxyphenyl)-prop-2-yn-1-ol. NMR analysis indicated a structure consistent with 3-(4-morpholinophenyl)-3-phenyl-5,7-dibromo-11-trifluoromethyl-13,13-dimethyl-3,13-dihydro-indeno[2',3':3,4]naphtho[1,2-b]pyran.

Step 2

The procedure from Example 17 was followed except that an equimolar amount of the product from Step 1 was used in place of the product from Example 1, Step 6. NMR analysis indicated a structure consistent with 3-(4-morpholinophenyl)-3-phenyl-11-trifluoromethyl-13,13-dimethyl-3,13-dihydro-indeno[2',3':3,4]naphtho[1,2-b]pyran.

Comparative Example CE19

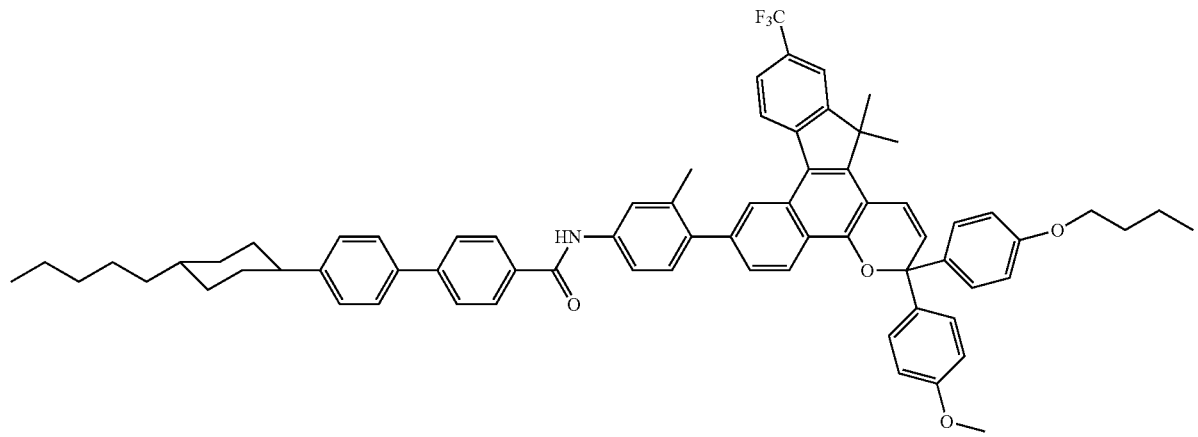 [SMILES: CCCCCC1CCC(c2ccc(-c3ccc(C(=O)Nc4ccc(-c5ccc6c7c(c8c(c6c5)-c5ccc(C(F)(F)F)cc5C8(C)C)C=CC(c5ccc(OC)cc5)(c5ccc(OCCCC)cc5)O7)c(C)c4)cc3)cc2)CC1]

The procedure from Example 10 was followed except that an equimolar amount of the product from Example 1, Step 6, was used in place of the product from Example 6. NMR analysis indicated a structure consistent with 3-(4-butoxyphenyl)-3-(4-methoxyphenyl)-7-(2-methyl-(4-(4'-(trans-4-pentylcyclohexyl)-[1,1'-biphenyl]-4-yl)carboxamido)phenyl)-11-trifluoromethyl-13,13-dimethyl-3,13-dihydroindeno[2',3':3,4]naphtho[1,2-b]pyran.

Comparative Example CE20

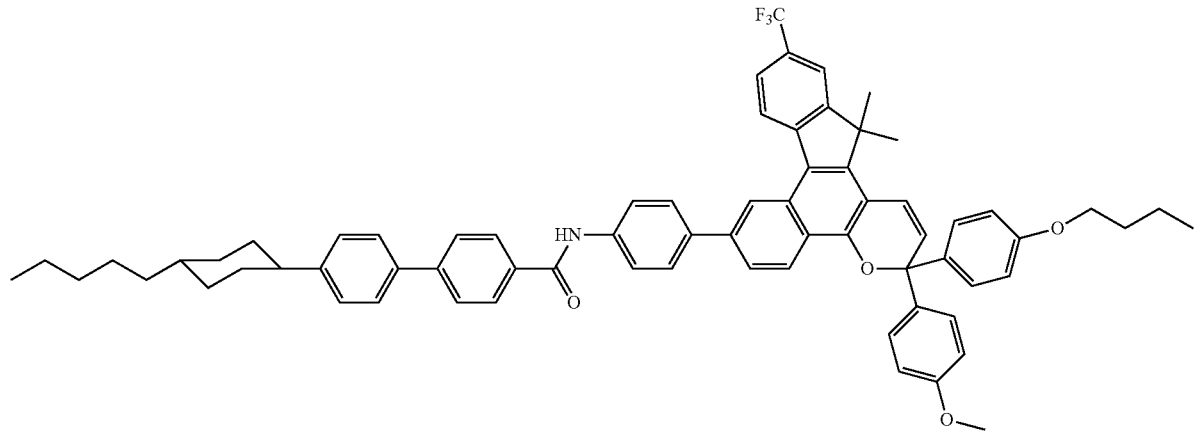 [SMILES: CCCCCC1CCC(c2ccc(-c3ccc(C(=O)Nc4ccc(-c5ccc6c7c(c8c(c6c5)-c5ccc(C(F)(F)F)cc5C8(C)C)C=CC(c5ccc(OC)cc5)(c5ccc(OCCCC)cc5)O7)cc4)cc3)cc2)CC1]

The procedure from Example 10 was followed except that an equimolar amount of the product from Comparative Example 16 was used in place of the product from Example 6 and an equimolar amount of N-(4-(4,4,5,5-tetramethyl-1,3,2-dioxaborolan-2-yl)phenyl)-4'-(4-pentylcyclohexyl)[1,1'-biphenyl]-4-carboxamide was used in place of N-(3-methyl-4-(4,4,5,5-tetramethyl-1,3,2-dioxaborolan-2-yl)phenyl)-4'-(4-pentylcyclohexyl)[1,1'-biphenyl]-4-carboxamide. NMR analysis indicated a structure consistent with 3-(4-butoxyphenyl)-3-(4-methoxyphenyl)-7-((4-(4'-(trans-4-pentylcyclohexyl)-[1,1'-biphenyl]-4-yl)carboxamido)phenyl)-11-trifluoromethyl-13,13-dimethyl-3,13-dihydro-indeno[2',3':3,4]naphtho[1,2-b]pyran.

Part 2: Photochromic Properties

Part 2A—Preparation of Photochromic Test Squares

Testing was done with the compounds described in Examples 1-6, 10, and CE16-CE20 in the following manner. A quantity of compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methylpropionitrile). Each compound was dissolved into the monomer blend by stirring and gentle heating, if necessary. After a clear solution was obtained, the sample was degassed in a vacuum oven for 5-10 minutes at 25 torr. Using a syringe, the sample was poured into a flat sheet mold having an interior dimension of 2.2 mm+/−0.3 mm×6 inch (15.24 cm)×6 inch (15.24 cm). The mold was sealed and placed in a horizontal airflow, programmable oven set to ramp from 40° C. to 95° C. over 5 hours, hold the temperature at 95° C. for 3 hours, ramp down to 60° C. over 2 hours then hold at 60° C. for 16 hours. After curing, the mold was opened, and the polymer sheet was cut into 2 inch (5.1 cm) test squares using a diamond blade saw.

Part 2B—Photochromic Response Testing

Prior to response testing on an optical bench, the test squares from Part 2A were conditioned by exposing them to 365 nm ultraviolet light for 10 minutes at a distance of about 10 cm from the source in order to pre-activate the photochromic compounds in the samples. The UVA irradiance at the sample surface was measured with a Licor Model Li-1800 spectroradiometer and found to be 13.6 W/m². The samples were then placed under a halogen lamp (500 W, 120V) for about 10 minutes at a distance of about 30 cm from the lamp in order to bleach, or inactivate, the photochromic compounds in the samples. The illuminance at the sample was measured with the Licor spectroradiometer and found to be 47 Klux. The samples were then placed under a yellow fluorescent lamp (12 W, 120V) for about 30 minutes at a distance of about 10 cm from the lamp in order to further bleach, or inactivate, the photochromic compounds in the samples. The illuminance at the sample was measured with the Licor spectroradiometer and found to be 17 Klux. The samples were then kept in a dark environment for at least 1 hour prior to testing in order to cool and continue to fade back to a ground state.

The optical bench was fitted with a Newport Model #67005 300 W Xenon arc lamp and Model 69911 power supply, a Vincent Associates (Model VS25S2ZM0R3 with VMM-D4 controller) high-speed computer controlled shutter, a Schott 3 mm KG-2 band-pass filter, which removed short wavelength radiation, a neutral density filter(s) to attenuate light from the xenon lamp, a fused silica condensing lens for beam collimation, and a fused silica water cell/sample holder for maintaining sample temperature in which the test sample to be tested was inserted. The temperature in the water cell was controlled with a pumped water circulation system in which the water passed through copper coils that were placed in the reservoir of a chiller unit. The water cell used to hold test samples contained fused silica sheets on the front and back facings in order to eliminate spectral change of the activation or monitoring light beams. The filtered water passing through the water cell was maintained at 23° C.±0.2° C. for photochromic response testing. A Newport Model 68945 Digital Exposure Timer was used to further control the intensity of the xenon arc lamp during activation of the sample.

A custom broadband halogen light source for monitoring response measurements was positioned in a perpendicular manner to a surface of the cell assembly. Increased signal of shorter visible wavelengths was obtained from a 100 W tungsten halogen lamp (controlled via a TDK-Lambda Zup36-12 power supply) by collecting and re-combining separately filtered light through a bifurcated fiber assembly. This monitoring light, after passing through the sample, was refocused into a 2-inch integrating sphere and fed to an Ocean Optics S2000 spectrophotometer by fiber optic cables. Ocean Optics SpectraSuite and PPG proprietary software were used to measure response and control the operation of the optical bench.

Irradiance for response testing of the samples on the optical bench was established at the sample surface using an International Light Research Radiometer, Model IL-1700 with a detector system comprising a Model SED033 detector, B Filter and diffuser. The output display of the radiometer was corrected (factor values set) against a Licor 1800-02 Optical Calibration Calibrator in order to display values representing W/m² UVA. The irradiance at the sample point for initial response testing was set at to 3.0 W/m² UVA and approximately 8.6 Klux illuminance. During sample response testing, if a sample darkened beyond an acceptable detection capability limit, the irradiance was lowered to 1.0 W/m² UVA or the sample was remade at a one-half concentration in the copolymer. Adjusting the output of the filtered xenon arc lamp was accomplished by increasing or decreasing the current to the lamp through the controller and/or by adding or removing neutral density filters in the light path. The test samples were exposed to the activation light at a 31° angle normal to its surface while being perpendicular to the monitoring light.

Samples were activated in the 23° C. controlled water cell for 30 minutes, then allowed to fade under room light conditions until the change in optical density of the activated sample faded to ⅛ of its highest darkened (saturated) state or for a maximum of 30 minutes of fade.

The $\lambda_{max\text{-}vis}$ is the wavelength in the visible spectrum at which the maximum absorption of the activated form of the photochromic compound occurs. The $\lambda_{max\text{-}vis}$ was determined by testing the activated photochromic test square in a Varian Cary 4000 UV-Visible spectrophotometer or comparable equipment.

The change in optical density (ΔOD) from the bleached state to the darkened state was determined by establishing the initial transmittance, opening the shutter from the Xenon lamp to provide ultraviolet radiation to change the test lens from the bleached state to an activated (i.e., darkened) state. Data was collected at selected intervals of time, measuring the transmittance in the activated state, and calculating the change in optical density according to the formula: ΔOD=log(% Tb/% Ta), where % Tb is the percent transmittance in the bleached state, % Ta is the percent transmittance in the activated state and the logarithm is to the base 10.

The saturation optical density (ΔOD at saturation) is recorded after 30 minutes of activation. The fade half-life is the time interval in seconds for the ΔOD of the activated form of the photochromic compound in the test squares to reach one half this ΔOD measured after thirty minutes, after removal of the source of activating light, e.g., by closing the shutter. Beached Y is the Y tri-stimulus value of the CIE XYZ prior to activation of the sample. Results are listed in Table 1.

TABLE 1

Photochromic Performance Test Results.

| Example # | $\lambda_{max\text{-}vis}$ (nm) | ΔOD at saturation | Fade T½ (sec) | Bleach Y |
|---|---|---|---|---|
| 1 | 517 | 0.18 | 19 | 82.0 |
| 2 | 506 | 0.41 | 42 | 82.5 |
| 3 | 613 | 0.14 | 42 | 75.2 |
| 4 | 490 | 0.33 | 49 | 89.7 |
|   | 572 | 0.24 | 49 |   |
| 5 | 601 | 0.23 | 36 | 88.2 |
| 6 | 514 | 0.16 | 15 | 88.7 |
| 10 | 506 | 0.46 | 138 | 85.7 |
| CE16 | 561 | 0.22 | 24 | 87.2 |
| CE17 | 555 | 0.45 | 50 | 87.1 |
| CE18 | 593 | 0.59 | 86 | 73.1 |
| CE19 | 556 | 0.43 | 65 | 80.6 |
| CE20 | 558 | 0.49 | 61 | 84.7 |

Part 3—Dichroic Property Testing-Liquid Crystal Cells
Part 3A—Liquid Crystal Cell Preparation The average absorption ratio of each of the compounds of Examples 6-12, 14-15, and CE19-20 was determined according to the CELL METHOD described as follows.

A cell assembly having the following configuration was obtained from Design Concepts, Inc. Each of the cell assemblies was formed from two opposing glass substrates that are spaced apart with a glass bead spacer having a diameter of 20 microns+/−1 micron. The inner surfaces of each of the glass substrates had oriented polyimide coating thereon to provide for the alignment of a liquid crystal material as discussed below. Two opposing edges of the glass substrates were sealed with an epoxy sealant, leaving the remaining two edges open for filling.

The gap between the two glass substrates of the cell assembly was filled with a liquid crystal solution containing the one of the compounds of Examples 6-12, 14-15, and CE19-20. The liquid crystal solution was formed by mixing the following components in the weight percentages listed in Table 2 with heating, if necessary, to dissolve the test material.

TABLE 2

Weight Percentages of Components in Liquid Crystal Solution.

| Material | Weight Percent |
| --- | --- |
| LICRISTAL ™ E7[1] liquid crystal | 97-99.5 |
| Example Compound | 0.5-3 |

[1]A liquid crystal available from EMD Performance Materials.

Part 3B—Liquid Crystal Cell Testing

An optical bench was used to measure the optical properties of the cell and derive the absorption ratios for each of the Test Materials. The filled cell assembly was placed on the optical bench with an activating light source (a Newport Model #67005 300 W Xenon arc lamp and Model 69911 power supply fitted with a Vincent Associates (model VS25S2ZM0R3 with VMM-D4 controller) high-speed computer controlled shutter that momentarily closed during data collection so that stray light would not interfere with the data collection process, a Schott 3 mm KG-1 band-pass filter, which removed short wavelength radiation, neutral density filter(s) for intensity attenuation and a condensing lens for beam collimation) positioned at a 31° angle of incidence a surface of the cell assembly.

A broadband light source similar to that described Part 2B for monitoring response measurements was positioned perpendicular to a surface of the cell assembly.

Polarization of the broadband light source was achieved by passing the light from the single end of the fiber through a Moxtek, Proflux Polarizer held in a computer driven, motorized rotation stage (Model M-061-PD from Polytech, PI). The monitoring beam was set such that the one polarization plane (0°) was perpendicular to the plane of the optical bench table and the second polarization plane (90°) was parallel to the plane of the optical bench table. The samples were run at 23° C.±0.1° C. maintained by a temperature controlled air cell.

To conduct the measurements, the cell assembly and the coating stack were exposed to 5.6 W/m² of UVA from the activating light source for 15 minutes to activate the Test Material. An International Light Research Radiometer (Model IL-T950) was used to verify exposure prior to each test. Light from the monitoring source that was polarized to the 0° polarization plane was then passed through the coated sample and focused on a 1" integrating sphere, which was connected to an Ocean Optics S2000 spectrophotometer using a single function fiber optic cable. The spectral information, after passing through the sample, was collected using Ocean Optics Spectraphotometer and Spectrasuite and propriety operation software. While the photochromic-dichroic material was activated, the position of the polarizer was rotated back and forth to polarize the light from the monitoring light source to the 90° polarization plane and back. For each test, rotation of the polarizers was adjusted to collect data in the following sequence of polarization planes: 0°, 90°, 90°, 0°, etc.

The resulting absorption spectra were analyzed for each cell assembly using Igor Pro software (available from WaveMetrics). The change in the absorbance in each polarization direction for each cell assembly was calculated by subtracting out the 0 time (i.e., unactivated) absorption measurement for the cell assembly at each wavelength tested. The average absorbance values in a predetermined range of wavelengths corresponding $\lambda_{max-vis}$+/−5 nm were extracted for the 0° and 90° polarizations, and the absorption ratio for each wavelength in this range was calculated by dividing the larger average absorbance by the small average absorbance.

The tabled value for the Average Absorption Ratio represents an average of at least two runs measured at the wavelength indicated. The results of these tests are present in Table 3 below.

TABLE 3

Absorption Ratio Test Data.

| Example # | $\lambda_{max-vis}$ (nm) | Absorption Ratio |
| --- | --- | --- |
| 6 | 511 | 1.57 |
| 7 | 595 | 1.44 |
| 8 | 595 | 5.17 |
| 9 | 584 | 5.84 |
| 10 | 511 | 7.41 |
| 11 | 485 | 7.92 |
| 12 | 485 | 9.89 |
| 14 | 490 | 9.86 |
| 15 | 486 | 6.47 |
| CE19 | 556 | 7.03 |
| CE20 | 556 | 6.96 |

Part 4 Aligned Coating stacks

Part 4A—Preparation of Coating Solutions

Primer

Into a suitable container equipped with a magnetic stir-bar the following materials were added in the amounts indicated in Table 4.

TABLE 4

Parts by Weight of Components in Primer.

| Name | Parts by weight |
| --- | --- |
| Polyacrylate polyol[1] | 3.24 |
| POLYMEG ® 1000[2] polytetramethylene ether glycol | 8.395 |
| DESMODUR ® PL 340[3] polyisocyanate | 10.885 |
| TRIXENE ® BI 7960[4] polyisocyanate | 7.762 |
| BYK ®-333[5] polyether | 0.017 |
| K-KAT ® 348[6] metal catalyst | 0.28 |
| γ-Glycidoxypropyltrimethoxysilane | 0.902 |
| TINUVIN ® 144[7] light stabilizer | 0.380 |

TABLE 4-continued

Parts by Weight of Components in Primer.

| Name | Parts by weight |
| --- | --- |
| IRGANOX 245[8] light stabilizer | 0.380 |
| DOWANOL ® DPMA[9] glycol ether acetate | 16.672 |

[1]Composition D of Example 1 in U.S. Pat. No. 6,187,444 except that in Charge 2, the styrene was replaced with methyl methacrylate and 0.5% by weight, based on the total monomer weight, of triphenyl phosphite was added.
[2]A polytetramethylene ether glycol obtained commercially from Great Lakes Chemical Corp.
[3]An isophoronediisocyanate based polyisocyanate obtained commercially from Bayer Material Science.
[4]A hexamethylenediisocyanate biuret polyisocyanate obtained commercially from Baxenden Chemicals Ltd.
[5]A polyether modified polydimethylsiloxane obtained commercially from BYK-Chemie, USA.
[6]A bismuth carboxylate catalyst obtained commercially from King Industries.
[7]A light stabilizer obtained commercially from Ciba Specialty Chemicals.
[8]A light stabilizer obtained commercially from Ciba Specialty Chemicals.
[9]Dipropylene glycol methyl ether acetate (DMPA) obtained commercially from Dow Chemical.

The components of Table 4 were stirred at room temperature for 2 hours to yield a solution having 50% final solids based on the total weight of the solution.

Photo-Alignment Coating Solution

The photoalignment material described in Example 1 of U.S. Pat. No. 9,475,901 B2 was diluted to a 6% solution in cyclopentanone.

Liquid Crystal Coating Formulation (LCCF)

A liquid crystal coating formulation (LCCF) was prepared by combining the materials shown in Table 5.

TABLE 5

Liquid Crystal Coating Formulation Components.

| Name | Parts by weight |
| --- | --- |
| Anisole | 19.50 |
| BYK ®-322[1] siloxane | 0.02 |
| Liquid Crystal Monomer (LCM)-1[2] | 12.6 |
| LCM-2[3] | 6.6 |
| LCM-3[4] | 5.40 |
| LCM-4[5] | 5.40 |
| 4-Methoxyphenol | 0.03 |
| IRGACURE ® 819[6] photoinitiator | 0.45 |

[1]An aralkyl modified poly-methyl-alkyl-siloxane from BYK Chemie, USA.
[2]RM257, reported to be 4-(3-acryloyloxypropyloxy)-benzoic acid 2-methyl-1,4-phenylene ester, commercially available from EMD Chemicals, Inc.
[3]1-(6-(6-(6-(6-(6-(6-(6-(8-(4-(4-hexyloxy-benzoyloxy)phenoxycarbonyl)-phenoxy)octyloxy)-6-oxohexyloxy)-6-oxohexyloxy)-6-oxohexyloxy)-6-oxohexyloxy)-6-oxohexyloxy)-6-oxohexyloxy)-2-methylprop-2-en-1-one prepared according to the procedures of U.S. Pat. No. 7,910,019 B2.
[4]1-(6-(8-(4-(4-(4-(8-acryloyloxyhexyl)oxy)benzoyloxy)phenyloxycarbonyl)phenoxy) octyloxy)-6-oxohexyloxy)-6-oxohexyloxy)-6-oxohexyloxy)-6-oxohexyloxy)-6-oxohexyloxy)-6-oxohexan-1-ol which was prepared according to the procedure of Example 17 in International Publication No. WO 2009/158483 A1.
[5]1-(6-(4-(4-(trans-4-pentylcyclohexyl)phenoxy-carbonyl)phenoxy)hexyloxy)-2-methylprop-2-en-1-one, which was prepared according to the procedure of Example 1 in U.S. Pat. No. 7,910,019 B2, except that n = 0.
[6]Bis(2,4,6-trimethylbenzoyl)-phenylphosphineoxide photoinitiator from BASF, The Chemical Company.

The components of Table 5 were stirred for 2 hours at 80° C. and then cooled to room temperature. A portion of the resultant mixture was then added to a small amber vial containing the photochromic compound of Example 9 to produce a concentration of 6.3 mmol photochromic compound per 100 g of final solution, which was scaled to produce 5.0 g of final solution. Upon addition of the photochromic compound, the formulation was stirred at 60° C. until the photochromic compound was fully incorporated. This was repeated individually for Examples 10 and 15.

Part 4B—Preparation of Aligned Coating Stacks

Step 1: Substrate Preparation

Square substrates measuring 5.08 cm by 5.08 cm by 0.318 cm (2 inches (in.) by 2 in. by 0.125 in.) prepared from CR-39® monomer were obtained from Homalite, Inc. Each substrate was cleaned by wiping with a tissue soaked with acetone and dried with a stream of air.

Each of the cleaned substrates was corona treated using Tantec EST Systems Serial No. 020270 Power Generator HV 2000 series corona treatment equipment with a high voltage transformer. The substrates were exposed to corona generated by 53.99 KV, 500 W while traveling on a conveyor at a belt speed 3 ft/min.

Step 2: Coating Procedure for Primer

The primer solution was applied to the test substrates by spin-coating on a portion of the surface of the test substrate by dispensing approximately 1.5 mL of the solution and spinning the substrates at 975 revolutions per minute (rpm) for 4 seconds, followed by 1,500 rpm for 2 seconds, followed by 2,500 rpm for 1 second. A bench-mounted ATC topside coater from Brillhart Industries was used for spin coating. Afterwards, the coated substrates were placed in a forced-air oven maintained at 125° C. for 60 minutes. The coated substrates were cooled to room temperature. The substrate was corona treated by passing on a conveyor belt in Tantec EST Systems Serial No. 020270 Power Generator HV 2000 series corona treatment equipment with a high voltage transformer. The dried primer layers were exposed to corona generated by 70.00 KV, 1000 W while traveling on a conveyor at a belt speed 3 ft/min.

Step 3: Coating and Alignment of Photo-Alignment Material

The photo-alignment coating solution prepared above was applied to the test substrates by spin-coating on a portion of the surface of the test substrate by dispensing approximately 1.0 mL of the solution and spinning the substrates at 800 revolutions per minute (rpm) for 3 seconds, followed by 1,000 rpm for 7 seconds, followed by 2,500 rpm for 4 seconds. Afterwards, the coated substrates were placed in an oven maintained at 120° C. for 5 minutes followed by shutoff and cool down within the oven for 20 minutes.

The dried photo alignment layer on each of the substrates was at least partially ordered by exposure to linearly polarized ultraviolet radiation using a DYMAX® UVC-6 UV/conveyor system by DYMAX® Corp. having a 400 W power supply. The light source was oriented such that the radiation was linearly polarized in a plane perpendicular to the surface of the substrate. The photoalignment layer exposure was measured using a UV Power Puck™ High energy radiometer from EIT Inc (Serial No. 2066) and was as follows: UVA 0.018 W/cm$^2$ and 5.361 J/cm$^2$; UVB 0 W/cm$^2$ and 0 J/cm$^2$; UVC 0 W/cm$^2$ and 0 J/cm$^2$; and UVV 0.005 W/cm$^2$ and 1.541 J/cm$^2$. After ordering at least a portion of the photo-alignment material, the substrates were cooled to room temperature and kept covered.

Step 4: Coating of Liquid Crystal Coating Formulations

The LCCFs described above were each spin coated over the at least partially ordered photo-alignment layers described in Step 3. Each coated square substrate was placed in a forced-air oven at 60-75° C. for 30 minutes and then held at room temperature for 2 minutes. Afterwards they were cured under two ultraviolet in a nitrogen atmosphere while running on a conveyor belt at 2 ft/min speed at peak intensity of 0.388 W/cm$^2$ of UVA and 0.165 W/cm$^2$ of UVV and UV dosage of 7.386 J/cm$^2$ of UVA and 3.337 J/cm$^2$ of UVV. Finally, the cured samples were exposed to corona generated by 70.00 KV, 1000 W while traveling on a conveyor at a belt speed 3 ft/min.

Step 5: Coating Procedure for Protective Layer

A protective coating composition was prepared in accordance with the formulation disclosed in Table 1 of Example 1 of U.S. Pat. No. 7,410,691 B2 (with an additional 0.5 percent by weight of polybutyl acrylate), and the protective coating composition was applied by spin coating to all of the lenses as a protective coating layer. Afterwards, the lenses were cured under two ultraviolet lamps in a UV Curing Oven Machine designed and built by Belcan Engineering under a nitrogen atmosphere while running on a conveyor belt at 6 ft/min speed at peak intensity of 1.887 W/cm$^2$ of UVA and 0.694 W/cm$^2$ of UVV and UV dosage of 4.699 J/cm$^2$ of UVA and 1.787 J/cm$^2$ of UVV. The samples were then subjected to a post-cure in a forced-air oven at 105° C. for 3 hours.

Part 4C—Testing and Results for Coating Stack

The methods described in Part 3B were used to determine the absorption ratio for each of the tested photochromic compounds in a coating stack. In each case, the substrate with the coating stack was used in place of the liquid crystal cell. The results are summarized in the following Table 6.

TABLE 6

Absorption Ratio for Coating Stacks.

| Example # | $\lambda_{max\text{-}vis}$ (nm) | Absorption Ratio |
|---|---|---|
| 9 | 586 | 2.35 |
| 10 | 503 | 6.37 |
| 15 | 514 | 1.74 |

The present invention can be further characterized by one or more of the following non-limiting clauses 1-20.

Clause 1: A photochromic compound represented by the following Formula (I),

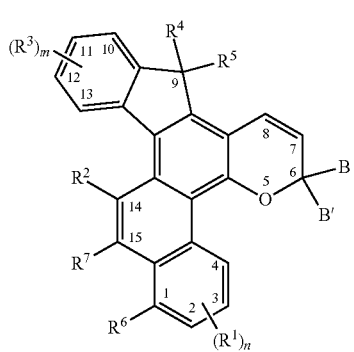

(I)

wherein n is 1 to 3, and m is 1 to 4, $R^2$ is selected from the group consisting of, hydrogen; halogen; linear or branched $C_1$-$C_{20}$ alkyl; linear or branched $C_1$-$C_{20}$ perhaloalkyl; —OR$^a$; —SR$^a$, where each R$^a$ is independently selected from the group consisting of hydrogen, linear or branched $C_1$-$C_{20}$ alkyl, and linear or branched $C_1$-$C_{20}$ perhaloalkyl; —C(O)OR$^b$, where R$^b$ is hydrogen or linear or branched $C_1$-$C_{10}$ alkyl; substituted or unsubstituted aryl, each aryl substituent being independently selected from the group consisting of hydroxyl, halogen, carbonyl, linear or branched $C_1$-$C_{20}$ alkoxycarbonyl, cyano, linear or branched $C_1$-$C_{20}$ haloalkyl, linear or branched $C_1$-$C_{20}$ alkyl, linear or branched $C_1$-$C_{20}$ alkoxy, and linear or branched $C_1$-$C_{20}$ perhaloalkyl; and a group $Y^1$;

$R^6$ and $R^7$ are each independently selected from the group consisting of, hydrogen; halogen; a lengthening group $L^1$; —OR$^c$, and —SR$^c$, where each R$^c$ is independently selected from the group consisting of hydrogen, a lengthening group $L^2$, linear or branched $C_1$-$C_{20}$ alkyl, —C(O)—R$^d$, and —S(O)(O)—R$^e$, where R$^d$ and R$^e$ are each independently selected from the group consisting of linear or branched $C_1$-$C_{10}$ alkyl, linear or branched $C_1$-$C_{10}$ perhaloalkyl, phenyl, linear or branched $C_1$-$C_{10}$ alkyl substituted phenyl, and linear or branched $C_1$-$C_{10}$ perhaloalkyl substituted phenyl, provided that at least one of $R^6$ and $R^7$ is other than hydrogen;

$R^1$ independently for each n, and $R^3$ independently for each m are each independently selected from the group consisting of, hydrogen;

cyano;

a reactive substituent;

a lengthening group $L^3$;

halogen selected from the group consisting of fluoro, chloro, and bromo;

linear or branched $C_1$-$C_{20}$ alkyl;

linear or branched $C_1$-$C_{20}$ perhaloalkyl;

$C_3$-$C_{10}$ cycloalkyl;

a group $Y^2$;

substituted or unsubstituted phenyl, the phenyl substituents being selected from at least one of hydroxyl, halogen, carbonyl, linear or branched $C_1$-$C_{20}$ alkoxycarbonyl, cyano, linear or branched $C_1$-$C_{20}$ haloalkyl, linear or branched $C_1$-$C_{20}$ alkyl, linear or branched $C_1$-$C_{20}$ alkoxy, linear or branched $C_1$-$C_{20}$ perhaloalkyl, and combinations thereof;

—O—R$_{10}$', —S—R$_{10}$', —C(O)—R$_{10}$', —C(O)OR$_{10}$', —OC(O)—R$_{10}$', —OC(O)O—R$_{10}$', —C(O)N(R$_{10'}$)R$_{10'}$, —N(R$_{10'}$)C(O)N(R$_{10'}$)(R$_{10'}$), or —Si(OR$_{10'}$)$_w$(R$_{10'}$)$_t$, wherein each R$_{10}$' independently is hydrogen, linear or branched $C_1$-$C_{20}$ alkyl, phenyl($C_1$-$C_{20}$)alkyl, mono($C_1$-$C_{20}$)alkyl substituted phenyl($C_1$-$C_{20}$)alkyl, mono($C_1$-$C_{20}$)alkoxy substituted phenyl($C_1$-$C_{20}$)alkyl, ($C_1$-$C_{20}$)alkoxy($C_2$-$C_{20}$)alkyl, $C_3$-$C_{10}$ cycloalkyl, or mono($C_1$-$C_{20}$)alkyl substituted $C_3$-$C_{10}$ cycloalkyl, and w and t are each independently 0 to 3, provided that w+t is 3; and —N(R$_{11}$')R$_{12}$', wherein R$_{11}$' and R$_{12}$' are each independently hydrogen, linear or branched $C_1$-$C_{20}$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, linear or branched $C_1$-$C_{20}$ alkylaryl, $C_3$-$C_{10}$ cycloalkyl, $C_4$-$C_{20}$ bicycloalkyl, $C_5$-$C_{20}$ tricycloalkyl or linear or branched $C_1$-$C_{20}$ alkoxyalkyl, wherein the aryl group is phenyl or naphthyl, or R$_{11}$' and R$_{12}$' come together with the nitrogen atom to form a ring;

$R^4$ and $R^5$ are each independently selected from the group consisting of, (i) hydrogen, hydroxyl, linear or branched $C_1$-$C_{20}$ alkyl, linear or branched $C_1$-$C_{20}$ haloalkyl, $C_3$-$C_{10}$ cycloalkyl, allyl, benzyl, or substituted benzyl, the benzyl substituents being chosen from halogen, linear or branched $C_1$-$C_{20}$ alkyl or linear or branched $C_1$-$C_{20}$ alkoxy;

(ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl, the group substituents in each case being independently chosen from halogen, linear or branched $C_1$-$C_{20}$ alkyl or linear or branched $C_1$-$C_{20}$ alkoxy; and (iii) a group $Y^3$; or (iv) $R^4$ and $R^5$ together form a spiro substituent selected from the group consisting of a substituted or unsubstituted spiro-carbocyclic ring containing 3 to 10 carbon atoms, a substituted or unsubstituted spiro-heterocyclic ring containing 1 or 2 oxygen atoms and 3 to 10 carbon atoms including the spirocarbon atom, the spiro-carbocyclic ring and spiro-heterocyclic ring being annellated with 0, 1 or 2 benzene rings, the substituents being hydrogen or linear or branched $C_1$-$C_{20}$ alkyl; and B and B' are each independently selected from the group consisting of unsubstituted aryl, substituted aryl, unsubstituted heteroaryl, substituted heteroaryl, alkenyl, and alkynyl, or B and B' taken together form a ring structure, wherein each lengthening group $L^1$, $L^2$, and $L^3$ is independently represented by the following Formula (II),

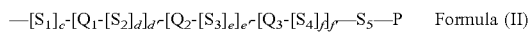
—[S₁]_c-[Q₁-[S₂]_d]_d'-[Q₂-[S₃]_e]_e'-[Q₃-[S₄]_f]_f'—S₅—P    Formula (II)

wherein:

(a) $Q_1$, $Q_2$, and $Q_3$ for each occurrence, are independently a divalent group selected from the group consisting of unsubstituted aryl, substituted aryl, unsubstituted heteroaryl, substituted heteroaryl, unsubstituted cycloalkyl, substituted cycloalkyl, unsubstituted heterocycloalky, and substituted heterocycloalkyl;

wherein the aryl substituents, heteroaryl substituents, cycloalkyl substituents, and heterocycloalkyl substituents are each independently selected from the group consisting of P, liquid crystal mesogens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$) alkoxy, perfluoro($C_1$-$C_{18}$)alkoxycarbonyl, perfluoro($C_1$-$C_{18}$)alkylcarbonyl, perfluoro($C_1$-$C_{18}$)alkylamino, di-(perfluoro($C_1$-$C_{18}$)alkyl)amino, perfluoro($C_1$-$C_{18}$)alkylthio, $C_1$-$C_{18}$ alkylthio, $C_1$-$C_{18}$ acetyl, $C_3$-$C_{10}$ cycloalkyl, $C_3$-$C_{10}$ cycloalkoxy, straight-chain $C_1$-$C_{18}$ alkyl, and branched $C_1$-$C_{18}$ alkyl;

wherein the straight-chain $C_1$-$C_{18}$ alkyl and branched $C_1$-$C_{18}$ alkyl are mono-substituted with a group selected from the group consisting of cyano, halogen, and $C_1$-$C_{18}$ alkoxy; or wherein the straight-chain $C_1$-$C_{18}$ alkyl and branched $C_1$-$C_{18}$ alkyl are poly-substituted with at least two groups independently selected from the group consisting of halogen, -M(T)$_{(v-1)}$ and -M(OT)$_{(v-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and v is the valence of M;

(b) c, d, e, and f are each independently chosen from an integer of 1 to 20; and each $S_1$, $S_2$, $S_3$, $S_4$, and $S_5$ is independently chosen for each occurrence from a spacer unit selected from the group consisting of:

(i) alkylene, substituted alkylene, haloalkylene, substituted haloalkylene, —Si(CH₂)_g—, and —(Si[(CH₃)₂]O)_h—, wherein g for each occurrence is independently chosen from an integer from 1 to 20; h for each occurrence is independently chosen from an integer from 1 to 16; and the substitutes for the alkylene and haloalkylene are independently selected from the group consisting of $C_1$-$C_{18}$ alkyl, $C_3$-$C_{10}$ cycloalkyl and aryl;

(ii) —N(Z)—, —C(Z)=C(Z)—, —C(Z)=N—, —C(Z')₂—C(Z')₂—, —N(Z)—C(Z)₂—, and a single bond, wherein Z for each occurrence is independently selected from the group consisting of hydrogen, $C_1$-$C_{18}$ alkyl, $C_3$-$C_{10}$ cycloalkyl and aryl, and Z' for each occurrence is independently selected from the group consisting of $C_1$-$C_{18}$ alkyl, $C_3$-$C_{10}$ cycloalkyl and aryl; and (iii) —O—, —C(=O)—, —C≡C—, —N=N—, —S—, —S(=O)—, —(O=)S(=O)—, —(O=)S(=O)O—, —O(O=)S(=O)O— and straight-chain or branched $C_1$-$C_{24}$ alkylene residue, the $C_1$-$C_{24}$ alkylene residue being unsubstituted, mono-substituted by cyano or halogen, or poly-substituted by halogen, provided that when two spacer units comprising heteroatoms are linked together the spacer units are linked so that heteroatoms are not directly linked to each other, and the bond between $S_5$ and P is free of two heteroatoms linked to each other;

(c) P for each occurrence is independently selected from the group consisting of hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$)alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy ($C_1$-$C_{18}$)alkyl, polyethyleneoxy, polypropyleneoxy, ethylene, acryloyl, acryloyloxy($C_1$-$C_{18}$)alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, maleimide derivatives, fumaric acid derivatives, unsubstituted cinnamic acid derivatives, cinnamic acid derivatives that are substituted with at least one of methyl, methoxy, cyano and halogen, and substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{187}$ alkoxy, amino, $C_3$-$C_{10}$ cycloalkyl, $C_1$-$C_{18}$ alkyl($C_1$-$C_{18}$)alkoxy, fluoro($C_1$-$C_{18}$)alkyl, cyano, cyano($C_1$-$C_{18}$)alkyl, cyano($C_1$-$C_{18}$)alkoxy or mixtures thereof, or P is a structure having from 2 to 4 reactive groups, or P is an unsubstituted or substituted ring opening metathesis polymerization precursor, or P is a substituted or unsubstituted photochromic compound; and (d) d', e' and f' are each independently chosen from 0, 1, 2, 3, and 4, provided that the sum of d'+e'+f' is at least 1; and wherein each group $Y^1$, $Y^2$, and $Y^3$ independently comprises at least one residue of a ring-opened cyclic monomer, wherein each ring-opened cyclic monomer is independently selected from the group consisting of a ring-opened cyclic ester monomer and a ring-opened cyclic carbonate monomer.

Clause 2: The photochromic compound of clause 1 wherein, $R^2$ is selected from the group consisting of, hydrogen; fluoro; chloro; bromo; linear or branched $C_1$-$C_{10}$ alkyl; linear or branched $C_1$-$C_{10}$ perhaloalkyl; —OR$^a$; —SR$^a$, where each R$^a$ is independently selected from the group consisting of hydrogen, linear or branched $C_1$-$C_{10}$ alkyl, and linear or branched $C_1$-$C_{10}$ perhaloalkyl; —C(O)O$R^b$, where $R^b$ is hydrogen or linear or branched $C_1$-$C_6$ alkyl; substituted or unsubstituted phenyl, each phenyl substituent being independently selected from the group consisting of hydroxyl, halogen, carbonyl, linear or branched $C_1$-$C_{10}$ alkoxycarbonyl, cyano, linear or branched $C_1$-$C_{10}$ haloalkyl, linear or branched $C_1$-$C_{10}$ alkyl, linear or branched $C_1$-$C_{10}$ alkoxy, and linear or branched $C_1$-$C_{10}$ perhaloalkyl; and the group $Y^1$;

$R^6$ and $R^7$ are each independently selected from the group consisting of, hydrogen; fluoro; chloro; bromo; the lengthening group $L^1$; —O$R^c$; and —S$R^c$, where each $R^c$ is independently selected from the group consisting of hydrogen, the lengthening group $L^2$, linear or branched $C_1$-$C_{10}$ alkyl, —C(O)—$R^d$, and —S(O)(O)—$R^e$, where $R^d$ and $R^e$ are each independently selected from the group consisting of linear or branched $C_1$-$C_6$ alkyl, linear or branched $C_1$-$C_6$ perhaloalkyl, phenyl, linear or branched $C_1$-$C_6$ alkyl substituted phenyl, and linear or branched $C_1$-$C_6$ perhaloalkyl substituted phenyl; and $R^1$ independently for each n, and $R^3$ independently for each m are each independently selected from the group consisting of,
hydrogen;
cyano;
the lengthening group $L^3$;
halogen selected from the group consisting of fluoro, chloro, and bromo;
linear or branched $C_1$-$C_{10}$ alkyl;
linear or branched $C_1$-$C_{10}$ perhaloalkyl;
$C_3$-$C_7$ cycloalkyl;
—O—$R_{10}$';
—S—$R_{10}$';
the group $Y^2$; and
substituted or unsubstituted phenyl, the phenyl substituents being selected from the group consisting of at least one of hydroxyl, halogen, carbonyl, linear or branched $C_1$-$C_{10}$ alkoxycarbonyl, cyano, linear or branched $C_1$-$C_{10}$ haloalkyl, linear or branched $C_1$-$C_{10}$ alkyl, linear or branched $C_1$-$C_{10}$ alkoxy, linear or branched $C_1$-$C_{10}$ perhaloalkyl, and combinations thereof;
wherein each $R_{10}$', of —O—$R_{10}$' and —S—$R_{10}$', independently is hydrogen, linear or branched $C_1$-$C_{10}$ alkyl, phenyl($C_1$-$C_{10}$)alkyl, mono($C_1$-$C_{10}$)alkyl substituted phenyl($C_1$-$C_{10}$)alkyl, mono($C_1$-$C_{10}$)alkoxy substituted phenyl($C_1$-$C_{10}$)alkyl, ($C_1$-$C_{10}$)alkoxy($C_2$-$C_{10}$)alkyl, $C_3$-$C_7$ cycloalkyl, or mono($C_1$-$C_{10}$)alkyl substituted $C_3$-$C_7$ cycloalkyl;

$R^4$ and $R^5$ are each independently selected from the group consisting of, hydrogen; linear or branched $C_1$-$C_{10}$ alkyl; linear or branched $C_1$-$C_{10}$ haloalkyl; $C_3$-$C_7$ cycloalkyl; and the group $Y^3$; or $R^4$ and $R^5$ together form a Spiro substituent that is a substituted or unsubstituted spiro-carbocyclic ring containing 3 to 10 carbon atoms; and B and B' are in each case independently selected from the group consisting of:
an aryl group that is mono-substituted with a reactive substituent; a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolindinyl, or heteroaromatic substituent is a reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein each of the phenyl, aryl and heteroaromatic substituents are each independently:
hydroxyl, a group —C(=O)$R_{21}$, wherein $R_{21}$ is —O$R_{22}$, —N($R_{23}$)$R_{24}$, piperidino, or morpholino, wherein $R_{22}$ is allyl, linear or branched $C_1$-$C_{20}$ alkyl, phenyl, mono($C_1$-$C_{20}$)alkyl substituted phenyl, mono($C_1$-$C_{20}$)alkoxy substituted phenyl, phenyl($C_1$-$C_{20}$)alkyl, mono($C_1$-$C_{20}$)alkyl substituted phenyl ($C_1$-$C_{20}$)alkyl, mono($C_1$-$C_{20}$)alkoxy substituted phenyl($C_1$-$C_{20}$)alkyl, $C_1$-$C_{20}$ alkoxy($C_2$-$C_{20}$)alkyl or $C_1$-$C_{20}$ haloalkyl, $R_{23}$ and $R_{24}$ are each independently $C_1$-$C_{20}$ alkyl, $C_5$-$C_{10}$ cycloalkyl, phenyl or substituted phenyl, the phenyl substituents being $C_1$-$C_{20}$ alkyl or $C_1$-$C_{20}$ alkoxy, and the halo substituent is chloro or fluoro, aryl, mono($C_1$-$C_{20}$)alkoxyaryl, di($C_1$-$C_{20}$)alkoxyaryl, mono($C_1$-$C_{20}$)alkylaryl, di($C_1$-$C_{20}$)alkylaryl, haloaryl, $C_3$-$C_{10}$ cycloalkylaryl, $C_3$-$C_{10}$ cycloalkyl, $C_3$-$C_{10}$ cycloalkyloxy, $C_3$-$C_{10}$ cycloalkyloxy($C_1$-$C_{20}$)alkyl, $C_3$-$C_{10}$ cycloalkyloxy($C_1$-$C_{20}$)alkoxy, aryl($C_1$-$C_{20}$)alkyl, aryl($C_1$-$C_{20}$)alkoxy, aryloxy, aryloxy($C_1$-$C_{20}$)alkyl, aryloxy($C_1$-$C_{20}$)alkoxy, mono- or di($C_1$-$C_{20}$)alkylaryl($C_1$-$C_{20}$)alkyl, mono- or di-($C_1$-$C_{20}$)alkoxyaryl ($C_1$-$C_{20}$)alkyl, mono- or di-($C_1$-$C_{20}$)alkylaryl($C_1$-$C_{20}$)alkoxy, mono- or di-($C_1$-$C_{20}$)alkoxyaryl($C_1$-$C_{20}$)alkoxy, amino, mono- or di-($C_1$-$C_{20}$) alkylamino, diarylamino, piperazino, N—($C_1$-$C_{20}$) alkylpiperazino, N-arylpiperazino, aziridino, indolino, piperidino, morpholino, thiomorpholino, tetrahydroquinolino, tetrahydroisoquinolino, pyrrolidyl, $C_1$-$C_{20}$ alkyl, $C_1$-$C_{20}$ haloalkyl, $C_1$-$C_{20}$ alkoxy, mono($C_1$-$C_{20}$)alkoxy($C_1$-$C_{20}$)alkyl, acryloxy, methacryloxy, or halogen;
an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of the substituents being $C_1$-$C_{20}$ alkyl, $C_1$-$C_{20}$ alkoxy, phenyl, or halogen;
a group represented by one of:

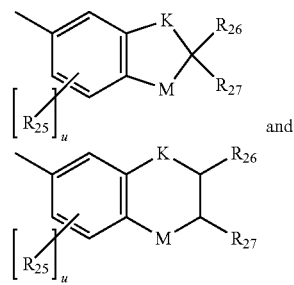

wherein K is —CH$_2$— or —O—, and M is —O— or substituted nitrogen, provided that when M is substituted nitrogen, K is —CH$_2$—, the substituted nitrogen substituents being hydrogen, $C_1$-$C_{20}$ alkyl, or $C_1$-$C_{20}$ acyl, each $R_{25}$ being independently chosen for each occurrence from $C_1$-$C_{20}$ alkyl, $C_1$-$C_{20}$ alkoxy, hydroxy, and halogen, $R_{26}$ and $R_{27}$ each being independently hydrogen or $C_1$-$C_{20}$ alkyl, and u is an integer ranging from 0 to 2; or a group represented by:

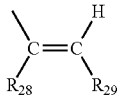

wherein $R_{28}$ is hydrogen or $C_1$-$C_{20}$ alkyl, and $R_{29}$ is an unsubstituted, mono-, or di-substituted group chosen from naphthyl, phenyl, furanyl, and thienyl, wherein the substituents are $C_1$-$C_{20}$ alkyl, $C_1$-$C_{20}$ alkoxy, or halogen; or B and B' taken together form one of a fluoren-9-ylidene, mono-, or di-substituted fluoren-9-ylidene, each of the fluoren-9-ylidene substituents being independently chosen from $C_1$-$C_{20}$ alkyl, $C_1$-$C_{20}$ alkoxy, and halogen;

wherein independently for each group $Y^1$, $Y^2$, and $Y^3$, each cyclic ester monomer, of each ring-opened cyclic ester monomer, is independently represented by the following Formula (A),

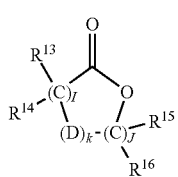

(A)

wherein for Formula (A), I and J are each independently integers ranging from 1 to 8; $R^{13}$, $R^{14}$, $R^{15}$, and $R^{16}$ are independently chosen for each carbon unit $(C)_I$ and $(C)_J$ from —H and C1-C16 alkyl; k is 0 or 1; and D is —O— when k is 1; and each cyclic carbonate monomer, of each ring-opened cyclic carbonate monomer, is independently represented by the following Formula (B),

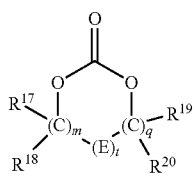

(B)

wherein for Formula (B), m and q are each independently integers ranging from 1 to 3; $R^{17}$, $R^{18}$, $R^{19}$, and $R^{20}$ are each independently chosen for each carbon unit $(C)_m$ and $(C)_q$ from —H and C1-C16 alkyl; t is 0 or 1; and E is —O— when t is 1.

Clause 3: The photochromic compound of clause 2 wherein, $R^2$ is selected from the group consisting of, hydrogen; fluoro; chloro; bromo; linear or branched $C_1$-$C_6$ alkyl; linear or branched $C_1$-$C_6$ perhaloalkyl; —$OR^a$; —$SR^a$, where each $R^a$ is independently selected from the group consisting of hydrogen, linear or branched $C_1$-$C_6$ alkyl, and linear or branched $C_1$-$C_6$ perhaloalkyl; —C(O)$OR^b$, where $R^b$ is hydrogen or linear or branched $C_1$-$C_3$ alkyl; substituted or unsubstituted phenyl, each phenyl substituent being independently selected from the group consisting of hydroxyl, halogen, linear or branched $C_1$-$C_6$ alkoxycarbonyl, cyano, linear or branched $C_1$-$C_6$ haloalkyl, linear or branched $C_1$-$C_6$ alkyl, linear or branched $C_1$-$C_6$ alkoxy, and linear or branched $C_1$-$C_6$ perhaloalkyl; and the group $Y^1$;

$R^6$ and $R^7$ are each independently selected from the group consisting of, hydrogen; fluoro; chloro; bromo; the lengthening group $L^1$; —$OR^c$; and —$SR^c$, where each $R^c$ is independently selected from the group consisting of hydrogen, the lengthening group $L^2$, linear or branched $C_1$-$C_6$ alkyl, —C(O)—$R^d$, and —S(O)(O)—$R^e$, where $R^d$ and $R^e$ are each independently selected from the group consisting of linear or branched $C_1$-$C_3$ alkyl, linear or branched $C_1$-$C_3$ perhaloalkyl, phenyl, linear or branched $C_1$-$C_3$ alkyl substituted phenyl, and linear or branched $C_1$-$C_3$ perhaloalkyl substituted phenyl, $R^1$ independently for each n, and $R^3$ independently for each m are each independently selected from the group consisting of, hydrogen;

cyano;

the lengthening group $L^3$;

linear or branched $C_1$-$C_6$ alkyl;

$C_3$-$C_6$ cycloalkyl;

linear or branched $C_1$-$C_8$ perhaloalkyl;

fluoro;

chloro;

bromo,

—O—$R_{10}$',

—S—$R_{10}$';

the group $Y^2$; and substituted or unsubstituted phenyl, the phenyl substituents being selected from the group consisting of at least one of hydroxyl, halogen, linear or branched $C_1$-$C_6$ alkoxycarbonyl, cyano, linear or branched $C_1$-$C_6$ haloalkyl, linear or branched $C_1$-$C_6$ alkyl, linear or branched $C_1$-$C_6$ alkoxy, and linear or branched $C_1$-$C_6$ perhaloalkyl;

wherein each $R_{10}$', of —O—$R_{10}$' and —S—$R_{10}$', independently is hydrogen, linear or branched $C_1$-$C_6$ alkyl, phenyl($C_1$-$C_6$)alkyl, mono($C_1$-$C_6$)alkyl substituted phenyl($C_1$-$C_6$)alkyl, mono($C_1$-$C_6$) alkoxy substituted phenyl($C_1$-$C_6$)alkyl, ($C_1$-$C_6$) alkoxy($C_2$-$C_6$)alkyl, $C_3$-$C_6$ cycloalkyl, or mono ($C_1$-$C_6$)alkyl substituted $C_3$-$C_6$ cycloalkyl;

$R^4$ and $R^5$ are each independently selected from the group consisting of, hydrogen; linear or branched $C_1$-$C_8$ alkyl; linear or branched $C_1$-$C_8$ haloalkyl; $C_3$-$C_6$ cycloalkyl; and the group $Y^3$; or $R^4$ and $R^5$ together form a spiro substituent that is a substituted or unsubstituted spiro-carbocyclic ring containing 3 to 10 carbon atoms; and B and B' are in each case independently selected from the group consisting of,
unsubstituted aryl,
aryl substituted with linear or branched $C_1$-$C_6$ alkoxy,
aryl substituted with linear or branched $C_1$-$C_6$ perhaloalkyl,
aryl substituted with morpholino, and
aryl substituted with piperidino
wherein independently for each group $Y^1$, $Y^2$, and $Y^3$,
each cyclic ester monomer, of each ring-opened cyclic ester monomer, is independently selected from the group consisting of, ε(epsilon)-caprolactone; ζ(zeta)-enantholactone; δ(delta)-valerolactone; a monoalkyl δ(delta)-valerolactone; a monoalkyl-, dialkyl-, or trialkyl-ε(epsilon)-caprolactone; β(beta)-lactones; γ(gamma)-lactones; dilactones; and ketodioxanones; and
each cyclic carbonate monomer, of each ring-opened cyclic carbonate monomer, is independently selected from the group consisting of, ethylene carbonate; 3-ethyl-3-hydroxylmethyl trimethylene carbonate; propylene caronate, trimethylene carbonate; trimethylolpropane monocarbonate; 4,6-dimethyl-1,3-propylene carbonate; 2,2-dimethyl trimethylene carbonate; and 1,2-dioxepan-2-one.

Clause 4: The photochromic compound of clauses 1, 2, or 3 wherein, at least one of $R^6$ and $R^7$ is selected from the group consisting of the lengthening group $L^1$ and —$OR^c$ where $R^c$ is the lengthening group $L^2$.

Clause 5: The photochromic compound of clauses 1, 2, or 3 wherein,
independently for each lengthening group $L^1$, $L^2$, and $L^3$ represented by Formula (II),
(a) $Q_1$, $Q_2$, and $Q_3$ for each occurrence, are independently selected from the group consisting of unsubstituted aryl, substituted aryl, unsubstituted cycloalkyl, and substituted cycloalkyl,
(b) each $S_1$, $S_2$, $S_3$, $S_4$, and $S_5$ is independently chosen for each occurrence from a spacer unit selected from the group consisting of,
(ii) —N(Z)—, —C(Z)=C(Z)—, —C(Z)=N—, —C(Z')$_2$—C(Z')$_2$—, —N(Z)—C(Z')$_2$—, and a single bond, wherein Z for each occurrence is independently selected from the group consisting of hydrogen, $C_1$-$C_8$ alkyl, $C_3$-$C_6$ cycloalkyl and aryl, and Z' for each occurrence is independently selected from the group consisting of $C_1$-$C_8$ alkyl, $C_3$-$C_6$ cycloalkyl and aryl, and
(iii) —O—, —C(=O)—, —C≡C—, —N=N—, —S—, —S(=O)—, and straight-chain or branched $C_1$-$C_{12}$ alkylene residue, the $C_1$-$C_{12}$ alkylene residue being unsubstituted, mono-substituted by cyano or halogen, or poly-substituted by halogen, and
(c) P for each occurrence is independently selected from the group consisting of hydrogen, hydroxy, amino, $C_2$-$C_8$ alkenyl, $C_2$-$C_8$ alkynyl, acryloyloxy, methacryloyloxy, 2-(acryloyloxy)ethylcarbamyl, 2-(methacryloyloxy)ethylcarbamyl, epoxy, carboxylic acid, carboxylic ester, acryloylamino, methacryloylamino, aminocarbonyl, $C_1$-$C_8$ alkyl aminocarbonyl, aminocarbonyl($C_1$-$C_8$)alkyl, $C_1$-$C_8$ alkyloxycarbonyloxy, halocarbonyl, aryl, hydroxy($C_1$-$C_8$)alkyl, $C_1$-$C_8$ alkyl, $C_1$-$C_8$ alkoxy, amino($C_1$-$C_8$)alkyl, $C_1$-$C_8$ alkylamino, di-($C_1$-$C_8$)alkylamino, $C_1$-$C_8$ alkyl($C_1$-$C_8$)alkoxy, $C_1$-$C_8$ alkoxy($C_1$-$C_8$)alkoxy, nitro, poly($C_1$-$C_8$)alkyl ether, ($C_1$-$C_8$)alkyl($C_1$-$C_8$)alkoxy($C_1$-$C_8$)alkyl, polyethyleneoxy, polypropyleneoxy, ethylene, acryloyl, acryloyloxy($C_1$-$C_{18}$)alkyl, methacryloyl, methacryloyloxy($C_1$-$C_8$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, and vinyl ester.

Clause 6: The photochromic compound of clause 5 wherein,
independently for each lengthening group $L^1$, $L^2$, and $L^3$ represented by Formula (II),
(b) each $S_1$, $S_2$, $S_3$, $S_4$, and $S_5$ is independently chosen for each occurrence from a spacer unit selected from the group consisting of,
(ii) —N(Z)—, —C(Z)=C(Z)—, and a single bond, wherein Z for each occurrence is independently selected from the group consisting of hydrogen, $C_1$-$C_8$ alkyl, $C_3$-$C_6$ cycloalkyl and aryl, and Z' for each occurrence is independently selected from the group consisting of $C_1$-$C_8$ alkyl, $C_3$-$C_6$ cycloalkyl and aryl, and
(iii) —O—, —C(=O)—, —C≡C—, and straight-chain or branched $C_1$-$C_6$ alkylene residue, the $C_1$-$C_6$ alkylene residue being unsubstituted, mono-substituted by cyano or halogen, or poly-substituted by halogen, and
(c) P for each occurrence is independently selected from the group consisting of hydrogen, hydroxy, amino, $C_2$-$C_8$ alkenyl, $C_2$-$C_8$ alkynyl, and aryl.

Clause 7: The photochromic compound of clause 4 wherein, $R^6$ and $R^7$ are each independently selected from the group consisting of the lengthening group $L^1$ and —$OR^c$ where $R^c$ is the lengthening group $L^2$.

Clause 8: The photochromic compound of clauses 1, 2, or 3 wherein, $R^6$ is selected from the group consisting of the lengthening group $L^1$ and —$OR^c$ where $R^c$ is the lengthening group $L^2$, and $R^7$ is halogen.

Clause 9: The photochromic compound of clause 4 wherein, $R^3$ at position-11 is selected from the group consisting of, halogen, —CN, linear or branched $C_1$-$C_8$ perhaloalkyl, unsubstituted phenyl, and phenyl substituted with at least one of halogen and linear or branched $C_1$-$C_8$ perhaloalkyl.

Clause 10: The photochromic compound of clauses 1, 2, or 3 wherein, $R^3$ at position-12 is the lengthening group $L^3$.

Clause 11: The photochromic compound of clause 4 wherein, $R^3$ at position-11 is halogen.

Clause 12: The photochromic compound of clause 1, wherein the photochromic compound is selected from at least one of the following photochromic compounds PC-(I-1) through PC-(I-15) (where, in the present clause, chemical structures corresponding to the named photochromic compounds are provided in the Examples previously herein, as noted for each named photochromic compound):

PC-(I-1) (see Example 1) 6-(4-methoxyphenyl)-6-(4-butoxyphenyl)-9,9-dimethyl-1-hydroxy-15-bromo-11-trifluoromethyl-6H,9H-indeno[2',3':2,1]phenanthro[4,3-b]pyran;

PC-(I-2) (see Example 2) 6-phenyl-6-(4-butoxyphenyl)-9,9-dimethyl-1-hydroxy-15-bromo-11-trifluoromethyl-6H,9H-indeno[2',3':2,1]phenanthro[4,3-b]pyran;

PC-(I-3) (see Example 3) 6-phenyl-6-(4-morpholinophenyl)-9,9-dimethyl-1-hydroxy-15-bromo-11-trifluoromethyl-6H,9H-indeno[2',3':2,1]phenanthro[4,3-b]pyran;

PC-(I-4) (see Example 4) 6-phenyl-6-(4-butoxyphenyl)-9,9-dimethyl-1-butoxy-11-trifluoromethyl-6H,9H-indeno[2',3':2,1]phenanthro[4,3-b]pyran;

PC-(I-5) (see Example 5) 6-phenyl-6-(4-morpholinophenyl)-9,9-dimethyl-1-butoxy-11-trifluoromethyl-6H,9H-indeno[2',3':2,1]phenanthro[4,3-b]pyran;

PC-(I-6) (see Example 6) 6-(4-methoxyphenyl)-6-(4-butoxyphenyl)-9,9-dimethyl-1-((6-((4'-(trans-4-pentylcyclohexyl)-[1,1'-biphenyl]-4-yl)oxy)hexyl)oxy)-15-bromo-11-trifluoromethyl-6H,9H-indeno[2',3':2,1]phenanthro[4,3-b]pyran;

PC-(I-7) (see Example 7) 6-(4-methoxyphenyl)-6-(4-butoxyphenyl)-9,9-dimethyl-1-(5-((4'-(trans-4-pentylcyclohexyl-[1,1'-biphenyl]-4-yl)oxy)pentylcarbonyloxy)-15-bromo-11-trifluoromethyl-6H,9H-indeno[2',3':2,1]phenanthro[4,3-b]pyran;

PC-(I-8) (see Example 8) 6-(4-methoxyphenyl)-6-(4-butoxyphenyl)-9,9-dimethyl-1-((4'-(trans-4-pentylcyclohexyl)-[1,1'-biphenyl]-4-yl)carbonyloxy)-15-bromo-11-trifluoromethyl-6H,9H-indeno[2',3':2,1]phenanthro[4,3-b]pyran;

PC-(I-9) (see Example 9) 6-(4-methoxyphenyl)-6-(4-butoxyphenyl)-9,9-dimethyl-1-((4'-(trans-4-pentylcyclohexyl)-[1,1'-biphenyl]-4-yl)carbonyloxy)-11-trifluoromethyl-6H,9H-indeno[2',3':2,1]phenanthro[4,3-b]pyran;

PC-(I-10) (see Example 10) 6-(4-methoxyphenyl)-6-(4-butoxyphenyl)-9,9-dimethyl-1-((6-((4'-(trans-4-pentylcyclohexyl)-[1,1'-biphenyl]-4-yl)oxy)hexyl)oxy)-15-(2-methyl-(4-(4'-(trans-4-pentylcyclohexyl)-[1,1'-biphenyl]-4-yl)carboxamido)phenyl)-11-trifluoromethyl-6H,9H-indeno[2',3':2,1]phenanthro[4,3-b]pyran;

PC-(I-11) (see Example 11) 6-(4-methoxyphenyl)-6-(4-butoxyphenyl)-9,9-dimethyl-1-(5-((4'-(trans-4-pentylcyclohexyl)-[1,1'-biphenyl]-4-yl)oxy)pentylcarbonyloxy)-15-(2-methyl-(4-(4'-(trans-4-pentylcyclohexyl)-[1,1'-biphenyl]-4-yl)carboxamido)phenyl)-11-trifluoromethyl-6H,9H-indeno[2',3':2,1]phenanthro[4,3-b]pyran;

PC-(I-12) (see Example 12) 6-(4-methoxyphenyl)-6-(4-butoxyphenyl)-9,9-dimethyl-1-((4'-(trans-4-pentylcyclohexyl)-[1,1'-biphenyl]-4-yl)carbonyloxy)-15-(2-methyl-(4-(4'-(trans-4-pentylcyclohexyl)-[1,1'-biphenyl]-4-yl)carboxamido)phenyl)-11-trifluoromethyl-6H,9H-indeno[2',3':2,1]phenanthro[4,3-b]pyran;

PC-(I-13) (see Example 13) 6-(4-methoxyphenyl)-6-(4-butoxyphenyl)-9,9-dimethyl-1-((6-((4'-(trans-4-pentylcyclohexyl)-[1,1'-biphenyl]-4-yl)oxy)hexyl)oxy)-15-((4-(4'-(trans-4-pentylcyclohexyl)-[1,1'-biphenyl]-4-yl)carboxamido)phenyl)-11-trifluoromethyl-6H,9H-indeno[2',3':2,1]phenanthro[4,3-b]pyran;

PC-(I-14) (see Example 14) 6-(4-methoxyphenyl)-6-(4-butoxyphenyl)-9,9-dimethyl-1-((4'-(trans-4-pentylcyclohexyl)-[1,1'-biphenyl]-4-yl)carbonyloxy)-15-((4-(4'-(trans-4-pentylcyclohexyl)-[1,1'-biphenyl]-4-yl)carboxamido)phenyl)-11-trifluoromethyl-6H,9H-indeno[2',3':2,1]phenanthro[4,3-b]pyran; and PC-(I-15) (see Example 15) 6-(4-methoxyphenyl)-6-(4-butoxyphenyl)-9,9-dimethyl-1-pentylcarbonyloxy-15-(2-methyl-(4-(4'-(trans-4-pentylcyclohexyl)-[1,1'-biphenyl]-4-yl)carboxamido)phenyl)-11-trifluoromethyl-6H,9H-indeno[2',3':2,1]phenanthro[4,3-b]pyran.

Clause 13: A photochromic compound represented by the following Formula (III), $$L^y\text{-}(PC)_{n'} \quad \text{Formula (III)}$$

wherein, n' is at least 2,

PC independently for each n' is a residue of the photochromic compound of clauses 1, 2, 3, or 12, and $L^y$ is a multivalent linking group selected from the group consisting of, a first multivalent compound that is a multivalent polymer, and a second multivalent compound that is different than the first multivalent compound, the second multivalent compound being non-polymeric and comprising a residue selected from the group consisting of, a residue of a polyisocyanate, a residue of a polyol, a residue of a polycarboxylic acid, a residue of a polycarbonate functional material, and combinations thereof.

Clause 14 The photochromic compound of clause 13 wherein, the multivalent polymer, of the first multivalent compound, is selected from the group consisting of multivalent polyurethane, multivalent polyester, multivalent polyether, multivalent poly(meth)acrylate, multivalent polyvinylalcohol, multivalent polycarbonate, multivalent polysiloxane, and multivalent cyclic polysiloxane, and for the second multivalent compound, the polyisocyanate is selected from the group consisting of aliphatic polyisocyanates, cycloaliphatic polyisocyanates, heterocyclic polyisocyanates, and aromatic polyisocyanates, each independently having at least two isocyanate groups, dimers thereof, trimers thereof, and mixtures of one or more thereof, the polyol is selected from the group consisting of aliphatic polyols, cycloaliphatic polyols, heterocyclic polyols, and aromatic polyols, each independently having at least two hydroxyl groups, the polycarboxylic acid is selected from the group consisting of aliphatic polycarboxylic acids, cycloaliphatic polycarboxylic acids, heterocyclic polycarboxylic acids, and aromatic polycarboxylic acids, each independently having at least two carboxylic acid groups, and the polycarbonate functional material is selected from the group consisting of aliphatic polycarbonate functional compounds, cycloaliphatic polycarbonate functional compounds, heterocyclic polycarbonate functional compounds, and aromatic polycarbonate functional compounds, each independently having at least two cyclic carbonate groups.

Clause 15: A photochromic composition comprising the photochromic compound of clauses 1, 2, 3, or 12.

Clause 16: A photochromic article comprising the photochromic compound of clauses 1, 2, 3, or 12.

Clause 17: The photochromic article of clause 16 wherein the photochromic article is selected from the group consisting of ophthalmic articles, display articles, windows, mirrors, active liquid crystal cell articles, and passive liquid crystal cell articles.

Clause 18: The photochromic article of clause 17, wherein the photochromic article is selected from ophthalmic articles, and the ophthalmic articles are selected from the group consisting of corrective lenses, non-corrective lenses, contact lenses, intra-ocular lenses, magnifying lenses, protective lenses, and visors.

Clause 19: The photochromic article of clause 17, wherein the photochromic article is selected from display articles, and the display articles are selected from the group consisting of screens, monitors, and security elements.

The present invention has been described with reference to specific details of particular embodiments thereof. It is not intended that such details be regarded as limitations upon the scope of the invention except insofar as to the extent that they are included in the accompanying claims.

What is claimed is:

1. A photochromic compound represented by the following Formula (I),

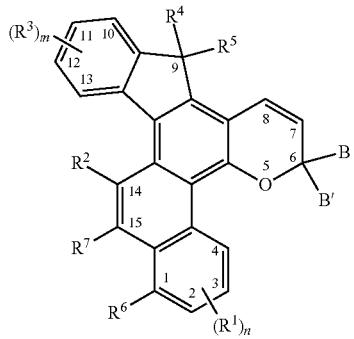

(I)

wherein n is 1 to 3, and m is 1 to 4, $R^2$ is selected from the group consisting of, hydrogen; halogen; linear or branched $C_1$-$C_{20}$ alkyl; linear or branched $C_1$-$C_{20}$ perhaloalkyl; —$OR^a$; —$SR^a$, where each $R^a$ is independently selected from the group consisting of hydrogen, linear or branched $C_1$-$C_{20}$ alkyl, and linear or branched $C_1$-$C_{20}$ perhaloalkyl; —C(O)$OR^b$, where $R^b$ is hydrogen or linear or branched $C_1$-$C_{10}$ alkyl; substituted or unsubstituted aryl, each aryl substituent being independently selected from the group consisting of hydroxyl, halogen, carbonyl, linear or branched $C_1$-$C_{20}$ alkoxycarbonyl, cyano, linear or branched $C_1$-$C_{20}$ haloalkyl, linear or branched $C_1$-$C_{20}$ alkyl, linear or branched $C_1$-$C_{20}$ alkoxy, and linear or branched $C_1$-$C_{20}$ perhaloalkyl; and a group $Y^1$;

$R^6$ and $R^7$ are each independently selected from the group consisting of, hydrogen; halogen; a lengthening group $L^1$; —$OR^c$, and —$SR^c$, where each $R^c$ is independently selected from the group consisting of hydrogen, a lengthening group $L^2$, linear or branched $C_1$-$C_{20}$ alkyl, —C(O)—$R^d$, and —S(O)(O)—$R^e$, where $R^d$ and $R^e$ are each independently selected from the group consisting of linear or branched $C_1$-$C_{10}$ alkyl, phenyl, linear or branched $C_1$-$C_{10}$ perhaloalkyl, phenyl, linear or branched $C_1$-$C_{10}$ alkyl substituted phenyl, and linear or branched $C_1$-$C_{10}$ perhaloalkyl substituted phenyl,
provided that at least one of $R^6$ and $R^7$ is other than hydrogen;

$R^1$ independently for each n, and $R^3$ independently for each m are each independently selected from the group consisting of,
hydrogen;
cyano;
a reactive substituent;
a lengthening group $L^3$;
halogen selected from the group consisting of fluoro, chloro, and bromo;
linear or branched $C_1$-$C_{20}$ alkyl;
linear or branched $C_1$-$C_{20}$ perhaloalkyl;
$C_3$-$C_{10}$ cycloalkyl;
a group $Y^2$;
substituted or unsubstituted phenyl, the phenyl substituents being selected from the group consisting of at least one of hydroxyl, halogen, carbonyl, linear or branched $C_1$-$C_{20}$ alkoxycarbonyl, cyano, linear or branched $C_1$-$C_{20}$ haloalkyl, linear or branched $C_1$-$C_{20}$ alkyl, linear or branched $C_1$-$C_{20}$ alkoxy, linear or branched $C_1$-$C_{20}$ perhaloalkyl, and combinations thereof;
—O—$R_{10}'$, —S—$R_{10}'$, —C(O)—$R_{10}'$, —C(O)—$OR_{10}'$, —OC(O)—$R_{10}'$, —OC(O)O—$R_{10}'$, —C(O)N($R_{10}'$)$R_{10}'$, —N($R_{10}'$)C(O)N($R_{10}'$)($R_{10}'$), or —Si(O$R_{10}'$)$_w$($R_{10}'$)$_t$, wherein each $R_{10}'$ independently is hydrogen, linear or branched $C_1$-$C_{20}$ alkyl, phenyl($C_1$-$C_{20}$)alkyl, mono($C_1$-$C_{20}$)alkyl substituted phenyl($C_1$-$C_{20}$)alkyl, mono($C_1$-$C_{20}$)alkoxy substituted phenyl($C_1$-$C_{20}$)alkyl, ($C_1$-$C_{20}$)alkoxy($C_2$-$C_{20}$)alkyl, $C_3$-$C_{10}$ cycloalkyl, or mono($C_1$-$C_{20}$)alkyl substituted $C_3$-$C_{10}$ cycloalkyl, and w and t are each independently 0 to 3, provided that w+t is 3; and
—N($R_{11}'$)$R_{12}'$, wherein $R_{11}'$ and $R_{12}'$ are each independently hydrogen, linear or branched $C_1$-$C_{20}$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, linear or branched $C_1$-$C_{20}$ alkylaryl, $C_3$-$C_{10}$ cycloalkyl, $C_4$-$C_{20}$ bicycloalkyl, $C_5$-$C_{20}$ tricycloalkyl or linear or branched $C_1$-$C_{20}$ alkoxyalkyl, wherein the aryl group is phenyl or naphthyl, or $R_{11}'$ and $R_{12}'$ come together with the nitrogen atom to form a ring;

$R^4$ and $R^5$ are each independently selected from the group consisting of,
(i) hydrogen, hydroxyl, linear or branched $C_1$-$C_{20}$ alkyl, linear or branched $C_1$-$C_{20}$ haloalkyl, $C_3$-$C_{10}$ cycloalkyl, allyl, benzyl, or substituted benzyl, the benzyl substituents being selected from the group consisting of halogen, linear or branched $C_1$-$C_{20}$ alkyl or linear or branched $C_1$-$C_{20}$ alkoxy;
(ii) an unsubstituted, mono- di- or tri-substituted group selected from the group consisting of phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl, the group substituents in each case being independently selected from the group consisting of halogen, linear or branched $C_1$-$C_{20}$ alkyl or linear or branched $C_1$-$C_{20}$ alkoxy; and
(iii) a group $Y^3$; or
(iv) $R^4$ and $R^5$ together form a spiro substituent selected from the group consisting of a substituted or unsubstituted spiro-carbocyclic ring containing 3 to 10 carbon atoms, a substituted or unsubstituted spiro-heterocyclic ring containing 1 or 2 oxygen atoms and 3 to 10 carbon atoms including the spirocarbon atom, the spiro-carbocyclic ring and spiro-heterocyclic ring being annellated with 0, 1 or 2 benzene rings, the substituents being hydrogen or linear or branched $C_1$-$C_{20}$ alkyl; and B and B' are each independently selected from the group consisting of unsubstituted aryl, substituted aryl, unsubstituted heteroaryl, substituted heteroaryl, alkenyl, and alkynyl, or B and B' taken together form a ring structure, wherein each group $Y^1$, $Y^2$, and $Y^3$ independently comprises at least one residue of a ring-opened cyclic monomer, wherein each ring-opened cyclic monomer is independently selected from the group consisting of a ring-opened cyclic ester monomer and a ring-opened cyclic carbonate monomer, and wherein each the lengthening group L¹, L², and L³ is independently selected from the group consisting of, L(5) 4-(4-pentyl-phenylazo)-phenylcarbamoyl

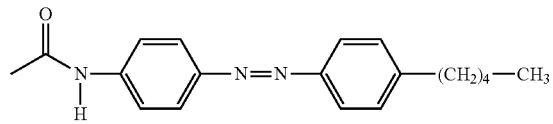

L(7) {4-[5-(4-propyl-benzoyloxy)-pyrimidin-2-yl]-phenyl} ester

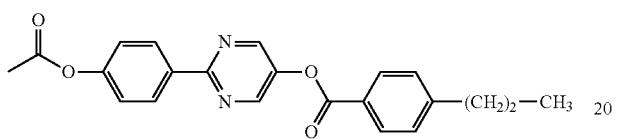

L(8) {4-[2-(4'-methyl-biphenyl-4-carbonyloxy)-1,2-diphenyl-ethoxycarbonyl]-phenyl} ester

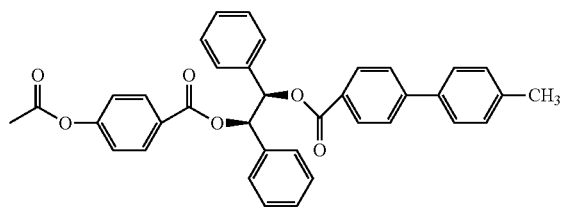 [SMILES: CC(=O)Oc1ccc(C(=O)O[C@H](c2ccccc2)[C@H](OC(=O)c2ccc(-c3ccc(C)cc3)cc2)c2ccccc2)cc1]

L(10) 4-[4-(4-{4-[3-(6-{4-[4-(4-nonyl-benzoyloxy)-phenoxycarbonyl]-phenoxy}-hexyloxycarbonyl)-propionyloxy]-benzoyloxy}-benzoyloxy)-phenyl]-piperazin-1-yl

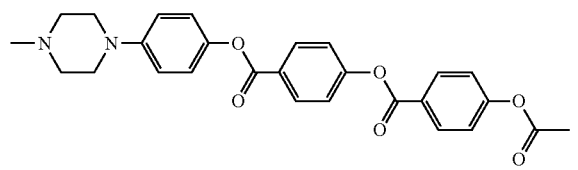

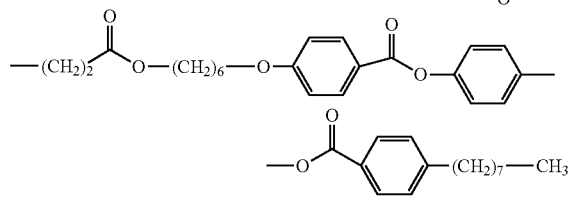

L(11) {4-[4-(4-{4-[4-(4-nonyl-benzoyloxy)-benzoyloxy]-benzoyloxy}-benzoyloxy)-phenyl]-piperazin-1-yl}

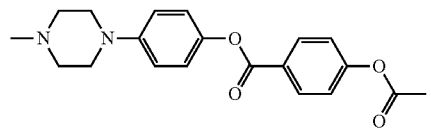

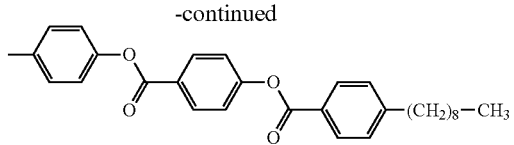

L(12) 4-(4'-propyl-biphenyl-4-ylethynyl)-phenyl

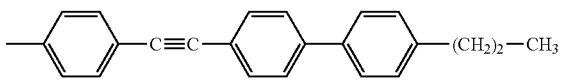

L(16) 4-(biphenyl-4-carbonyloxy)-piperidin-1-yl

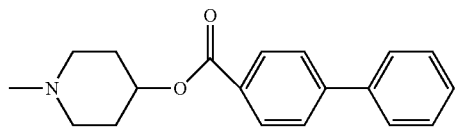 [SMILES: CN1CCC(OC(=O)c2ccc(-c3ccccc3)cc2)CC1]

L(18) 4-(4-phenylcarbamoyl-phenylcarbamoyl)-piperidin-1-yl

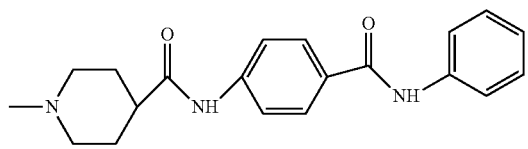 [SMILES: CN1CCC(C(=O)Nc2ccc(C(=O)Nc3ccccc3)cc2)CC1]

L(19) 4-(4-(4-phenylpiperidin-1-yl)-benzoyloxy)-piperidin-1-yl

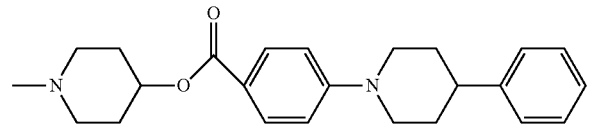 [SMILES: CN1CCC(OC(=O)c2ccc(N3CCC(c4ccccc4)CC3)cc2)CC1]

L(20) 4-butyl-[1,1';4',1"]terphenyl-4-yl

L(21) 4-(4-pentadecafluoroheptyloxy-phenylcarbamoyl)-benzyloxy

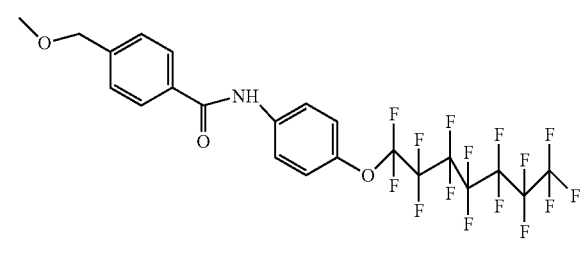 [SMILES: COCc1ccc(C(=O)Nc2ccc(OC(F)(F)C(F)(F)C(F)(F)C(F)(F)C(F)(F)C(F)(F)C(F)(F)F)cc2)cc1]

L(24) 4-[4-(4-cyclohexyl-phenylcarbamoyl)-benzoyloxy]-piperidin-1-yl

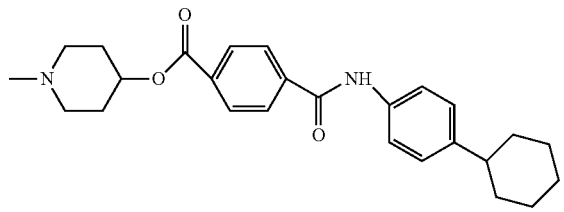 [SMILES: CN1CCC(OC(=O)c2ccc(C(=O)Nc3ccc(C4CCCCC4)cc3)cc2)CC1]

L(25) N-{4-[(4-pentyl-benzylidene)-amino]-phenyl}-acetamidyl

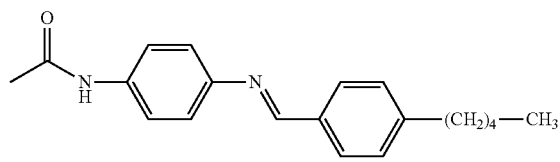

L(28) 4-(4'-hexyloxy-biphenyl-4-carbonyloxy)-piperidin-1-yl

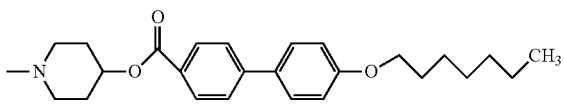 [SMILES: CCCCCCCOc1ccc(-c2ccc(C(=O)OC3CCN(C)CC3)cc2)cc1]

L(30a) 1-methyl-4-((4'-(((1-methylpiperidin-4-yl)oxy)carbonyl)-[1,1'-biphenyl]-4-carbonyl)oxy)piperidin-1-yl

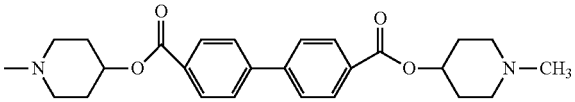

L(30b) bis(1-yl-piperidin-4-yl) [1,1'-biphenyl]-4,4'-dicarboxylate

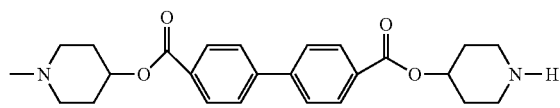 [SMILES: CN1CCC(OC(=O)c2ccc(-c3ccc(C(=O)OC4CCNCC4)cc3)cc2)CC1]

L(31)-(4-(9-(4-butylphenyl)-2,4,8,10-tetraoxaspiro[5.5]undec-3-yl)phenyl)piperazin-1-yl

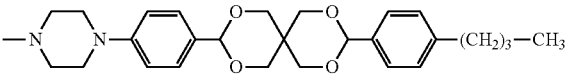

L(32) 4-(6-(4-butylphenyl)carbonyloxy-(4,8-dioxabicyclo[3.3.0]oct-2-yl))oxycarbonyl)phenyl

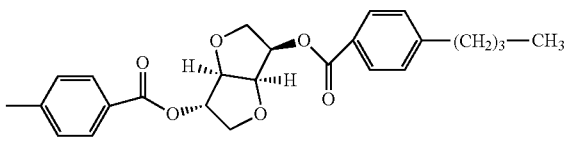

L(33) 1-{4-[5-(4-butyl-phenyl)-[1,3]dioxan-2-yl]-phenyl}-4-methyl-piperazin-1-yl

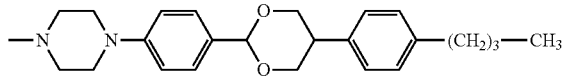

L(34) 4-(7-(4-propylphenylcarbonyloxy)bicyclo[3.3.0]oct-2-yl)oxycarbonyl)phenyl

L(35) 4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy

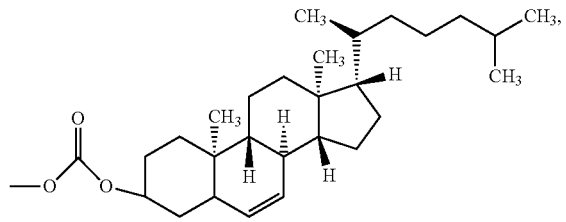

L(a)

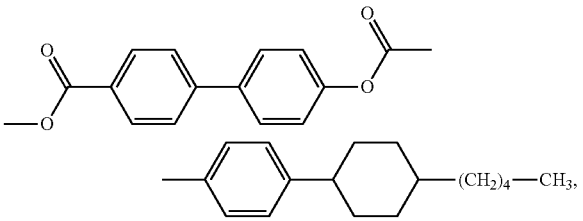

L(c)

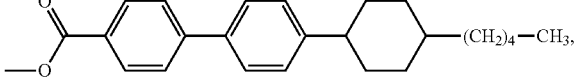

L(g)
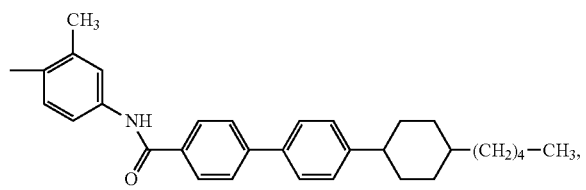
L(h)
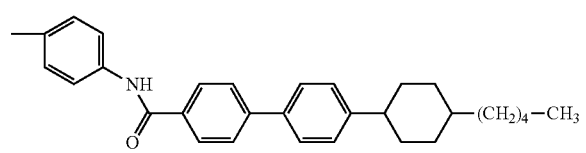
L(i)
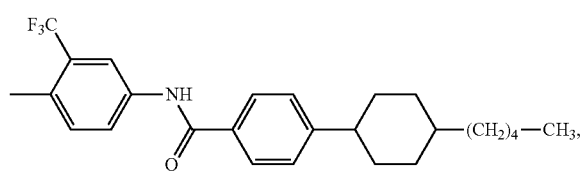
L(j)
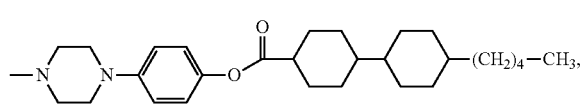
L(k)
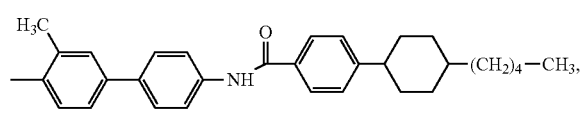
L(l)
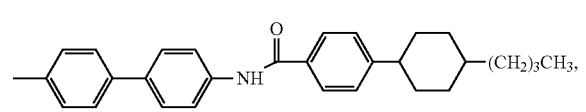
L(m)
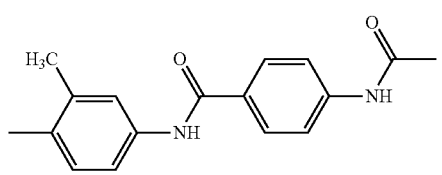
-continued
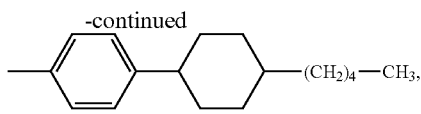
L(r)
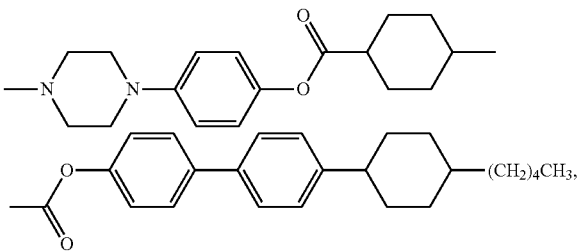
L(t)
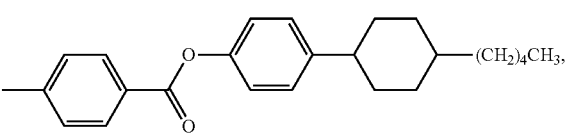
L(v)
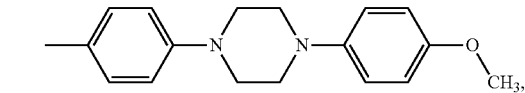
L(z)
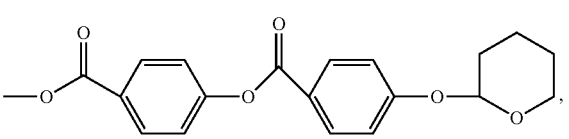 [SMILES: COC(=O)c1ccc(OC(=O)c2ccc(OC3CCCCO3)cc2)cc1]
L(ac)
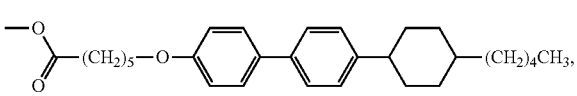
L(ad)
—O—(CH₂)₅—O— ⟨phenyl⟩—⟨phenyl⟩—⟨cyclohexyl⟩—(CH₂)₄CH₃,
L-DC-(a) (4-trans-(4-pentylcyclohexyl)benzamido)phenyl,
L-DC-(d) 4-((trans-(4'-pentyl-[1,1'-bi(cyclohexan)]-4-yl)oxy)carbonyl)phenyl,
L-DC-(g) 4-(4'-(4-pentylcyclohexyl)-[1,1'-biphenyl]-4-carbonyl)piperazin-1-yl,
L-DC-(h) 4-(4-(4-trans-(4-pentylcyclohexyl) phenyl)benzamido)-2-(trifluoromethyl)phenyl, L-DC-(i) 2-methyl-4-trans-(4-((4'-trans-(4-pentylcyclohexyl)biphenyl-4-yloxy)carbonyl)cyclohexanecarboxamido)phenyl, L-DC-(j) 4'-(4'-pentylbi(cyclohexane-4-)carbonyloxy)biphenylcarbonyloxy, L-DC-(k) 4-(((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)carbonyl)piperazin-1-yl, and L-DC-(l) 4-((S)-2-methylbutoxy)phenyl)-10-(4-(((3R,3aS,6S,6aS)-6-(4'-trans-(4-pentylcyclohexyl)biphenylcarbonyloxy)hexahydrofuro[3,2-b]furan-3-yloxy)carbonyl)phenyl, provided that for —$OR^c$ where $R^c$ is the lengthening group $L^2$, the bond between —O and the lengthening group $L^2$ is free of two heteroatoms linked to each other.

2. The photochromic compound of claim 1, wherein $R^2$ is selected from the group consisting of, hydrogen; fluoro; chloro; bromo; linear or branched $C_1$-$C_{10}$ alkyl; linear or branched $C_1$-$C_{10}$ perhaloalkyl; —$OR^a$; —$SR^a$, where each $R^a$ is independently selected from the group consisting of hydrogen, linear or branched $C_1$-$C_{10}$ alkyl, and linear or branched $C_1$-$C_{10}$ perhaloalkyl; —$C(O)OR^b$, where $R^b$ is hydrogen or linear or branched $C_1$-$C_6$ alkyl; substituted or unsubstituted phenyl, each phenyl substituent being independently selected from the group consisting of hydroxyl, halogen, carbonyl, linear or branched $C_1$-$C_{10}$ alkoxycarbonyl, cyano, linear or branched $C_1$-$C_{10}$ haloalkyl, linear or branched $C_1$-$C_{10}$ alkyl, linear or branched $C_1$-$C_{10}$ alkoxy, and linear or branched $C_1$-$C_{10}$ perhaloalkyl; and the group $Y^1$;

$R^6$ and $R^7$ are each independently selected from the group consisting of, hydrogen; fluoro; chloro; bromo; the lengthening group $L^1$; —$OR^c$; and —$SR^c$, where each $R^c$ is independently selected from the group consisting of hydrogen, the lengthening group $L^2$, linear or branched $C_1$-$C_{10}$ alkyl, —C(O)—$R^d$, and —S(O)(O)—$R^e$, where $R^d$ and $R^e$ are each independently selected from the group consisting of linear or branched $C_1$-$C_6$ alkyl, linear or branched $C_1$-$C_6$ perhaloalkyl, phenyl, linear or branched $C_1$-$C_6$ alkyl substituted phenyl, and linear or branched $C_1$-$C_6$ perhaloalkyl substituted phenyl; and $R^1$ independently for each n, and $R^3$ independently for each m are each independently selected from the group consisting of, hydrogen;
cyano;
the lengthening group $L^3$;
halogen selected from the group consisting of fluoro, chloro, and bromo;
linear or branched $C_1$-$C_{10}$ alkyl;
linear or branched $C_1$-$C_{10}$ perhaloalkyl;
$C_3$-$C_7$ cycloalkyl;
—$OR_{10}$';
—S—$R_{10}$';
the group $Y^2$; and
substituted or unsubstituted phenyl, the phenyl substituents being selected from the group consisting of at least one of hydroxyl, halogen, carbonyl, linear or branched $C_1$-$C_{10}$ alkoxycarbonyl, cyano, linear or branched $C_1$-$C_{10}$ haloalkyl, linear or branched $C_1$-$C_{10}$ alkyl, linear or branched $C_1$-$C_{10}$ alkoxy, linear or branched $C_1$-$C_{10}$ perhaloalkyl, and combinations thereof;

wherein each $R_{10}$', of —O—$R_{10}$' and —S—$R_{10}$', independently is hydrogen, linear or branched $C_1$-$C_{10}$ alkyl, phenyl($C_1$-$C_{10}$)alkyl, mono($C_1$-$C_{10}$) alkyl substituted phenyl($C_1$-$C_{10}$)alkyl, mono($C_1$-$C_{10}$)alkoxy substituted phenyl($C_1$-$C_{10}$)alkyl, ($C_1$-$C_{10}$)alkoxy($C_2$-$C_{10}$)alkyl, $C_3$-$C_7$ cycloalkyl, or mono($C_1$-$C_{10}$)alkyl substituted $C_3$-$C_7$ cycloalkyl;

$R^4$ and $R^5$ are each independently selected from the group consisting of, hydrogen; linear or branched $C_1$-$C_{10}$ alkyl; linear or branched $C_1$-$C_{10}$ haloalkyl; $C_3$-$C_7$ cycloalkyl; and the group $Y^3$; or $R^4$ and $R^5$ together form a spiro substituent that is a substituted or unsubstituted spiro-carbocyclic ring containing 3 to 10 carbon atoms; and B and B' are in each case independently selected from the group consisting of:

an aryl group that is mono-substituted with a reactive substituent; a substituted phenyl; a substituted aryl; a substituted 9-julolindinyl; a substituted heteroaromatic group selected from the group consisting of pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolindinyl, or heteroaromatic substituent is a reactive substituent R; an unsubstituted, mono-, di-, or tri-substituted phenyl or aryl group; 9-julolidinyl; or an unsubstituted, mono- or di-substituted heteroaromatic group selected from the group consisting of pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein each of the phenyl, aryl and heteroaromatic substituents are each independently:

hydroxyl, a group —C(=O)$R_{21}$, wherein $R_{21}$ is —$OR_{22}$, —N($R_{23}$)$R_{24}$, piperidino, or morpholino, wherein $R_{22}$ is allyl, linear or branched $C_1$-$C_{20}$ alkyl, phenyl, mono($C_1$-$C_{20}$)alkyl substituted phenyl, mono($C_1$-$C_{20}$)alkoxy substituted phenyl, phenyl($C_1$-$C_{20}$)alkyl, mono($C_1$-$C_{20}$)alkyl substituted phenyl($C_1$-$C_{20}$)alkyl, mono($C_1$-$C_{20}$)alkoxy substituted phenyl($C_1$-$C_{20}$)alkyl, $C_1$-$C_{20}$ alkoxy($C_2$-$C_{20}$)alkyl or $C_1$-$C_{20}$ haloalkyl, $R_{23}$ and $R_{24}$ are each independently $C_1$-$C_{20}$ alkyl, $C_5$-$C_{10}$ cycloalkyl, phenyl or substituted phenyl, the phenyl substituents being $C_1$-$C_{20}$ alkyl or $C_1$-$C_{20}$ alkoxy, and the halo substituent is chloro or fluoro, aryl, mono($C_1$-$C_{20}$)alkoxyaryl, di($C_1$-$C_{20}$)alkoxyaryl, mono($C_1$-$C_{20}$)alkylaryl, di($C_1$-$C_{20}$)alkylaryl, haloaryl, $C_3$-$C_{10}$ cycloalkylaryl, $C_3$-$C_{10}$cycloalkyl, $C_3$-$C_{10}$ cycloalkyloxy, $C_3$-$C_{10}$ cycloalkyloxy($C_1$-$C_{20}$)alkyl, $C_3$-$C_{10}$ cycloalkyloxy($C_1$-$C_{20}$)alkoxy, aryl($C_1$-$C_{20}$)alkyl, aryl($C_1$-$C_{20}$)alkoxy, aryloxy, aryloxy($C_1$-$C_{20}$)alkyl, aryloxy($C_1$-$C_{20}$)alkoxy, mono- or di($C_1$-$C_{20}$)alkylaryl($C_1$-$C_{20}$)alkyl, mono- or di-($C_1$-$C_{20}$)alkoxyaryl($C_1$-$C_{20}$)alkyl, mono- or di-($C_1$-$C_{20}$)alkylaryl($C_1$-$C_{20}$)alkoxy, mono- or di-($C_1$-$C_{20}$)alkoxyaryl($C_1$-$C_{20}$)alkoxy, amino, mono- or di-($C_1$-$C_{20}$)alkylamino, diarylamino, piperazino, N—($C_1$-$C_{20}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{20}$ alkyl, $C_1$-$C_{20}$ haloalkyl, $C_1$-$C_{20}$ alkoxy, mono($C_1$-$C_{20}$)alkoxy($C_1$-$C_{20}$)alkyl, acryloxy, methacryloxy, or halogen;

an unsubstituted or mono-substituted group selected from the group consisting of pyrazolyl, imidazolyl, pyrazolinyl, imidazolinyl, pyrrolinyl, phenothiazinyl, phenoxazinyl, phenazinyl, and acridinyl, each of the substituents being $C_1$-$C_{20}$ alkyl, $C_1$-$C_{20}$ alkoxy, phenyl, or halogen;

a group represented by one of:

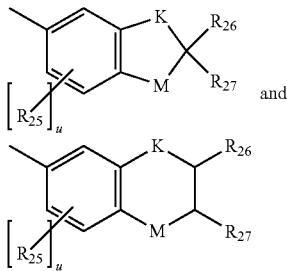 and wherein K is —$CH_2$— or —O—, and M is —O— or substituted nitrogen, provided that when M is substituted nitrogen, K is —$CH_2$—, the substituted nitrogen substituents being hydrogen, $C_1$-$C_{20}$ alkyl, or $C_1$-$C_{20}$ acyl, each $R_{25}$ being independently chosen for each occurrence from $C_1$-$C_{20}$ alkyl, $C_1$-$C_{20}$ alkoxy, hydroxy, and halogen, $R_{26}$ and $R_{27}$ each being independently hydrogen or $C_1$-$C_{20}$ alkyl, and u is an integer ranging from 0 to 2; or a group represented by:

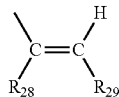

wherein $R_{28}$ is hydrogen or $C_1$-$C_{20}$ alkyl, and $R_{29}$ is an unsubstituted, mono-, or di-substituted group selected from the group consisting of naphthyl, phenyl, furanyl, and thienyl, wherein the substituents are $C_1$-$C_{20}$ alkyl, $C_1$-$C_{20}$ alkoxy, or halogen; or B and B' taken together form one of a fluoren-9-ylidene, mono-, or di-substituted fluoren-9-ylidene, each of the fluoren-9-ylidene substituents being independently selected from the group consisting of $C_1$-$C_{20}$ alkyl, $C_1$-$C_{20}$ alkoxy, and halogen;

wherein independently for each group $Y^1$, $Y^2$, and $Y^3$, each cyclic ester monomer, of each ring-opened cyclic ester monomer, is independently represented by the following Formula (A),

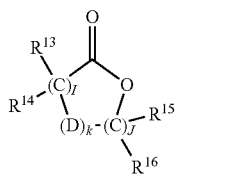

wherein for Formula (A), I and J are each independently integers ranging from 1 to 8; $R^{13}$, $R^{14}$, $R^{15}$, and $R^{16}$ are independently chosen for each carbon unit $(C)_I$ and $(C)_J$ from —H and C1-C16 alkyl; k is 0 or 1; and D is —O— when k is 1; and each cyclic carbonate monomer, of each ring-opened cyclic carbonate monomer, is independently represented by the following Formula (B),

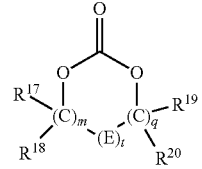

wherein for Formula (B), m and q are each independently integers ranging from 1 to 3; $R^{17}$, $R^{18}$, $R^{19}$, and $R^{20}$ are each independently chosen for each carbon unit $(C)_m$ and $(C)_q$ from —H and C1-C16 alkyl; t is 0 or 1; and E is —O— when t is 1.

3. The photochromic compound of claim 2, wherein $R^2$ is selected from the group consisting of, hydrogen; fluoro; chloro; bromo; linear or branched $C_1$-$C_6$ alkyl; linear or branched $C_1$-$C_6$ perhaloalkyl; —$OR^a$; —$SR^a$, where each $R^a$ is independently selected from the group consisting of hydrogen, linear or branched $C_1$-$C_6$ alkyl, and linear or branched $C_1$-$C_6$ perhaloalkyl; —C(O)$OR^b$, where $R^b$ is hydrogen or linear or branched $C_1$-$C_3$ alkyl; substituted or unsubstituted phenyl, each phenyl substituent being independently selected from the group consisting of hydroxyl, halogen, linear or branched $C_1$-$C_6$ alkoxycarbonyl, cyano, linear or branched $C_1$-$C_6$ haloalkyl, linear or branched $C_1$-$C_6$ alkyl, linear or branched $C_1$-$C_6$ alkoxy, and linear or branched $C_1$-$C_6$ perhaloalkyl; and the group $Y^1$;

$R^6$ and $R^7$ are each independently selected from the group consisting of, hydrogen; fluoro; chloro; bromo; the lengthening group $L^1$; —$OR^c$; and —$SR^c$ where each $R^c$ is independently selected from the group consisting of hydrogen, the lengthening group $L^2$, linear or branched $C_1$-$C_6$ alkyl, —C(O)—$R^d$, and —S(O)(O)—$R^e$, where $R^d$ and $R^e$ are each independently selected from the group consisting of linear or branched $C_1$-$C_3$ alkyl, linear or branched $C_1$-$C_3$ perhaloalkyl, phenyl, linear or branched $C_1$-$C_3$ alkyl substituted phenyl, and linear or branched $C_1$-$C_3$ perhaloalkyl substituted phenyl, $R^1$ independently for each n, and $R^3$ independently for each m are each independently selected from the group consisting of,
hydrogen;
cyano;
the lengthening group $L^3$;
linear or branched $C_1$-$C_6$ alkyl;
$C_3$-$C_6$ cycloalkyl;
linear or branched $C_1$-$C_8$ perhaloalkyl;
fluoro;
chloro;
bromo,
—$OR_{10}$',
S—$R_{10}$';
the group $Y^2$; and
substituted or unsubstituted phenyl, the phenyl substituents being selected from the group consisting of at least one of hydroxyl, halogen, linear or branched $C_1$-$C_6$ alkoxycarbonyl, cyano, linear or branched $C_1$-$C_6$ haloalkyl, linear or branched $C_1$-$C_6$ alkyl, linear or branched $C_1$-$C_6$ alkoxy, and linear or branched $C_1$-$C_6$ perhaloalkyl;

wherein each $R_{10}'$, of —O—$R_{10}'$ and —S—$R_{10}'$, independently is hydrogen, linear or branched $C_1$-$C_6$ alkyl, phenyl($C_1$-$C_6$)alkyl, mono($C_1$-$C_6$)alkyl substituted phenyl($C_1$-$C_6$)alkyl, mono($C_1$-$C_6$) alkoxy substituted phenyl($C_1$-$C_6$)alkyl, ($C_1$-$C_6$) alkoxy($C_2$-$C_6$)alkyl, $C_3$-$C_6$ cycloalkyl, or mono ($C_1$-$C_6$)alkyl substituted $C_3$-$C_6$ cycloalkyl;

$R^4$ and $R^5$ are each independently selected from the group consisting of, hydrogen; linear or branched $C_1$-$C_8$ alkyl; linear or branched $C_1$-$C_8$ haloalkyl; $C_3$-$C_6$ cycloalkyl; and the group $Y^3$; or $R^4$ and $R^5$ together form a spiro substituent that is a substituted or unsubstituted spiro-carbocyclic ring containing 3 to 10 carbon atoms; and B and B' are in each case independently selected from the group consisting of,
unsubstituted aryl,
aryl substituted with linear or branched $C_1$-$C_6$ alkoxy,
aryl substituted with linear or branched $C_1$-$C_6$ perhaloalkyl,
aryl substituted with morpholino, and
aryl substituted with piperidino wherein independently for each group $Y^1$, $Y^2$, and $Y^3$, each cyclic ester monomer, of each ring-opened cyclic ester monomer, is independently selected from the group consisting of, □(epsilon)-caprolactone; □(zeta)-enantholactone; □(delta)-valerolactone; a monoalkyl □(delta)-valerolactone; a monoalkyl-, dialkyl-, or trialkyl-(epsilon)-caprolactone; □(beta)-lactones; □(gamma)-lactones; dilactones; and ketodioxanones; and each cyclic carbonate monomer, of each ring-opened cyclic carbonate monomer, is independently selected from the group consisting of, ethylene carbonate; 3-ethyl-3-hydroxylmethyl trimethylene carbonate; propylene caronate, trimethylene carbonate; trimethylolpropane monocarbonate; 4,6-dimethyl-1,3-propylene carbonate; 2,2-dimethyl trimethylene carbonate; and 1,2-dioxepan-2-one.

4. The photochromic compound of claim 1, wherein at least one of $R^6$ and $R^7$ is selected from the group consisting of the lengthening group $L^1$ and —$OR^c$ where $R^c$ is the lengthening group $L^2$.

5. The photochromic compound of claim 4, wherein $R^6$ and $R^7$ are each independently selected from the group consisting of the lengthening group $L^1$ and —$OR^c$ where $R^c$ is the lengthening group $L^2$.

6. The photochromic compound of claim 4, wherein $R^3$ at position-11 is selected from the group consisting of, halogen, —CN, linear or branched $C_1$-$C_8$ perhaloalkyl, unsubstituted phenyl, and phenyl substituted with at least one of halogen and linear or branched $C_1$-$C_8$ perhaloalkyl.

7. The photochromic compound of claim 4, wherein $R^3$ at position-11 is halogen.

8. The photochromic compound of claim 1, wherein $R^6$ is selected from the group consisting of the lengthening group $L^1$ and —$OR^c$ where $R^c$ is the lengthening group $L^2$, and $R^7$ is halogen.

9. The photochromic compound of claim 1, wherein $R^3$ at position-12 is the lengthening group $L^3$.

10. A photochromic compound represented by the following Formula (III), $$L^y\text{-}(PC)_{n'} \qquad \text{Formula (III)}$$

wherein, n' is at least 2,

PC independently for each n' is a residue of the photochromic compound of claim 1, and $L^y$ is a multivalent linking group selected from the group consisting of,
a first multivalent compound that is a multivalent polymer, and
a second multivalent compound that is different than the first multivalent compound, the second multivalent compound being non-polymeric and comprising a residue selected from the group consisting of, a residue of a polyisocyanate, a residue of a polyol, a residue of a polycarboxylic acid, a residue of a polycarbonate functional material, and combinations thereof.

11. The photochromic compound of claim 10, wherein the multivalent polymer, of the first multivalent compound, is selected from the group consisting of multivalent polyurethane, multivalent polyester, multivalent polyether, multivalent poly(meth)acrylate, multivalent polyvinylalcohol, multivalent polycarbonate, multivalent polysiloxane, and multivalent cyclic polysiloxane, and for the second multivalent compound,
the polyisocyanate is selected from the group consisting of aliphatic polyisocyanates, cycloaliphatic polyisocyanates, heterocyclic polyisocyanates, and aromatic polyisocyanates, each independently having at least two isocyanate groups, dimers thereof, trimers thereof, and mixtures of one or more thereof,
the polyol is selected from the group consisting of aliphatic polyols, cycloaliphatic polyols, heterocyclic polyols, and aromatic polyols, each independently having at least two hydroxyl groups,
the polycarboxylic acid is selected from the group consisting of aliphatic polycarboxylic acids, cycloaliphatic polycarboxylic acids, heterocyclic polycarboxylic acids, and aromatic polycarboxylic acids, each independently having at least two carboxylic acid groups, and
the polycarbonate functional material is selected from the group consisting of aliphatic polycarbonate functional compounds, cycloaliphatic polycarbonate functional compounds, heterocyclic polycarbonate functional compounds, and aromatic polycarbonate functional compounds, each independently having at least two cyclic carbonate groups.

12. A photochromic composition comprising the photochromic compound of claim 1.

\* \* \* \* \*

UNITED STATES PATENT AND TRADEMARK OFFICE
CERTIFICATE OF CORRECTION

PATENT NO. : 11,453,654 B2
APPLICATION NO. : 16/500930
DATED : September 27, 2022
INVENTOR(S) : Anil Kumar et al.

It is certified that error appears in the above-identified patent and that said Letters Patent is hereby corrected as shown below:

In the Claims

Column 85, Line 59, Claim 1, delete "L(31)-(4-(9" and insert -- L(31) 4-(4-(9 --

Column 89, Line 57, Claim 2, delete "--OR$_{10}$';" and insert -- --O --R$_{10}$'; --

Column 90, Line 19, Claim 2, delete "9-julolindinyl;" and insert -- 9-julolidinyl; --

Column 90, Line 25, Claim 2, delete "9-julolindinyl," and insert -- 9-julolidinyl, --

Column 90, Line 49, Claim 2, delete "di(C$_1$" and insert -- di-(C$_1$ --

Column 90, Line 50, Claim 2, delete "di(C$_1$" and insert -- di-(C$_1$ --

Column 90, Line 51, Claim 2, delete "C$_3$-C$_{10}$cycloalkyl," and insert -- C$_3$-C$_{10}$ cycloalkyl, --

Column 90, Line 56, Claim 2, delete "di(C$_1$" and insert -- di-(C$_1$ --

Column 91, Line 66, Claim 2, delete "C1-C16" and insert -- C$_1$-C$_{16}$ --

Column 92, Line 18, Claim 2, delete "C1-C16" and insert -- C$_1$-C$_{16}$ --

Signed and Sealed this
Twenty-second Day of August, 2023

*Katherine Kelly Vidal*

Katherine Kelly Vidal
*Director of the United States Patent and Trademark Office*